(12) United States Patent
Ginn et al.

(10) Patent No.: US 12,582,528 B2
(45) Date of Patent: *Mar. 24, 2026

(54) SYSTEMS FOR SACROILIAC JOINT STABILIZATION

(71) Applicant: Tenon Medical, Inc., Los Gatos, CA (US)

(72) Inventors: Richard S Ginn, Gilroy, CA (US); Richard Brown, Colorado Springs, CO (US); Daren Stewart, Belmont, CA (US)

(73) Assignee: Tenon Medical, Inc., Los Gatos, CA (US)

( * ) Notice: Subject to any disclaimer, the term of this patent is extended or adjusted under 35 U.S.C. 154(b) by 961 days.

This patent is subject to a terminal disclaimer.

(21) Appl. No.: 17/833,960

(22) Filed: Jun. 7, 2022

(65) Prior Publication Data

US 2022/0304813 A1     Sep. 29, 2022

Related U.S. Application Data

(63) Continuation-in-part of application No. 17/833,098, filed on Jun. 6, 2022, which is a continuation of
(Continued)

(51) Int. Cl.
*A61F 2/44*       (2006.01)
*A61B 5/055*      (2006.01)
(Continued)

(52) U.S. Cl.
CPC .......... *A61F 2/30988* (2013.01); *A61B 5/055* (2013.01); *A61B 5/062* (2013.01);
(Continued)

(58) Field of Classification Search
CPC ........... A61B 17/17–1796; A61F 2002/30995
See application file for complete search history.

(56) References Cited

U.S. PATENT DOCUMENTS 6,063,088 A * 5/2000 Winslow ............... A61F 2/4611
606/279
6,228,022 B1 * 5/2001 Friesem ............. A61B 17/3421
604/164.08

(Continued)

*Primary Examiner* — Lynnsy M Summitt

(74) *Attorney, Agent, or Firm* — Francis Law Group

(57) ABSTRACT

Systems are described for conducting minimally invasive medical interventions utilizing instruments and assemblies thereof to stabilize and/or fixate a dysfunctional sacroiliac (SI) joint. The systems include a drill guide adapted to create a pilot SI joint opening in the dysfunctional SI joint through an incision comprising a length no greater than 3.0 cm; portions of the pilot SI joint opening being disposed in the sacrum and ilium bone structures. The drill guide includes a tri-mode fixation system adapted to position and stabilize the drill guide during creation of the pilot SI joint opening in the dysfunctional SI joint and delivery of the SI joint prosthesis therein. The systems also include a SI joint prosthesis configured to be inserted into the pilot SI joint opening of the dysfunctional SI joint, and a prosthesis deployment assembly configured to engage the SI joint prosthesis and advance the SI joint prosthesis into the dysfunctional SI joint.

14 Claims, 61 Drawing Sheets

Related U.S. Application Data application No. 17/749,199, filed on May 20, 2022, now Pat. No. 12,465,491, which is a continuation-in-part of application No. 17/740,568, filed on May 10, 2022, which is a continuation-in-part of application No. 17/463,779, filed on Sep. 1, 2021, now Pat. No. 12,427,027, which is a continuation-in-part of application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.

| | |
|---|---|
| *A61B 5/06* | (2006.01) |
| *A61B 6/00* | (2006.01) |
| *A61B 6/03* | (2006.01) |
| *A61B 8/08* | (2006.01) |
| *A61B 17/16* | (2006.01) |
| *A61B 17/70* | (2006.01) |
| *A61B 17/88* | (2006.01) |
| *A61B 34/20* | (2016.01) |
| *A61F 2/30* | (2006.01) |
| *A61F 2/46* | (2006.01) |

(52) U.S. Cl.
CPC .............. *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); *A61F 2002/30166* (2013.01); *A61F 2002/30593* (2013.01); *A61F 2002/30995* (2013.01)

(56) References Cited

U.S. PATENT DOCUMENTS

| | | | | |
|---|---|---|---|---|
| 9,119,732 | B2 * | 9/2015 | Schifano | A61B 17/7055 |
| 9,241,798 | B2 * | 1/2016 | Petersen | A61B 17/025 |
| 10,376,367 | B2 * | 8/2019 | Fallin | A61B 17/8004 |
| 11,083,511 | B2 * | 8/2021 | Schifano | A61F 2/4611 |
| 2004/0176775 | A1 * | 9/2004 | Burkus | A61B 90/94 |
| | | | | 606/90 |
| 2014/0200668 | A1 * | 7/2014 | Kirschman | A61B 17/025 |
| | | | | 623/17.16 |

* cited by examiner

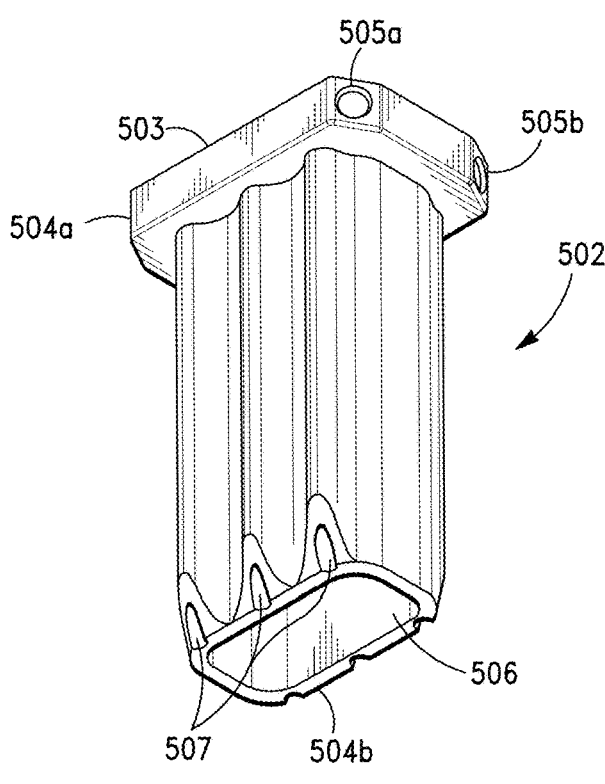
FIG. 3B
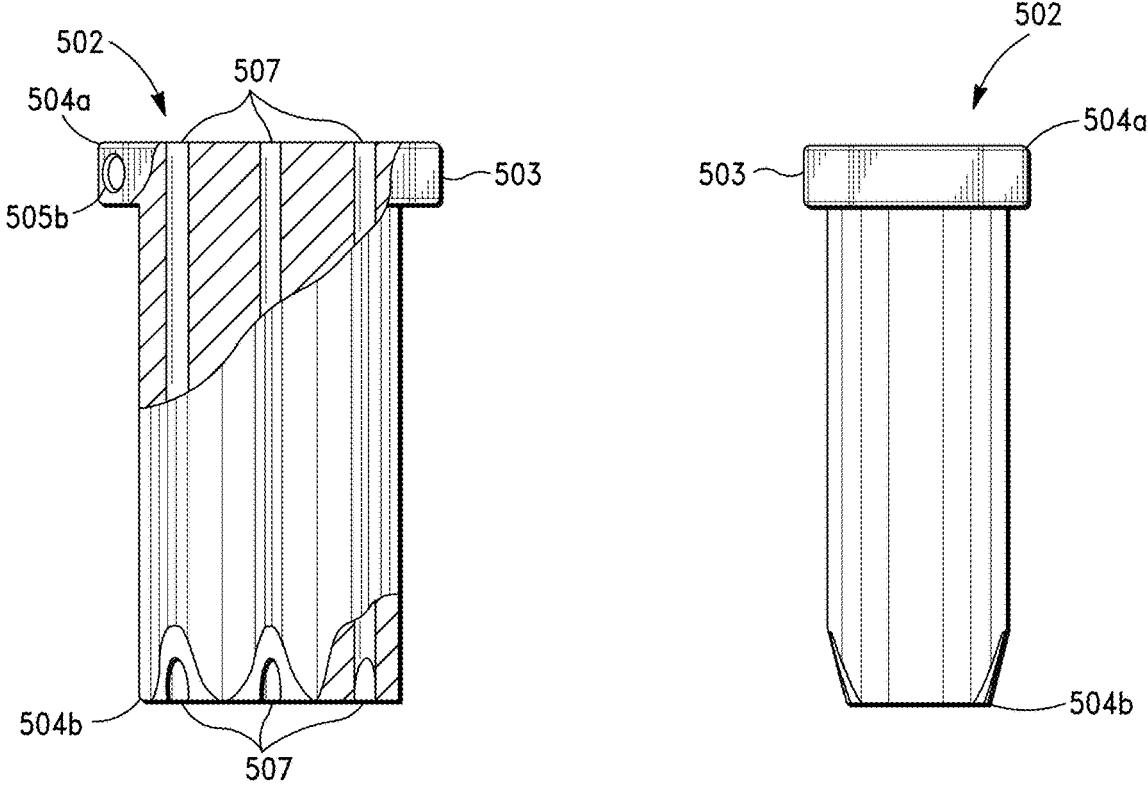
FIG. 3C          FIG. 3D

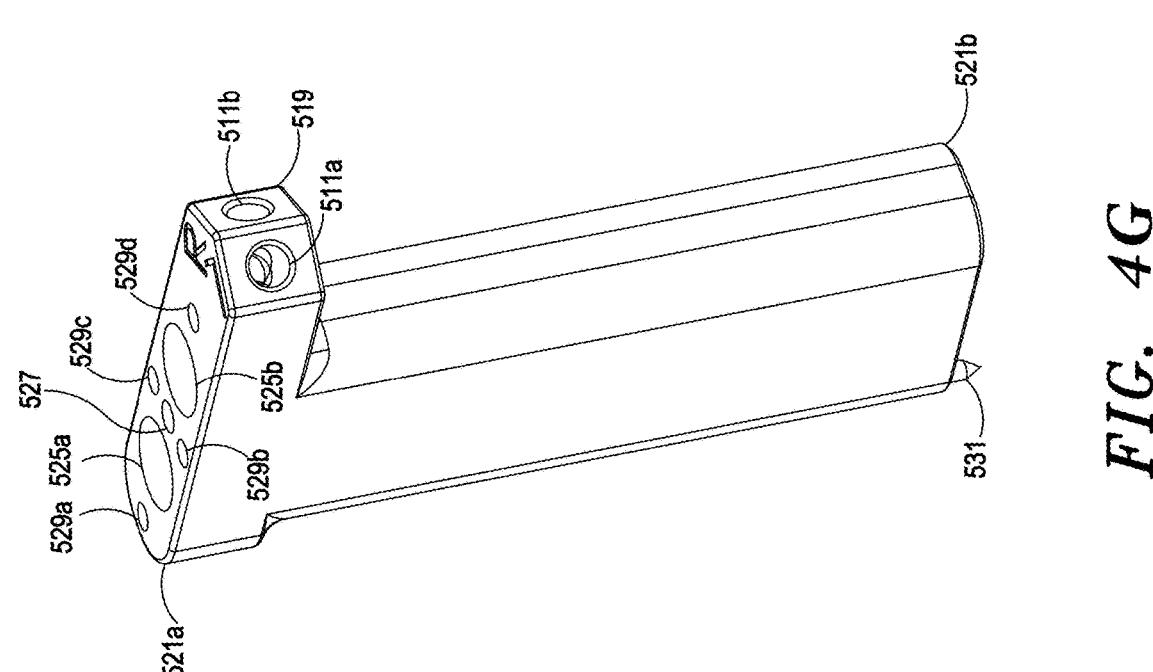
*FIG. 4G*

503b

501a

503a

503d

501c

503f

513

518

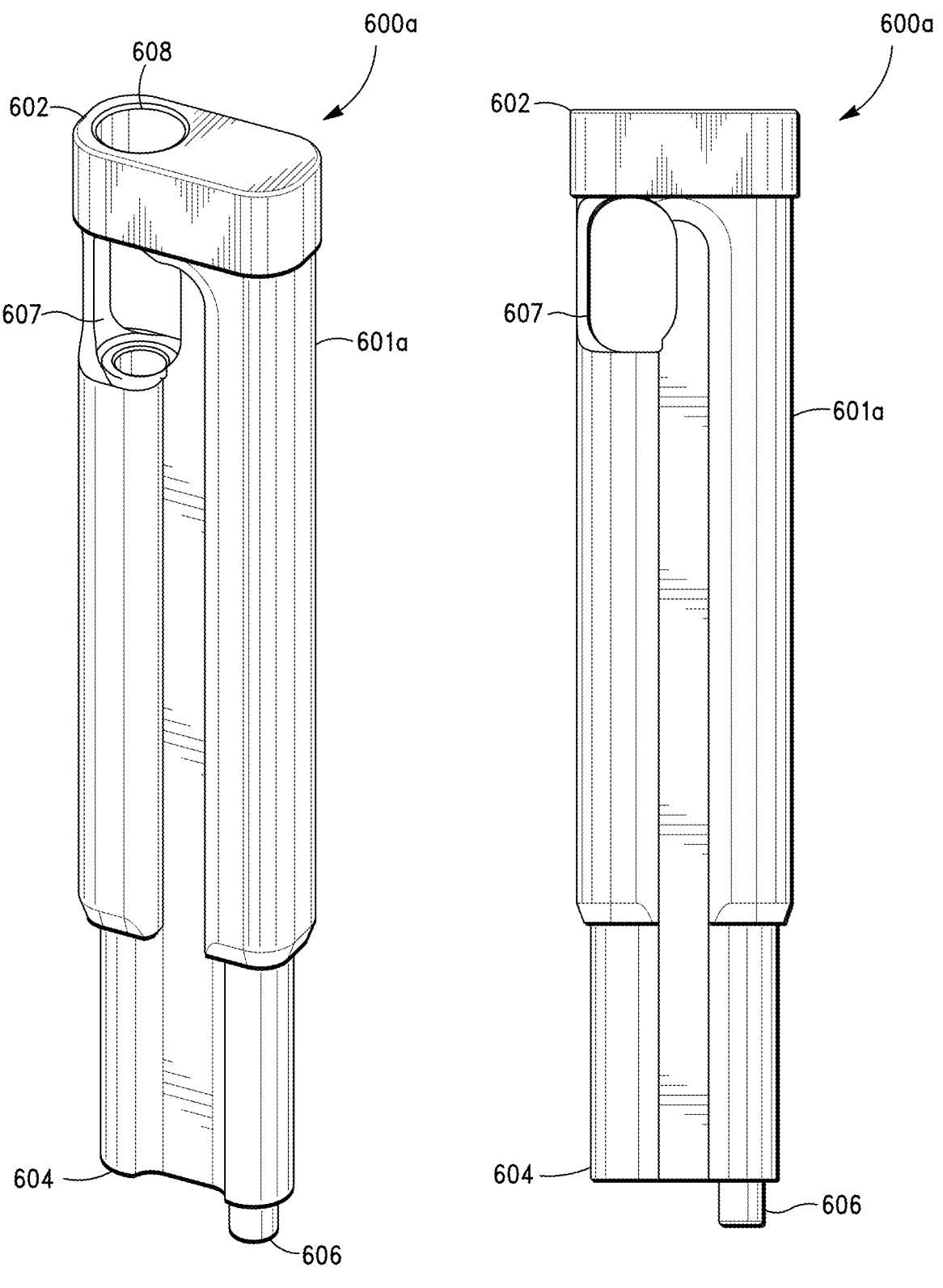
*FIG. 8A*          *FIG. 8B*

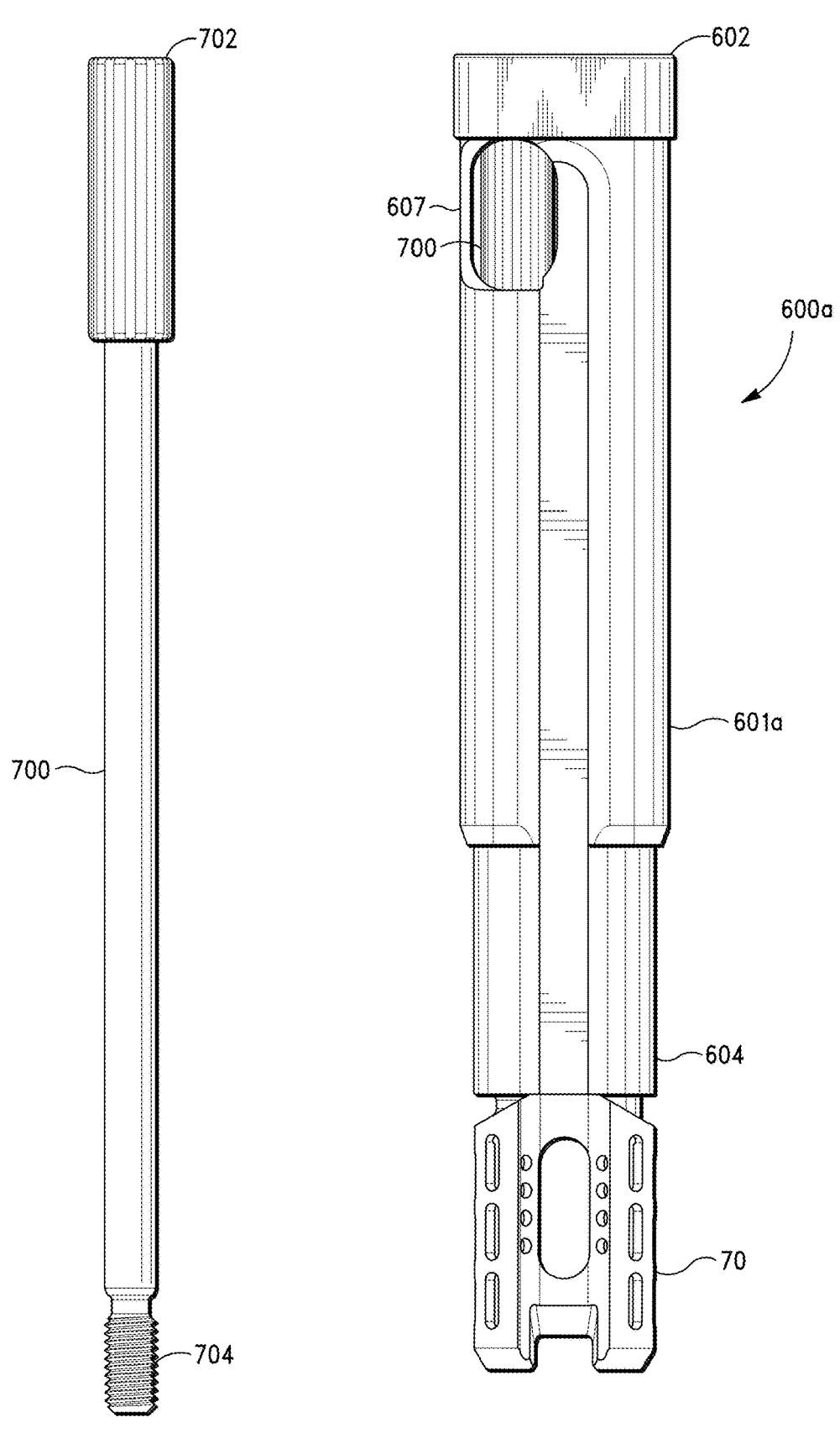
*FIG. 8F*        *FIG. 8G*

SYSTEMS FOR SACROILIAC JOINT STABILIZATION

CROSS-REFERENCES TO RELATED APPLICATIONS

This application is a continuation-in-part of U.S. application Ser. No. 17/833,098, filed Jun. 6, 2022, which is a continuation of U.S. patent application Ser. No. 17/749,199, filed on May 20, 2022, which is a continuation-in-part application of U.S. patent application Ser. No. 17/740,568, filed on May 10, 2022, which is a continuation-in-part application of U.S. patent application Ser. No. 17/463,779, filed Sep. 1, 2021, which is a continuation-in part of U.S. patent application Ser. No. 13/857,977, filed Apr. 5, 2013, now U.S. Pat. No. 11,273,042, which is a continuation application of U.S. patent application Ser. No. 13/192,289, filed Jul. 27, 2011, now abandoned, which claims the benefit of U.S. provisional patent application Ser. No. 61/368,233, filed Jul. 27, 2010.

FIELD OF THE INVENTION

The present invention relates to methods, systems and apparatus for stabilizing junctions between bone structures. More particularly, the present invention relates to methods, systems and apparatus for stabilizing dysfunctional sacroiliac (SI) joints.

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As further illustrated in FIGS. 1B-1D, the SI joint 6 generally comprises the shape of an inverted capital letter "L" (denoted "13") lying on its side (rather than a triangle), where the long arm of the inverted "L" 15 (i.e., SI joint 6) is oriented along the posterior wall of the pelvis 11 (denoted "25" in FIG. 1A) and is also oriented relatively straight through its entire course. The sacral floor (denoted "21" in FIG. 1C), which is defined by the region between the anterior sacral promontory 19a and the apex 19b of the sacrum 2, generally slopes downward and laterally at an approximately 30% grade relative to the cephalocaudal axis 27.

As illustrated in FIGS. 1B and 1C, the short arm of the inverted "L" (denoted "17") is generally oriented parallel to the transverse plane of the L5-S1 lumbosacral joint and limited superiorly by the sacral ala (denoted "23" in FIG. 1C).

The apex of the inverted "L" (denoted "29" in FIG. 1B) is positioned below the S2 segment region of the sacrum 2 (denoted "S2") proximate to the S3 segment region of the sacrum 2 (denoted "S3").

As is also well known in the art, the SI joint further comprises a SI joint dorsal recess or gap 7 that is disposed between the sacrum 2 and ilium 4 proximate the S2 segment region of the sacrum 2, as illustrated in FIG. 1D.

As is further well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIG. 1A) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3°, approximately 1.5° in axial rotation and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

Various non-surgical methods, such as administration of pharmacological agents, e.g., the corticosteroid prednisone, and surgical methods and devices, i.e., SI joint prostheses, have been developed and employed to treat SI joint dysfunction.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a SI joint prosthesis proximate to or in a dysfunctional SI joint and is generally characterized by the direction of access to the dysfunctional SI joint, i.e., anterior, posterior or lateral.

Although several conventional SI joint stabilization surgical methods and associated bone prostheses have effectively ameliorated pain associated with SI joint dysfunction, there remains many disadvantages associated with the conventional surgical methods and associated SI joint prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive systems and methods for SI joint stabilization have thus been developed to address the noted disadvantages associated with open surgery methods. Although conventional minimally-invasive SI joint stabilization systems and methods, such as the systems and methods disclosed in U.S. Pub. No. 2009/0076551 to Petersen, have garnered some success in relieving pain associated with SI joint dysfunction and have effectively addressed many of the disadvantages associated with open surgery systems and methods, there similarly remains many disadvantages associated with conventional minimally-invasive SI joint stabilization systems and methods.

A major disadvantage associated with many conventional minimally-invasive SI joint stabilization methods is that such methods are difficult to perform and the associated surgical systems often require extensive, system-specific surgical training and experience. Despite the level of surgical training and experience that surgeons possess, when such conventional minimally-invasive SI joint stabilization systems and methods are employed, there is still a substantial incidence of damage to the lumbosacral neurovascular structures proximate to the SI joint.

Further disadvantages associated with many conventional minimally-invasive SI joint stabilization systems and methods are that visualization of the SI joint after creation of a pilot opening for the SI joint prostheses is restricted and arthrodesis of the SI joint bone structures, i.e., ilium and sacrum, is often suboptimal.

A further disadvantage associated with many conventional minimally-invasive SI joint stabilization systems, methods, and associated apparatus, i.e., SI joint prostheses, such as the systems, methods, and joint stabilization prostheses disclosed in U.S. Pub. No. 2009/0076551 to Petersen, is that pre-existing sacral abnormalities can lead to displacement of the implanted prostheses, which can, and often will result in damage to surrounding bone and soft tissue structures.

An additional disadvantage associated with many conventional minimally invasive SI joint stabilization systems and methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a prosthesis in a dysfunctional SI joint.

Further, some conventional minimally-invasive SI joint stabilization methods are particularly prone to failure due to displacement of the SI joint prostheses in the dysfunctional SI joint, such as in or proximate the SI joint dorsal recess referenced above and shown in FIG. 1D, and/or failure of the prostheses to effectively engage the SI joint structures, e.g., articular surfaces of the sacrum and/or ilium.

Various "improved" SI joint prostheses have thus been developed for use in minimally-invasive SI joint stabilization methods or procedures to effectively engage SI joint structures and maintain engagement thereto during SI joint function.

Although many of the "improved" SI joint prostheses, when deployed properly in a dysfunctional SI joint, can, and often will, effectively engage SI joint structures, there remains several disadvantages associated with the prostheses. Illustrative are the SI joint prostheses disclosed in U.S. Pat. No. 8,951,254 to Mayer, et al.

The SI joint prostheses disclosed in U.S. Pat. No. 8,951,254 comprise or are coated with a liquefiable synthetic polymer that is adapted to liquify upon administration of mechanical energy, e.g., high frequency vibration, when implanted and re-solidify thereafter to securely engage the SI joint structures, i.e., sacrum and ilium.

A major disadvantage associated with the noted SI joint prostheses is that the liquefiable synthetic polymers, when re-solidified in situ, are structurally inferior to the osseous or bone tissue of the sacrum and ilium. The fusion sites between the articular surfaces of the sacrum and ilium that define the SI joint are, thus, highly susceptible to structural fatigue and failure, which can, and often will, result in misalignment of the SI joint and ultimately increased pain for the subject.

A further disadvantage associated with the SI joint prostheses disclosed in U.S. Pat. No. 8,951,254 is that the synthetic liquefiable synthetic polymers are also substantially immunogenic and will induce an adverse immune response when the prostheses are implanted in a dysfunctional SI joint. As is well established, the adverse immune response can, and often will, prevent healing and osteogenic processes, e.g., remodeling of damaged osseous tissue and regeneration of new osseous tissue.

It would thus be desirable to provide SI joint stabilization methods, systems and apparatus, which substantially reduce or eliminate the disadvantages associated with conventional SI joint stabilization methods, systems and apparatus.

It is therefore an object of the invention to provide improved SI joint stabilization methods, systems and apparatus, which substantially reduce or eliminate the disadvantages associated with conventional SI joint stabilization methods, systems and apparatus.

It is another object of the invention to provide improved minimally-invasive SI joint stabilization systems and apparatus, and methods of using same, that facilitate posterior placement of prostheses in and, thereby, stabilization of dysfunctional SI joints.

It is another object of the invention to provide improved minimally-invasive SI joint stabilization systems and apparatus, including prostheses, which can be readily employed to stabilize dysfunctional SI joints.

It is another object of the invention to provide improved minimally-invasive SI joint stabilization systems and apparatus, including prostheses, which, when employed to stabilize dysfunctional SI joints, disrupt less tissue and muscles, and avoid nerves and large blood vessels.

It is another object of the invention to provide improved minimally-invasive SI joint stabilization systems and apparatus, including prostheses, which effectively ameliorate pain associated with SI joint dysfunction.

It is another object of the invention to provide improved SI joint prostheses that can readily be employed in minimally-invasive SI joint stabilization methods.

It is another object of the invention to provide improved minimally-invasive SI joint stabilization systems adapted to create pilot openings in dysfunctional SI joints for placement of prostheses therein via a minimal incision.

It is another object of the invention to provide improved minimally-invasive SI joint stabilization systems adapted to create pilot openings in dysfunctional SI joints for placement of prostheses therein, which provide optimal direct visualization of the bone dislodging member thereof and the pilot opening during and after creation of the pilot openings.

It is another object of the invention to provide improved minimally-invasive SI joint stabilization systems that readily receive and guide prostheses into dysfunctional SI joints and provide consistent, optimal arthrodesis of dysfunctional SI joints.

It is another object of the invention to provide improved SI joint prostheses that provide secure engagement to SI joint structures.

It is another object of the invention to provide improved SI joint prostheses that possess optimal structural properties to effectively stabilize dysfunctional SI joints.

It is yet another object of the invention to provide improved SI joint prostheses that facilitate remodeling of damaged osseous tissue and regeneration of new osseous tissue and osseous tissue structures.

SUMMARY OF THE INVENTION

The present invention is directed to minimally-invasive methods, systems and apparatus for stabilizing dysfunctional SI joints. In some embodiments of the invention, there are thus provided minimally-invasive systems for stabilizing dysfunctional SI joints.

In one embodiment, the minimally-invasive system for stabilizing a dysfunctional SI joint comprises:

a tool assembly, a SI joint prosthesis, and a prosthesis deployment assembly, the tool assembly comprising a guide pin adapted to be positioned in the dysfunctional SI joint and a drill guide assembly, the drill guide assembly adapted to create a pilot SI joint opening in the dysfunctional SI joint through an incision comprising a length no greater than 3.0 cm, the drill guide assembly comprising a drill guide, a bone dislodging member, and first, second, and third drill guide fixation sub-systems, the bone dislodging member being adapted to dislodge portions of bone in the dysfunctional SI joint, the drill guide comprising a base and a guide member comprising a guide pin lumen adapted to receive the guide pin therein, the first drill guide fixation sub-system comprising a plurality of anchor members extending from the base of the drill guide that are adapted to pierce and engage biological tissue, the second drill guide fixation sub-system comprising a plurality of Kirschner-wires (K-wires) adapted to pierce and engage first and second bone structures of the dysfunctional SI joint, and other SI joint structures proximate thereto, the third drill guide fixation sub-system comprising a K-wire pin member and a temporary fixation pin, the K-wire pin member, and the temporary fixation pin adapted to pierce and engage the first and second bone structures of the dysfunctional SI joint, the drill guide further comprising a prosthesis internal access opening and a plurality of fixation guide openings, the prosthesis internal access opening comprising a cross-sectional shape that corresponds to the cross-sectional shape of SI joint prosthesis, whereby the SI joint prosthesis can be readily received and positioned in the drill guide, the prosthesis opening comprising first and second lobe portions, the plurality of drill guide lumens adapted to receive the plurality of K-wires therein, the first and second lobe portions of the prosthesis internal access opening adapted to receive the K-wire pin member, the temporary fixation pin, and the bone dislodging member therein, the first drill guide fixation sub-system operable when the plurality of anchor members pierce and engage first biological tissue proximate the dysfunctional SI joint, the second drill guide fixation sub-system operable when the plurality of K-wires is received in the plurality of drill guide lumens and engage the first and second bone structures of the dysfunctional SI joint, the third drill guide fixation sub-system operable when the K-wire pin member is received in the first lobe portion of the prosthesis internal access opening in the drill guide and engages the first bone structure of the dysfunctional SI joint, and when the K-wire pin member is received in the second lobe portion of the prosthesis internal access opening in the drill guide and engages the second bone structure of the dysfunctional SI joint, the third drill guide fixation sub-system further operable when the temporary fixation pin is received in the first lobe portion of the prosthesis internal access opening in the drill guide and engages the first bone structure of the dysfunctional SI joint, and when the temporary fixation pin is received in the second lobe portion of the prosthesis internal access opening in the drill guide and engages the second bone structure of the dysfunctional SI joint, each of the first, second, and third drill guide fixation sub-systems being operable when the K-wire pin member is the received in the first lobe portion of the prosthesis internal access opening in the drill guide and engages the first bone structure of the dysfunctional SI joint, and the bone dislodging member is received in the second lobe portion of the prosthesis internal access opening in the drill guide and creates a first portion of the pilot SI joint in the second bone structure of the dysfunctional SI joint, and when the K-wire pin member is the received in the second lobe portion of the prosthesis internal access opening in the drill guide and engages the second bone structure of the dysfunctional SI joint, and bone dislodging member is received in the first lobe portion of the prosthesis internal access opening in the drill guide and creates a second portion of the pilot SI joint in the first bone structure of the dysfunctional SI joint, each of the first, second, and third drill guide fixation sub-systems further operable when the temporary fixation pin is the received in the first lobe portion of the prosthesis internal access opening in the drill guide and engages the first bone structure of the dysfunctional SI joint, and the bone dislodging member is received in the second lobe portion of the prosthesis internal access opening in the drill guide and creates the first portion of the pilot SI joint in the second bone structure of the dysfunctional SI joint, and when the temporary fixation pin is the received in the second lobe portion of the prosthesis internal access opening in the drill guide and engages the second bone structure of the dysfunctional SI joint, and bone dislodging member is received in the first lobe portion of the prosthesis internal access opening in the drill guide and creates the second portion of the pilot SI joint in the first bone structure of the dysfunctional SI joint, the SI joint prosthesis configured and adapted to be inserted into and through the prosthesis internal access opening in the drill guide and into the pilot SI joint opening, the prosthesis deployment assembly configured and adapted to engage the SI joint prosthesis and guide the SI joint prosthesis into and through the prosthesis internal access opening in the drill guide and into the pilot SI joint opening.

In a preferred embodiment of the invention, the tool assembly is adapted to access the dysfunctional SI joint via a posterior approach.

In some embodiments of the invention, the first bone structure of the dysfunctional SI joint comprises a sacrum bone structure and the second bone structure of the dysfunctional SI joint comprises an ilium bone structure.

In a preferred embodiment, the bone dislodging member comprises a drill bit.

In a preferred embodiment, the drill bit comprises a plurality of graduated markings reflecting a first depth of the drill bit into the first bone structure when the second portion of the pilot SI joint opening is the created in the first bone structure and a second depth of the drill bit into the second bone structure when the first portion of the pilot SI joint opening is the created in the second bone structure.

In a preferred embodiment, the graduated markings are directly visible when the first and second portions of the pilot SI joint opening are created in the first and second bone structures with the drill bit.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 3B is a perspective view of the access sleeve of the drill guide assembly shown in FIG. 3A, in accordance with the invention;

FIG. 3C is a front plan view of the access sleeve shown in FIG. 3B, in accordance with the invention;

FIG. 3D is a right-side plan view of the access sleeve shown in FIG. 3B, in accordance with the invention;

FIG. 4G is a further perspective view of the drill guide shown in FIG. 4C, in accordance with the invention;

FIG. 8A is a perspective view of one embodiment of a prosthesis deployment assembly, in accordance with the invention;

FIG. 8B is a front plan view of the prosthesis deployment assembly shown in FIG. 8A, in accordance with the invention;

FIG. 8F is a front plan view of a prosthesis engagement rod of the prosthesis deployment assembly shown in FIG. 8A, in accordance with the invention;

FIG. 8G is a perspective view of the prosthesis deployment assembly shown in FIG. 8A engaged to a prosthesis of the invention, in accordance with the invention;

FIG. 13I is a CT scan image showing a modified AP view of the dysfunctional SI joint shown in FIG. 13B, showing a SI joint prosthesis properly positioned therein, in accordance with the invention;

DETAILED DESCRIPTION OF THE PREFERRED EMBODIMENT

Figure 1A:
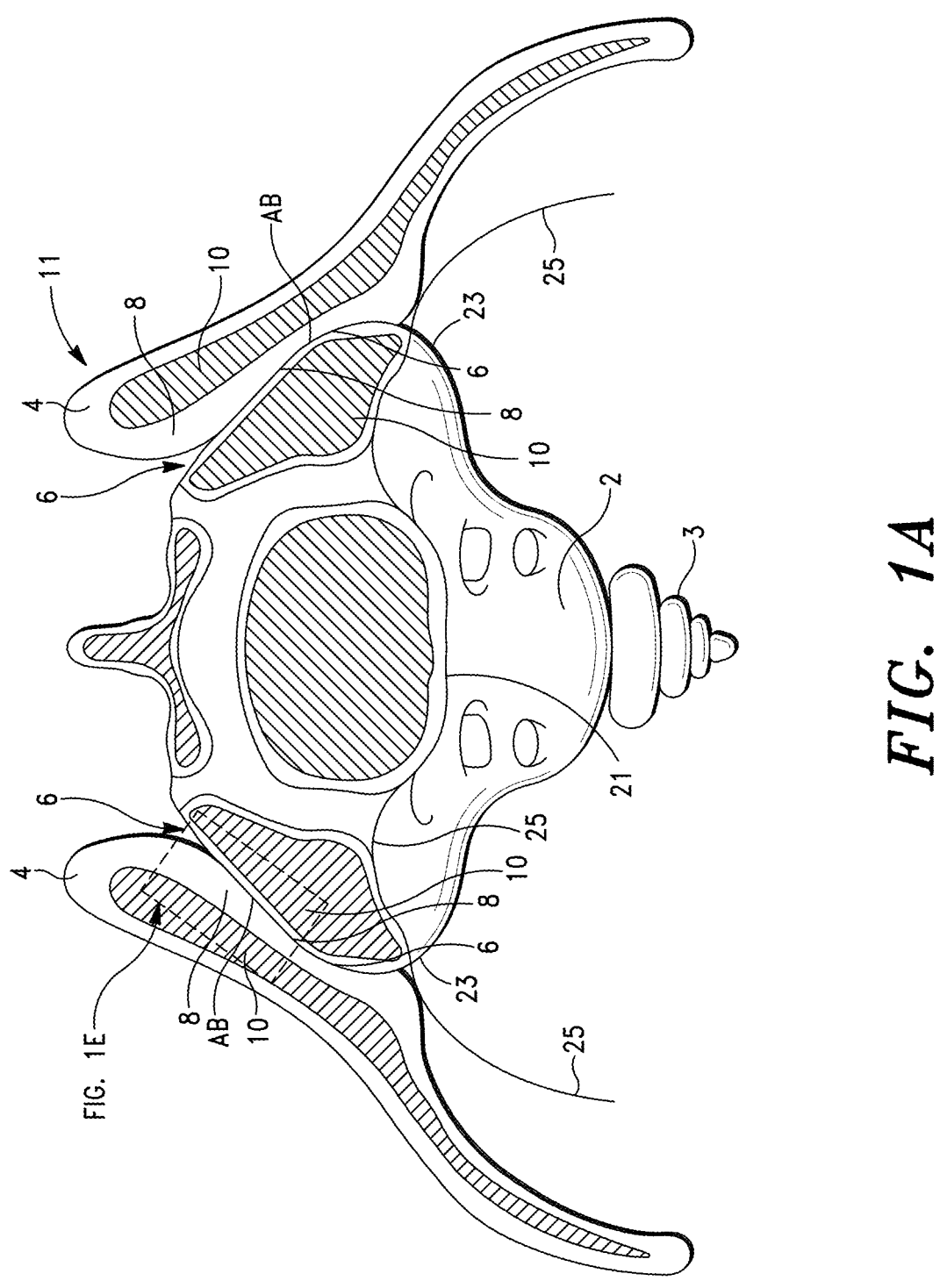
FIG. 1A is a schematic illustration of a human pelvic region from an anteroposterior (AP) perspective showing the SI joints thereof.
Figure 1B:
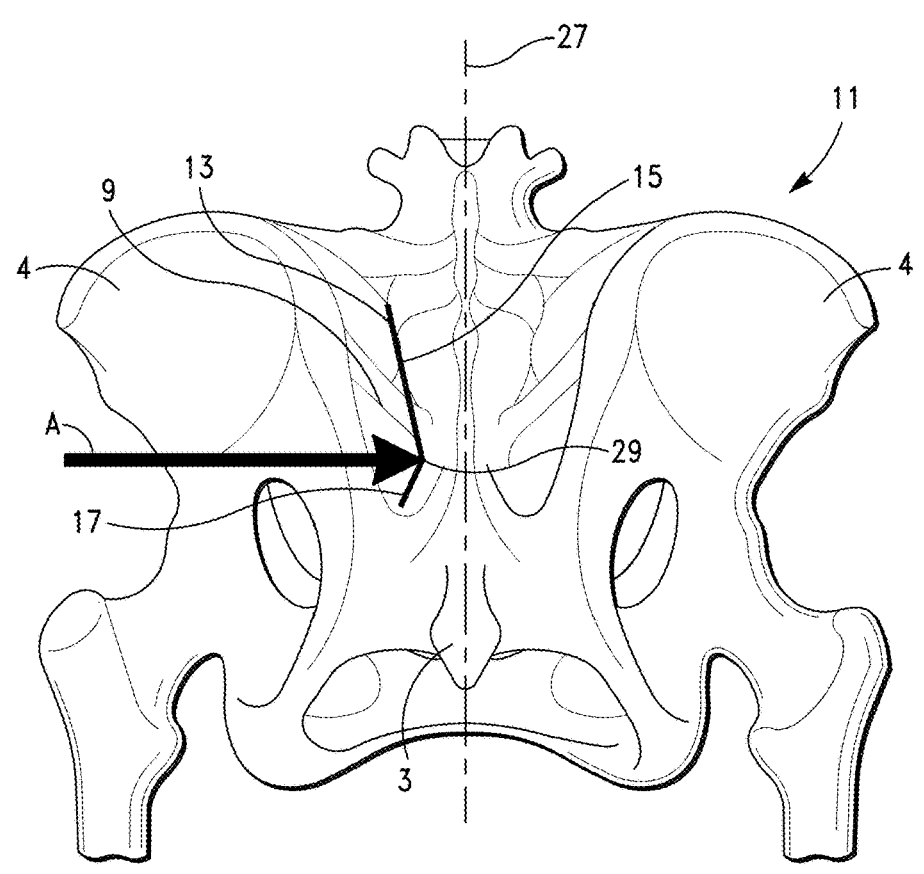
FIG. 1B is another schematic illustration of a human pelvic region from a posterior perspective showing the adjoining sacrum and ilium bone structures, and ligamentous structures thereof.
Figure 1C:
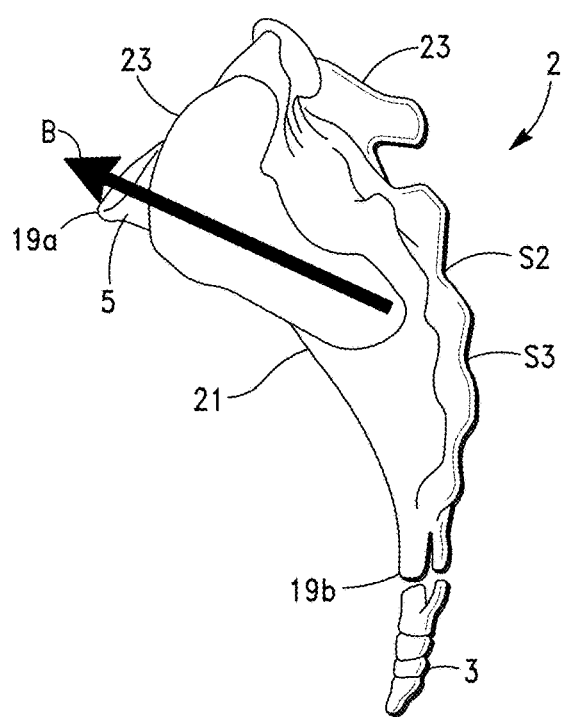
FIG. 1C is a schematic illustration of the sacrum and coccyx from a lateral perspective showing the sacral promontory and the articular surface of sacrum.
Figure 1D:
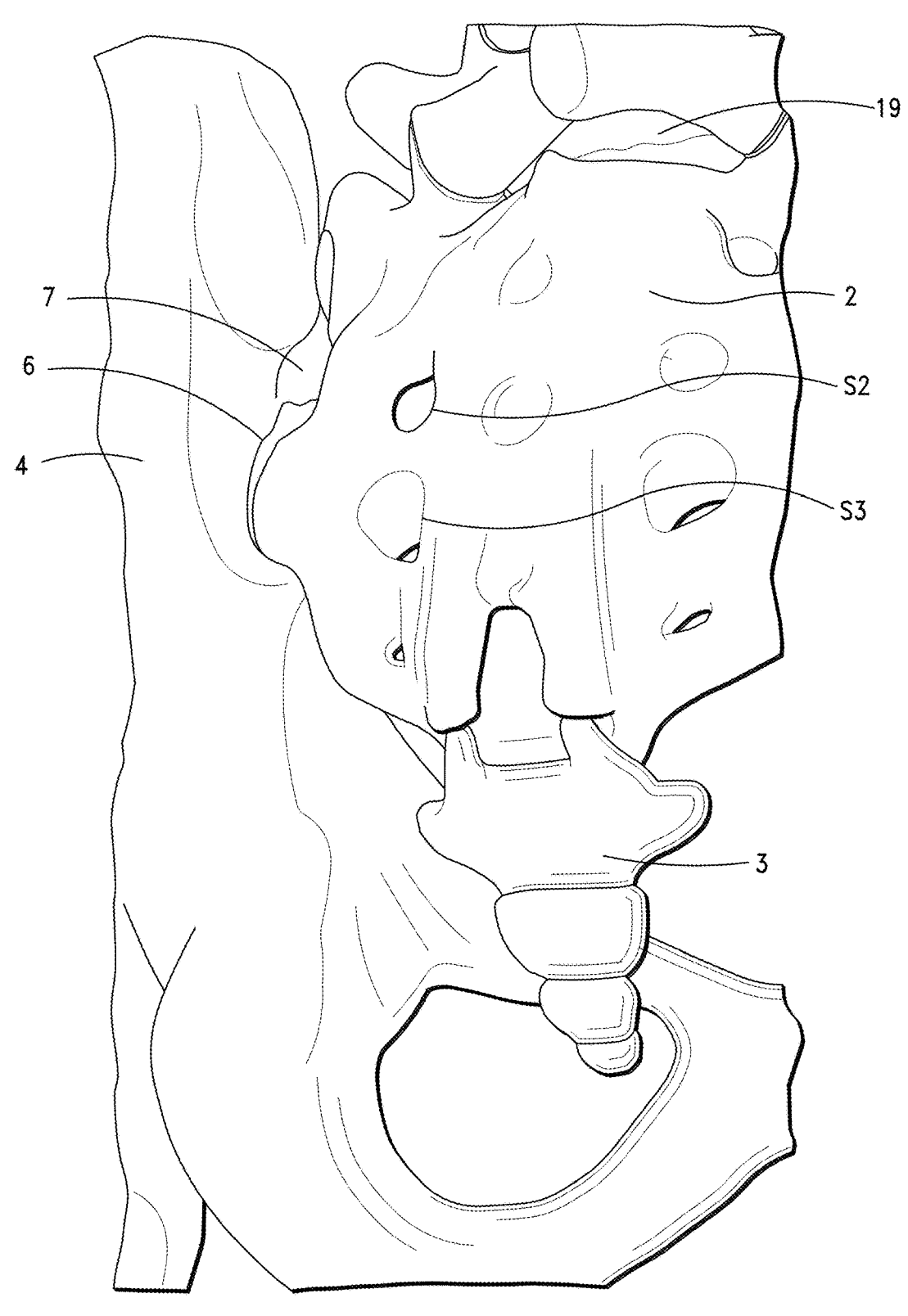
FIG. 1D is another schematic illustration of a human pelvic region from a posterior inferior perspective showing the adjoining sacrum and ilium bone structures of an SI joint, and an SI joint dorsal recess between the sacrum and ilium bone structures.

Before describing the present invention in detail, it is to be understood that this invention is not limited to particularly exemplified systems, apparatus, structures or methods as such may, of course, vary. Thus, although a number of systems apparatus and methods similar or equivalent to those described herein can be used in the practice of the present invention, the preferred systems, apparatus, structures and methods are described herein.

It is also to be understood that, although the present invention is described and illustrated in connection with sacroiliac (SI) joint stabilization, fixation and fusion procedures, the invention is not limited to such procedures. According to the invention, the systems, apparatus and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used in connection with a SI joint, means and includes a physiological abnormality, disorder or impairment of an SI joint, including, but limited to, traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "articular surface" and "articulating surface" are used interchangeably herein in connection with bone structures; particularly, the sacrum and ilium bone structures, and mean and include a surface of a bone structure that forms an articulating junction (i.e., a synovial joint) with an adjacent bone structure, e.g., the articular surfaces of the sacrum and ilium bone structures.

The term "SI joint dorsal recess", as used herein, means and includes a recess or space between the sacrum and ilium bone structures proximate the S2 segment region of the sacrum.

The terms "fusion" and "arthrodesis" are used inter-changeably herein in connection with bone structures, and mean and include partial or complete immobilization of adjacent bone structures; particularly, the sacrum and ilium bone structures.

The term "stabilization", as used herein, means and includes reinforcing, e.g., supporting, or modulating motion of adjacent articular bone structures; particularly, the sacrum and ilium bone structures. The term "stabilization", thus, in some instances, means and includes fusion and arthrodesis of adjacent bone structures.

The term "prosthesis", as used herein in connection with bone structures, means and includes a system or apparatus configured and adapted to stabilize or modulate motion of articulating bone structures; particularly, the sacrum and ilium bone structures.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly(lactic-co-glycolic) acid (PLGA) and poly($\epsilon$-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly(polyol sebacate) (PPS), poly(xylitol sebacate) (PXS), poly(xylitol glutamate sebacate) (PXGS), hydroxybutyrate-hydroxyvalerate copolymers, polyesters such as, but not limited to, aspartic acid and different aliphatic diols; poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly($\gamma$-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and Octyl-Seal); poly(ethylene glycol) (PEG) based compositions, including Focal Seal®, Progel™ Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly(ethylene glycol) (PGS-PEG); and/or composites thereof, e.g., PGS-hydroxyapatite (HA) composites and PGS-poly($\epsilon$-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)) and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-$\beta$ (TGF-$\beta$), including, TGF-$\beta$1 and TGF-$\beta$2; a growth hormone (GH), parathyroid hormone (PTH, including PTH1-34), transforming growth factor-$\alpha$ (TGF-$\alpha$), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2) and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs) and embryonic stem cells.

The terms "biologically active agent" and "biologically active composition" also mean and include an "extracellular vesicle (EV)", "exosome", "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab; disease-modifying anti-rheumatic drugs (DMARDs), including methotrexate and hydroxychloroquine; antibiotics, anti-viral agents, steroidal anti-inflammatories, non-steroidal anti-inflammatories, anti-thrombotic agents, including anti-coagulants and anti-platelet agents; and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®) and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to minimally-invasive systems, apparatus and methods for stabilizing dysfunctional SI joints.

In some embodiments of the invention, there are thus provided minimally-invasive systems for stabilizing dysfunctional SI joints.

As discussed in detail herein, the minimally-invasive systems (also referred to herein as "minimally-invasive SI joint stabilization systems") are configured and adapted to stabilize dysfunctional SI joints via a posterior approach.

As indicated above, SI joint stabilization, including minimally-invasive SI joint stabilization, typically comprises surgical placement of a SI joint prosthesis proximate to or in a dysfunctional SI joint via anterior, lateral and posterior approaches to the SI joint.

From the perspective of FIG. 1A, an anterior approach to the SI joint 6 (and, hence, a dysfunctional SI joint) would be substantially perpendicular to the page upon which FIG. 1A is printed.

Figure 1E:
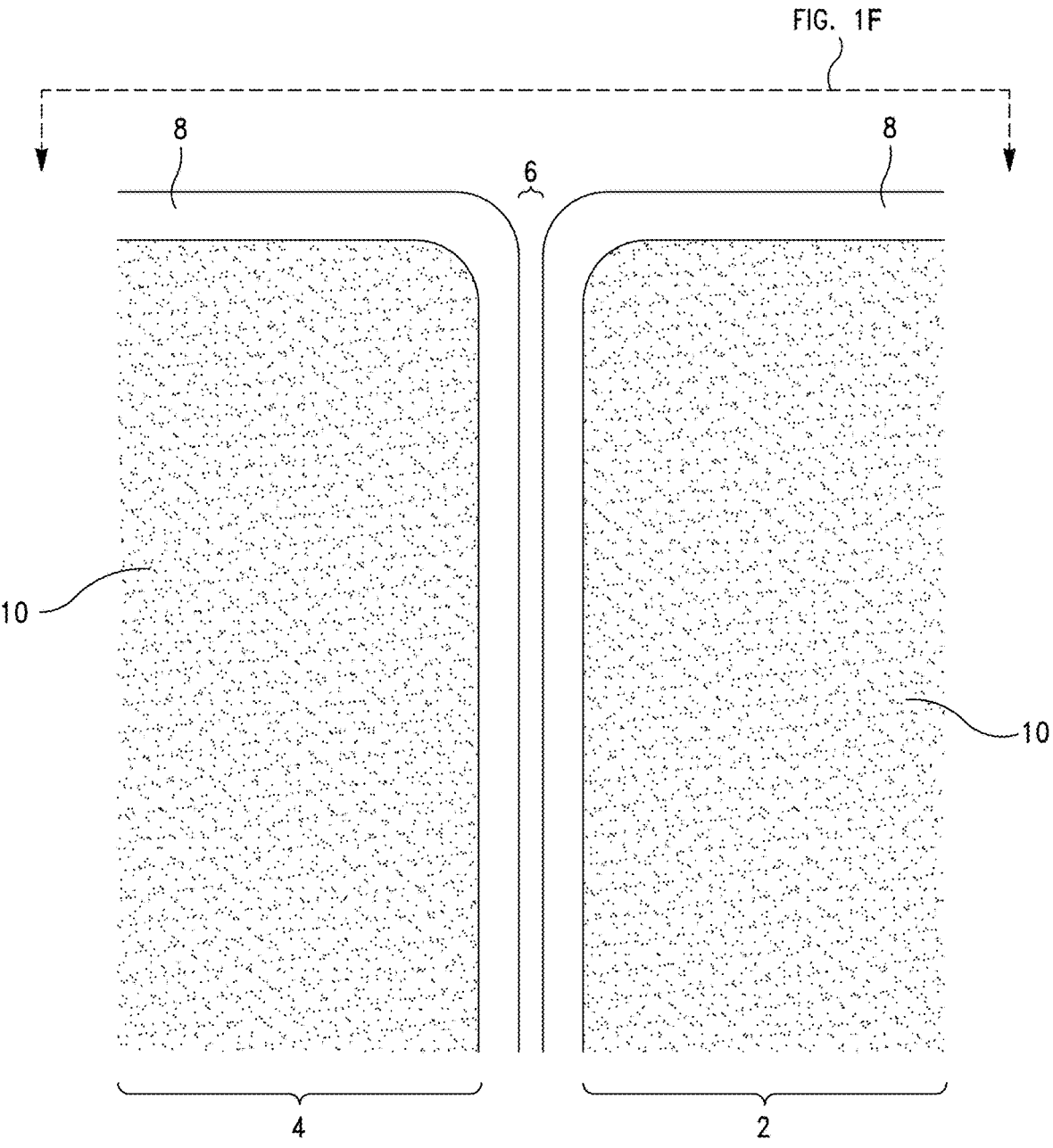
FIG. 1E is an illustration of a SI joint from a superior perspective showing the adjoining sacrum and ilium articular surfaces.

Referring now to FIG. 1E there is shown an illustration of a SI joint 6 and surrounding structures. For illustrative simplicity, a uniform layer of cortical bone 8 is shown adjacent a deeper layer of trabecular bone 10 on both of the depicted sacrum 2 and ilium 4 structures. However, in actuality, such layers are far less uniform and homogeneous.

Figure 1F:
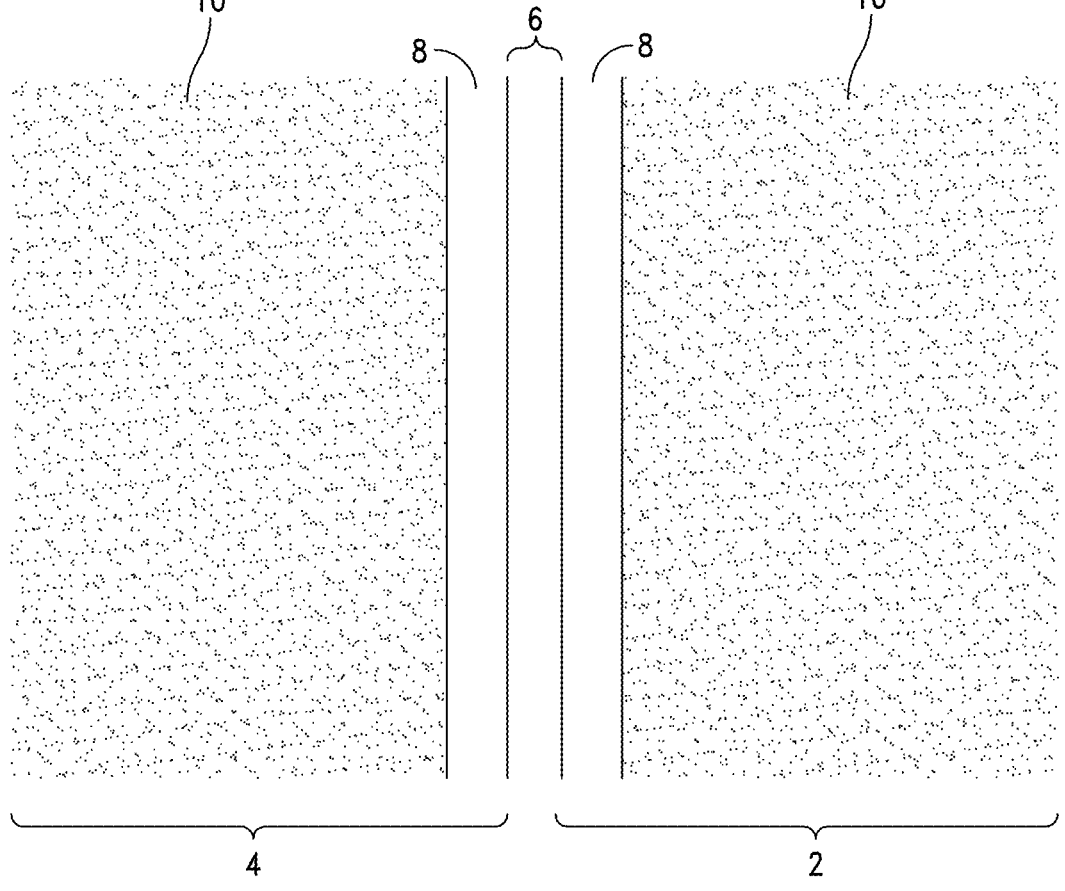
FIG. 1F is another illustration of a SI joint from a posterior perspective showing the adjoining sacrum and ilium articular surfaces.
Figure 1G:
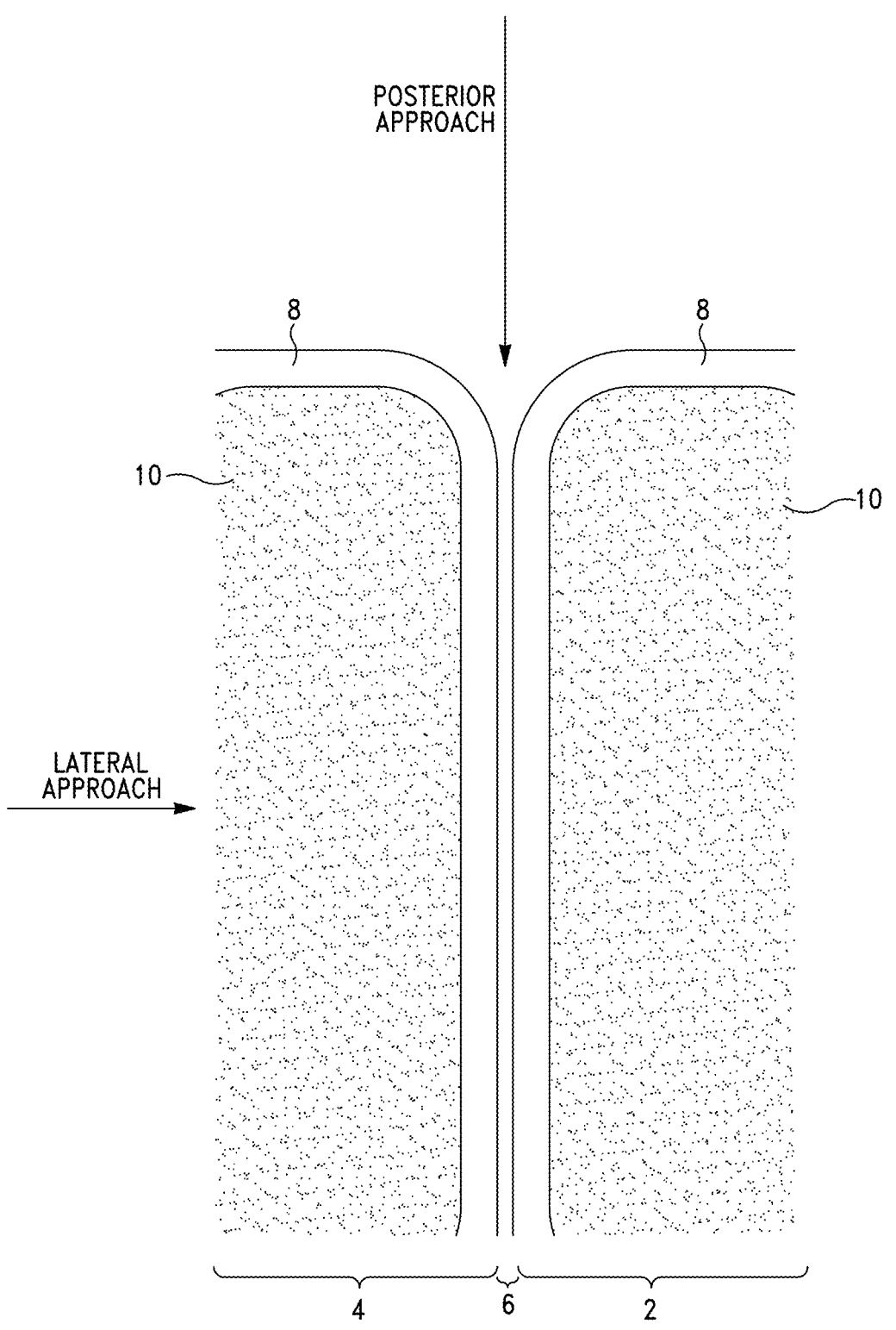
FIG. 1G is a further illustration of the SI joint shown in FIG. 1F showing lateral and posterior approaches to the SI joint, in accordance with the invention.

Referring now to FIG. 1F, there is shown a view of the same structure from a different posterior perspective. From the perspective of FIG. 1F, a posterior approach to the SI joint 6 (and, hence, a dysfunctional SI joint) would be substantially perpendicular to the page upon which FIG. 1F is printed. Indeed, referring to FIG. 1G, a variation similar to that depicted in FIG. 1E is illustrated, showing an approximate approach vector for a lateral approach to the SI joint 6 versus a posterior approach, using the orientation paradigms introduced in FIGS. 1A and 1F-1G. Such paradigms are used to illustrate various embodiments of the subject invention in various figures that follow FIGS. 1A and 1F-1G.

As indicated above, a major disadvantage associated with many conventional anterior or lateral approaches to a dysfunctional SI joint is that muscles and ligaments are typically disrupted and often damaged. Nerves and blood vessels are also susceptible to damage during such SI joint stabilization methods.

In contrast, posterior approaches to a dysfunctional SI joint; particularly, the posterior approach employing the minimally-invasive SI joint stabilization systems of the invention described herein, are much less invasive. Indeed, less tissue and fewer muscles are disrupted, and nerves and large blood vessels are avoided.

In a preferred embodiment of the invention, the SI joint stabilization systems of the invention generally comprise (i) a tool assembly configured and adapted to access the target dysfunctional SI joint via a posterior approach and create at least one pre-determined opening in the dysfunctional SI joint (referred to herein after as a "pilot SI joint opening"), (ii) a SI joint prosthesis configured and adapted to be inserted into the pilot SI joint opening created by the tool assembly, and (iii) a prosthesis deployment assembly configured and adapted to engage the SI joint prosthesis and advance the SI joint prosthesis into the dysfunctional SI joint.

Tool Assemblies

In a preferred embodiment of the invention, the tool assembly comprises an elongated guide pin (referred to as a "guide probe" in Co-pending U.S. application Ser. No. 17/463,779) and a drill guide assembly.

Figures 2A, 2B:
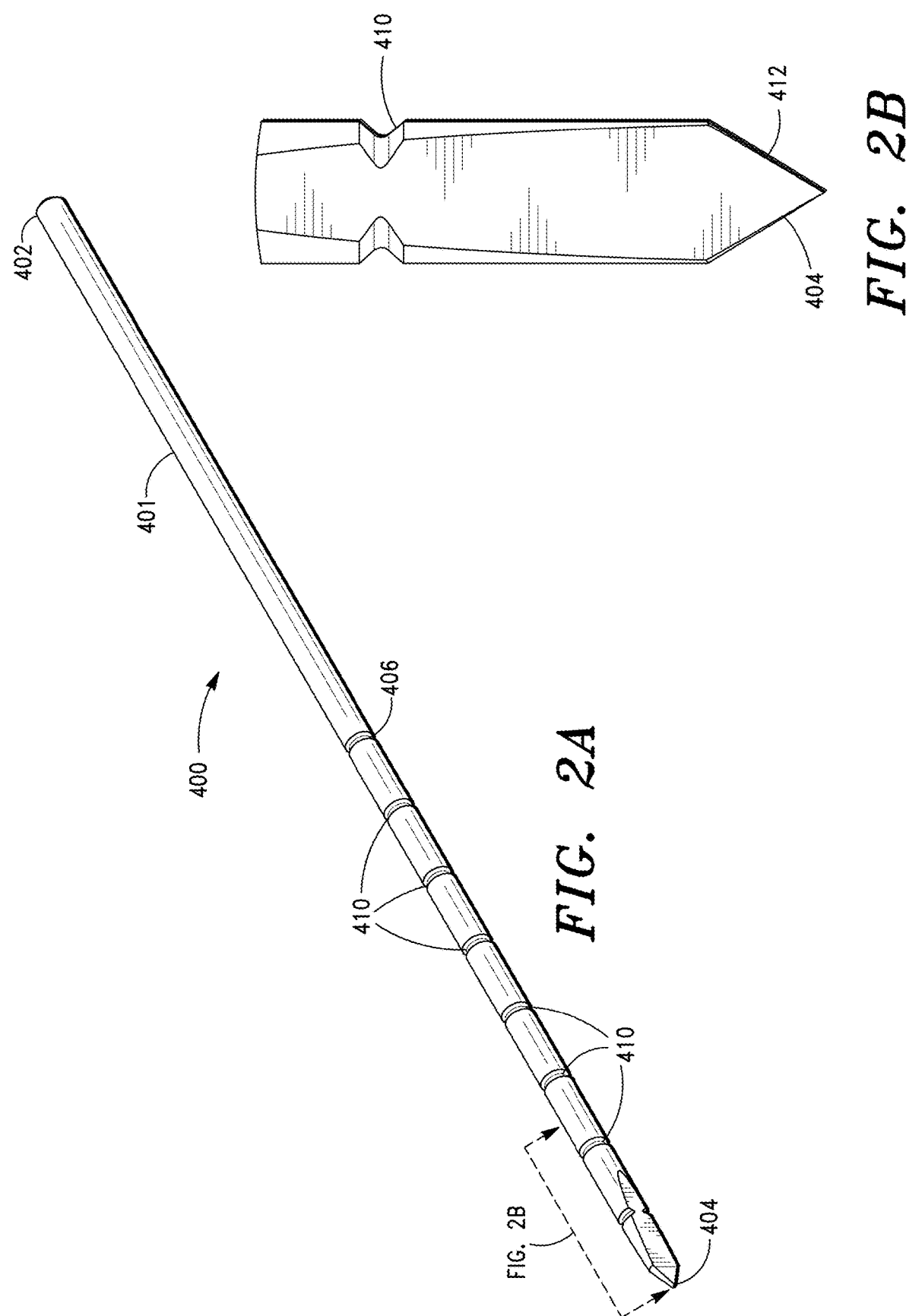
FIG. 2A is a perspective view of one embodiment of a guide pin, in accordance with the invention.
FIG. 2B is a partial side plan view of the guide pin shown in FIG. 2A showing a guide pin marking, in accordance with the invention.

Referring now to FIG. 2A, there is shown a preferred embodiment of a guide pin of the invention (denoted "400").

As discussed in detail below, the guide pin 400 is sized and configured to be positioned in a dysfunctional SI joint and, when positioned therein, function as (i) a guide for the drill guide assembly, i.e. drill guide thereof, and, thereby, positioning of the pilot SI joint opening(s) created by the drill guide assembly, (ii) a landmark for the SI joint prosthesis to be disposed in the dysfunctional SI joint, and (iii) in some embodiments, a guide for the prosthesis deployment assembly and, hence, SI joint prosthesis engaged thereto into the pilot SI joint opening created by the drill guide assembly and, thereby, positioning of the SI joint prosthesis in the dysfunctional SI joint.

As illustrated in FIG. 2A, the guide pin 400 comprises an elongated graduated wire or rod structure 401 comprising proximal and distal ends 402, 404 and a plurality of spaced guide pin markings 410 that extend from the distal end 404 of the guide pin 400 to preferably at least the mid-region 406 of the guide pin 401.

According to the invention, the guide pin markings 410 can comprise various distinguishable surface markings, symbols, lines and/or structural patterns and arrangements, which preferably are readily detectable and, hence, readable via a conventional image capture apparatus, such as a fluoroscope and radiography system.

As illustrated in FIG. 2B, in a preferred embodiment of the invention, the guide pin markings 410 comprise a plurality of graduated or spaced grooves or depressions in the wire structure 401. According to the invention, any number of spaced grooves, i.e., markings 410, can be employed on the wire structure 401 and, hence, guide pin 400 and can be spaced apart at any desired dimension.

As illustrated in FIG. 2A, in a preferred embodiment of the invention, the guide pin 400 includes eight (8) grooves, i.e., markings 410, which are uniformly spaced 10.0 mm apart.

As further illustrated in FIGS. 2A and 2B, in a preferred embodiment, the distal end 404 of the guide pin 400 comprises a pointed configuration 412 to facilitate entry of the distal end 404 of the guide pin 400 into and through tissue, articular cartilage and SI joint bone structures.

Figure 3A:
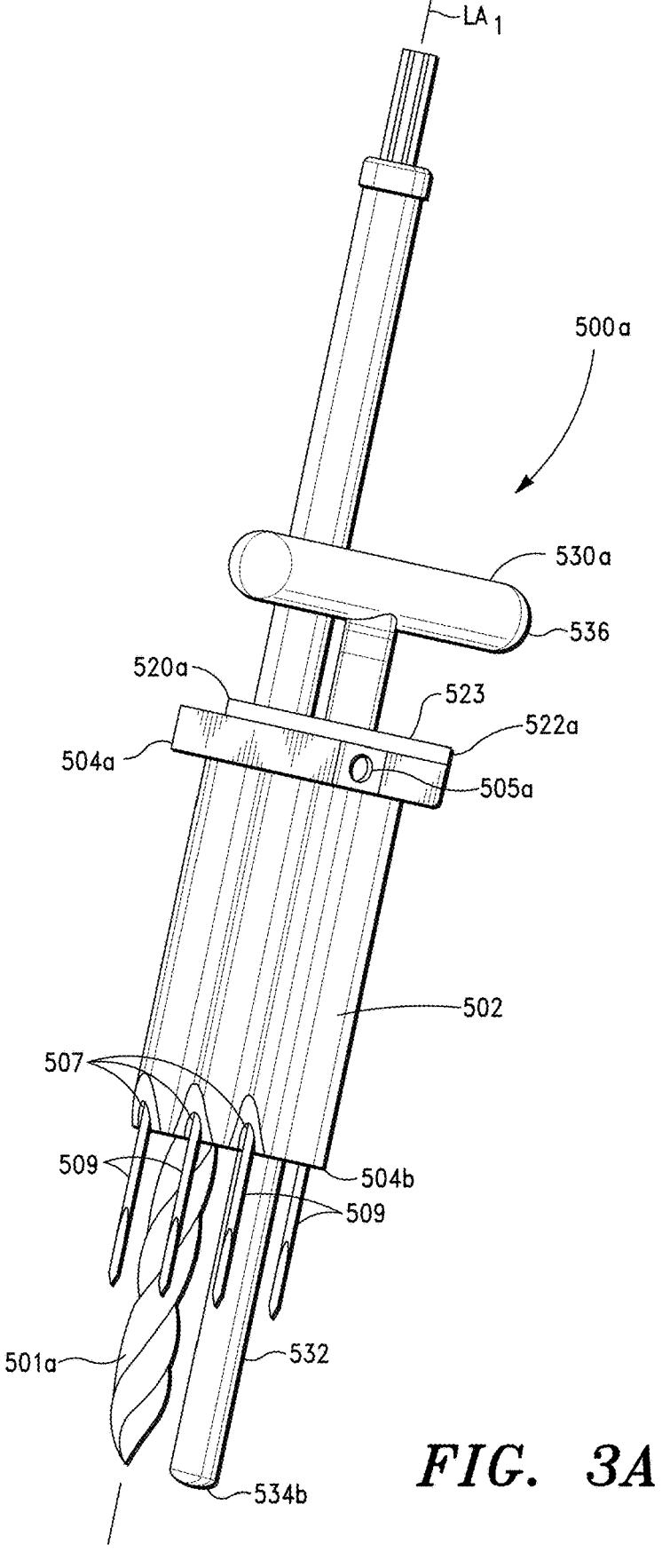
FIG. 3A is a perspective view of one embodiment of a drill guide assembly, in accordance with the invention.

Referring now to FIG. 3A, there is shown one embodiment of a drill guide assembly 500a of the invention.

According to the invention, the drill guide assembly 500a is configured and adapted to create pre-determined pilot SI joint openings in a SI joint, including a dysfunctional SI joint, to accommodate placement of a SI joint prosthesis of the invention therein.

As illustrated in FIG. 3A, the drill guide assembly 500a generally comprises an access sleeve 502, a drill guide 520a, a bone dislodging apparatus 501a, and a drill alignment pin 530a.

Figure 6A:
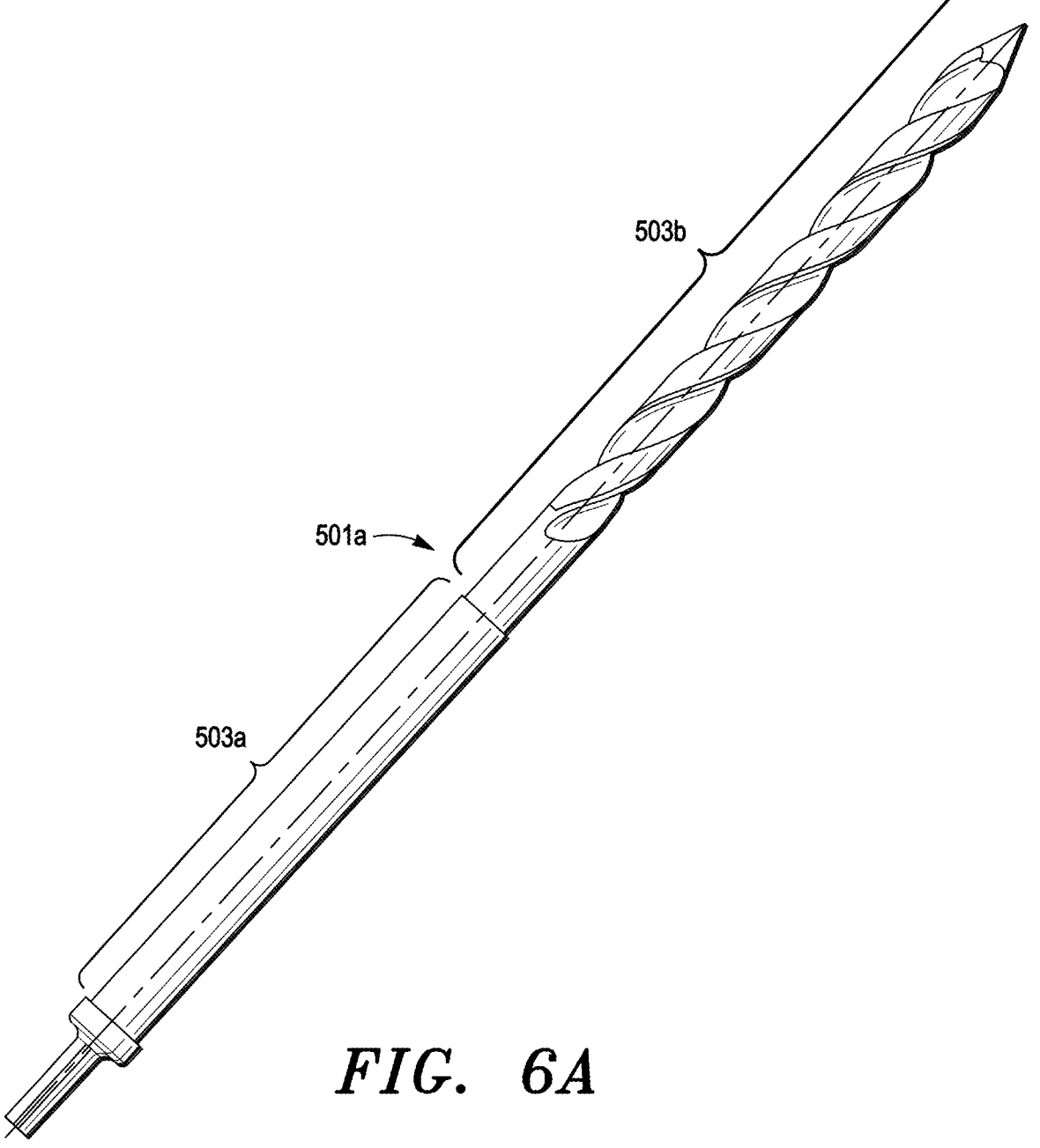
FIG. 6A is a perspective view of one embodiment of a bone dislodging apparatus, i.e., drill bit, in accordance with the invention.

As further illustrated in FIGS. 3A and 6A, the bone dislodging apparatus preferably comprises a conventional drill bit 501*a*, comprising an elongated rod or shaft structure having a proximal end region 503*a* and a bone dislodging end region 503*b*.

Referring now to FIGS. 3B-3D, there is shown one embodiment of the access sleeve 502.

As discussed in detail in Co-pending U.S. application Ser. No. 17/463,779 and illustrated in FIGS. 3B-3D, the access sleeve 502 comprises proximal and distal ends 504*a*, 504*b*, an internal opening 506 that extends from the proximal end 504*a* to the distal end 504*b* of the access sleeve 502, and a plurality of lumens 507, which, as illustrated in FIG. 3A, are sized and configured to receive and position Kirschner wires (K-wires) 509 or similar pin structures therein.

As further illustrated in FIG. 3A, in a preferred embodiment, the access sleeve internal opening 506 is sized and configured to receive and position the drill guide 520*a* therein.

As further illustrated in FIGS. 3B and 3D, the proximal end 504*a* of the access sleeve 502 comprises a planar region 503, which, as illustrated in FIG. 3A, is configured to seat the proximal end 522*a* of the drill guide 520*a* (discussed below) thereon.

In a preferred embodiment, as additionally shown in FIGS. 3B and 3D, the proximal end 504*a* of the access sleeve 502, i.e., planar region 503, further comprises two (2) threaded holes 505*a*, 505*b*, which are preferably disposed on opposing edge regions of the planar region 503.

According to the invention, the threaded holes 505*a*, 505*b* are sized and configured to receive the threaded end 514 of the access sleeve handle 510*a*, discussed below.

Figures 3E, 3F:
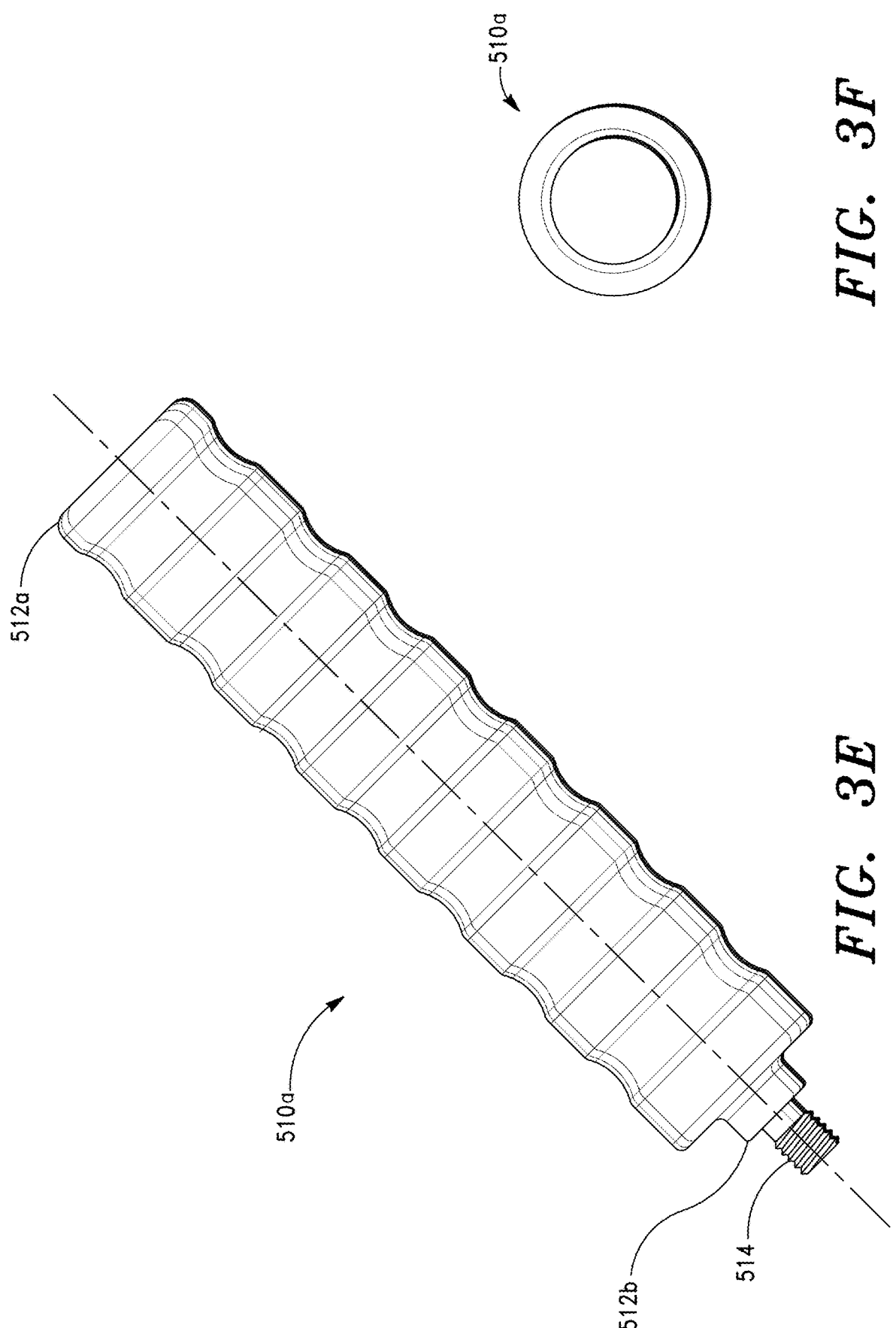
FIG. 3E is a perspective view of one embodiment of an access sleeve handle that is configured to engage the access sleeve shown in FIG. 3B, in accordance with the invention.
FIG. 3F is an end plan view of the access sleeve handle shown in FIG. 3E, in accordance with the invention.
Figure 3H:
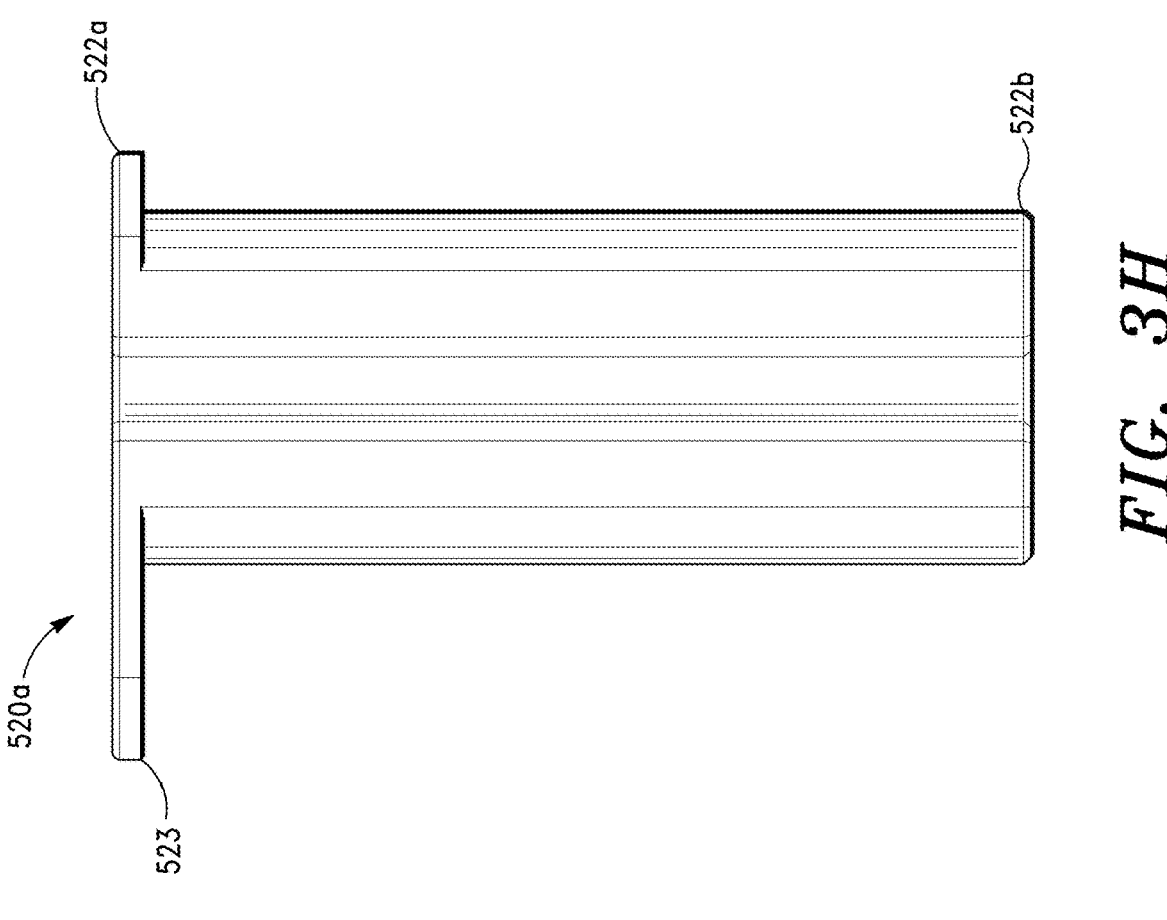
FIG. 3H is a front plan view of the drill guide shown in FIG. 3G, in accordance with the invention.
Figure 3G:
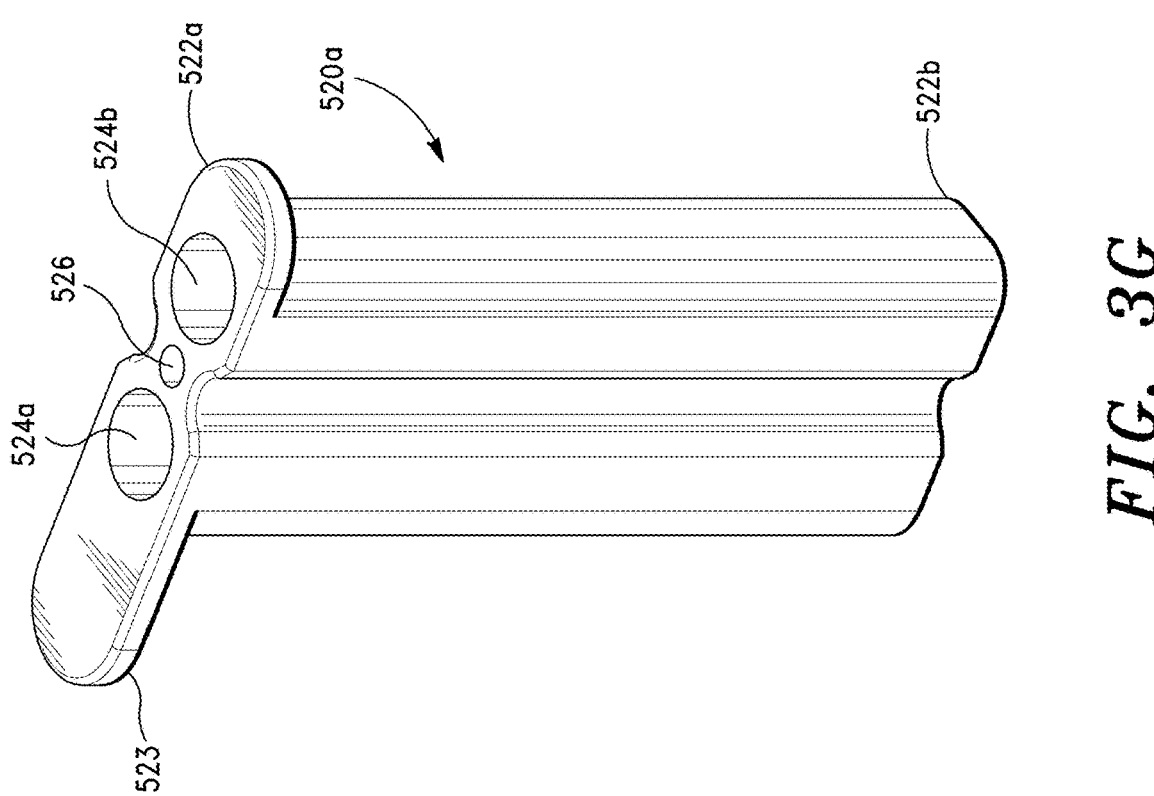
FIG. 3G is a perspective view the drill guide of the drill guide assembly shown in FIG. 3A, in accordance with the invention.
Figure 3I:
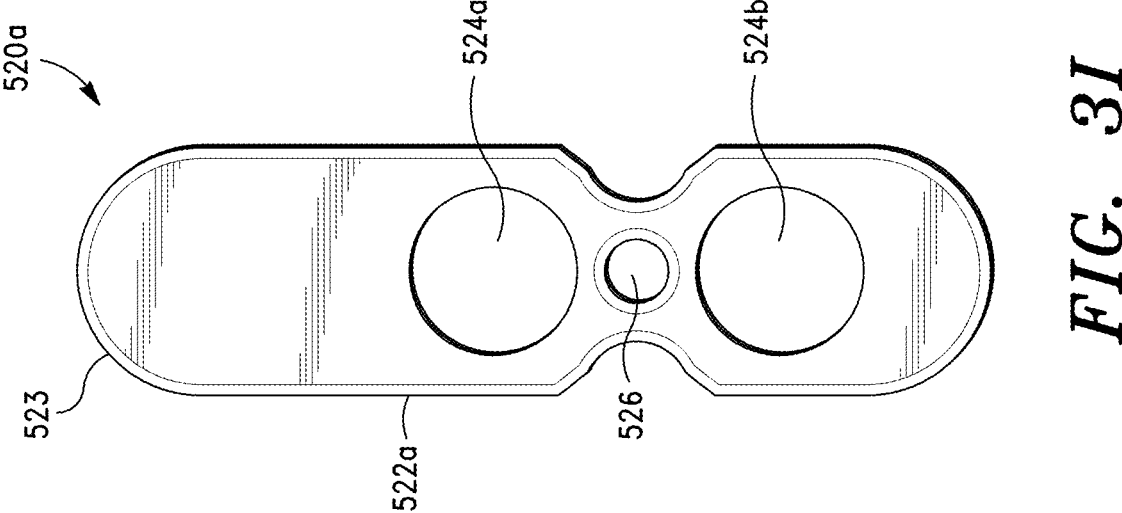
FIG. 3I is a top plan view of the drill guide shown in FIG. 3G, in accordance with the invention.
Figure 3J:
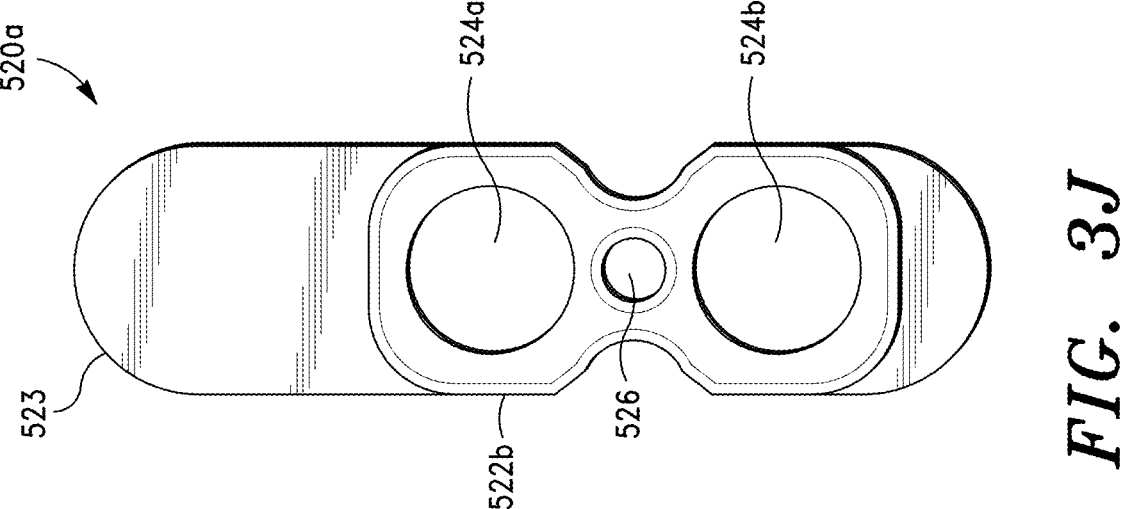
FIG. 3J is a bottom plan view of the drill guide shown in FIG. 3G, in accordance with the invention.

Referring now to FIGS. 3E and 3F, there is shown a preferred embodiment of the access sleeve handle 510*a*.

As illustrated in FIGS. 3E and 3F, the handle 510*a* preferably comprises an elongated cylindrical shaped member comprising proximal and distal ends 512*a*, 512*b*.

As further illustrated in FIG. 3E, in a preferred embodiment, the distal end 512*b* of the handle 510*a* comprises a threaded extension 514 that is sized and configured to cooperate with the threaded holes 505*a*, 505*b* of the access sleeve 502 (and threaded holes 511*a*, 511*b* of the drill guide 520*b*, drill guide 520*c* or drill guide 520*d*), whereby the access sleeve handle 510*a* can be threadably engaged to the access sleeve 502 (or drill guides 520*b*, 520*c*, 520*d*).

Referring now to FIGS. 3G-3J, there is shown one embodiment of a drill guide 520*a* of the invention.

As illustrated in FIGS. 3G-3J, the drill guide 520*a* comprises proximal and distal ends 522*a*, 522*b*, a pair of drill guide lumens 524*a*, 524*b*, and a drill guide medial lumen 526; the drill guide lumens 524*a*, 524*b* and drill guide medial lumen 526 extending from the proximal end 522*a* to the distal end 522*b* of the drill guide 520*a*.

As illustrated in FIG. 3A, in a preferred embodiment, the drill guide lumens 524*a*, 524*b* are sized and configured to receive (i) the bone dislodging apparatus of the invention 501*a*, in this instance, a drill bit, such as shown in FIGS. 3A and 6A, and (ii) the drill alignment pin 530*a* shown in FIG. 3K, and discussed below.

As set forth in Co-pending U.S. application Ser. No. 17/463,779, according to the invention, the drill bit 501*a* (and drill bits 501*b*, 501*c* shown in FIGS. 6B and 6C, respectively) can operate with various conventional manual, pneumatic, and/or electromechanical tools, such as a conventional surgical drill.

Figure 3K:
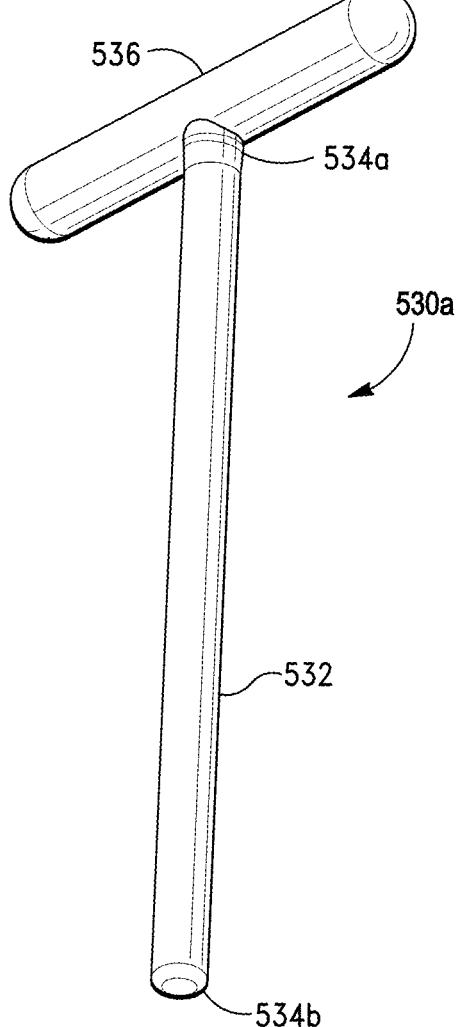
FIG. 3K is a perspective view of the embodiment of the drill alignment pin of the drill guide assembly shown in FIG. 3A, in accordance with the invention.

As illustrated in FIG. 3K, the drill alignment pin 530*a* preferably comprises an elongated guide member 532 comprising proximal and distal ends 534*a*, 534*b*. The drill alignment pin 530*a* further comprises a handle 536 that is in communication with the proximal end 534*a* of the guide member 532.

In a preferred embodiment, the drill guide medial lumen 526 is sized and configured to receive and guide the guide pin 400 of the invention.

According to the invention, the drill guide internal lumens 524*a*, 524*b* and drill guide medial lumen 526 can also be sized and configured to receive various other suitable instruments, such as surgical scopes, center punches, location pins, drill probes and drill stop assemblies, to facilitate the creation of a pilot SI joint opening.

Referring back to FIGS. 3G and 3H, in a preferred embodiment, the proximal end 522*a* of the drill guide 520*a* comprises a planar configuration comprising an extended region 523, which, as illustrated in FIG. 3A, is sized and configured to abut the proximal end 504*a* of the access sleeve 502 to position the drill guide 520*a* therein.

Figure 4A:
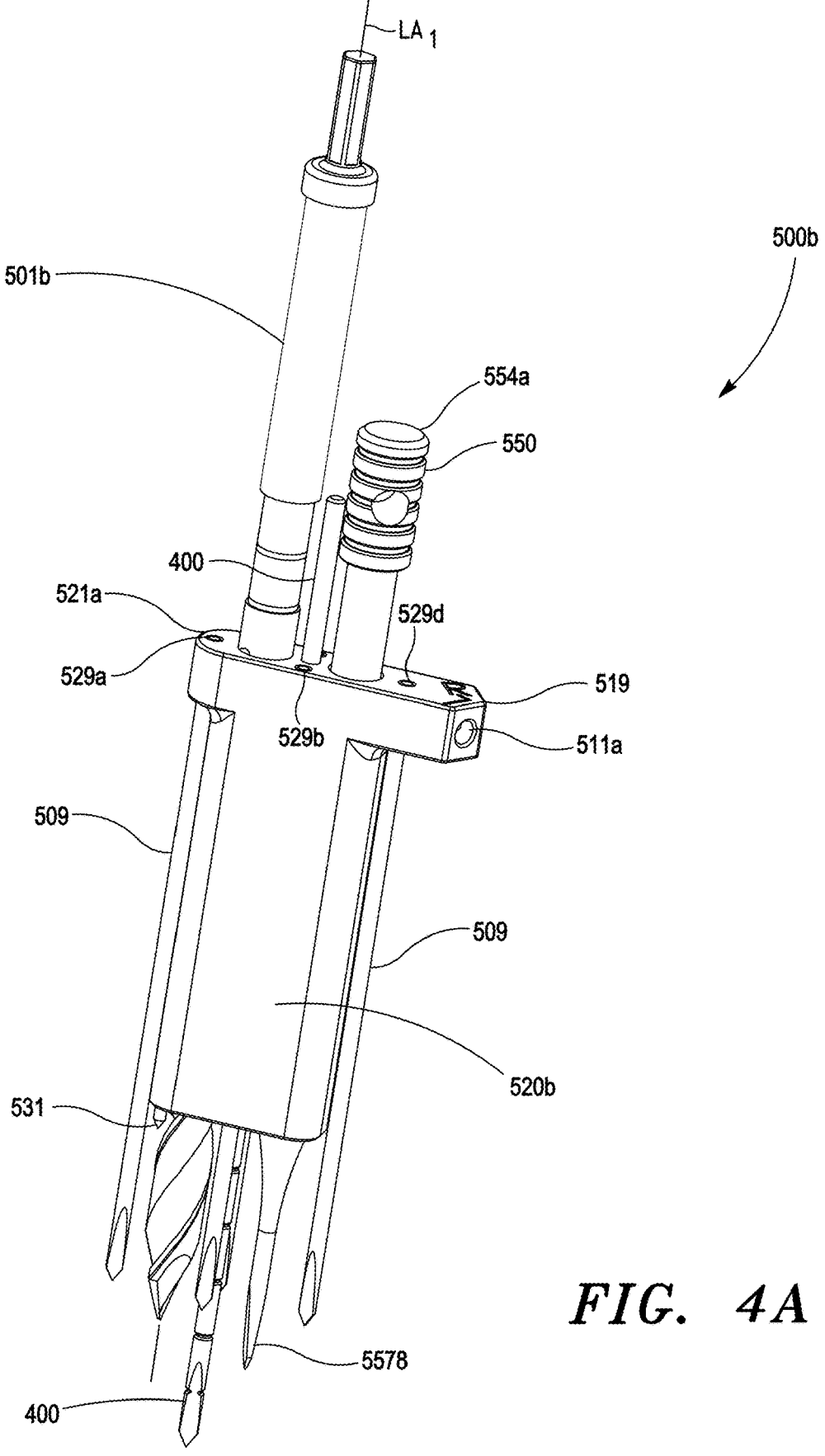
FIG. 4A is a perspective view of another embodiment of a drill guide assembly comprising another embodiment of the drill guide having a bone dislodging apparatus and a K-wire pin member disposed in the internal lumens thereof, in accordance with the invention.
Figure 4B:
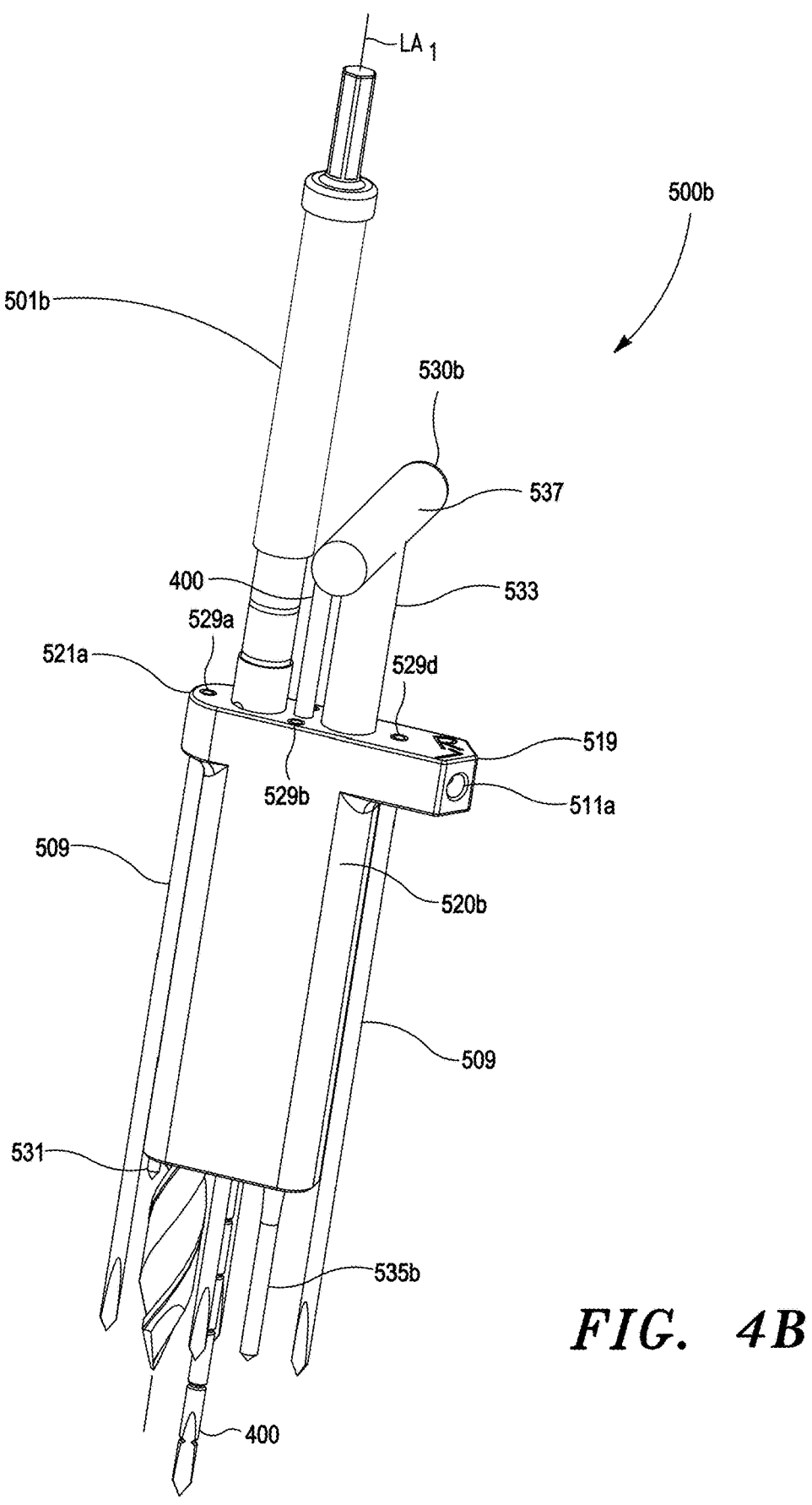
FIG. 4B is a perspective view of the drill guide assembly shown in FIG. 4A comprising the bone dislodging apparatus and a temporary fixation pin disposed in the internal lumens of the drill guide, in accordance with the invention.

Referring now to FIGS. 4A and 4B, there is shown another embodiment of a drill guide assembly of the invention (denoted "500*b*").

Figure 4D:
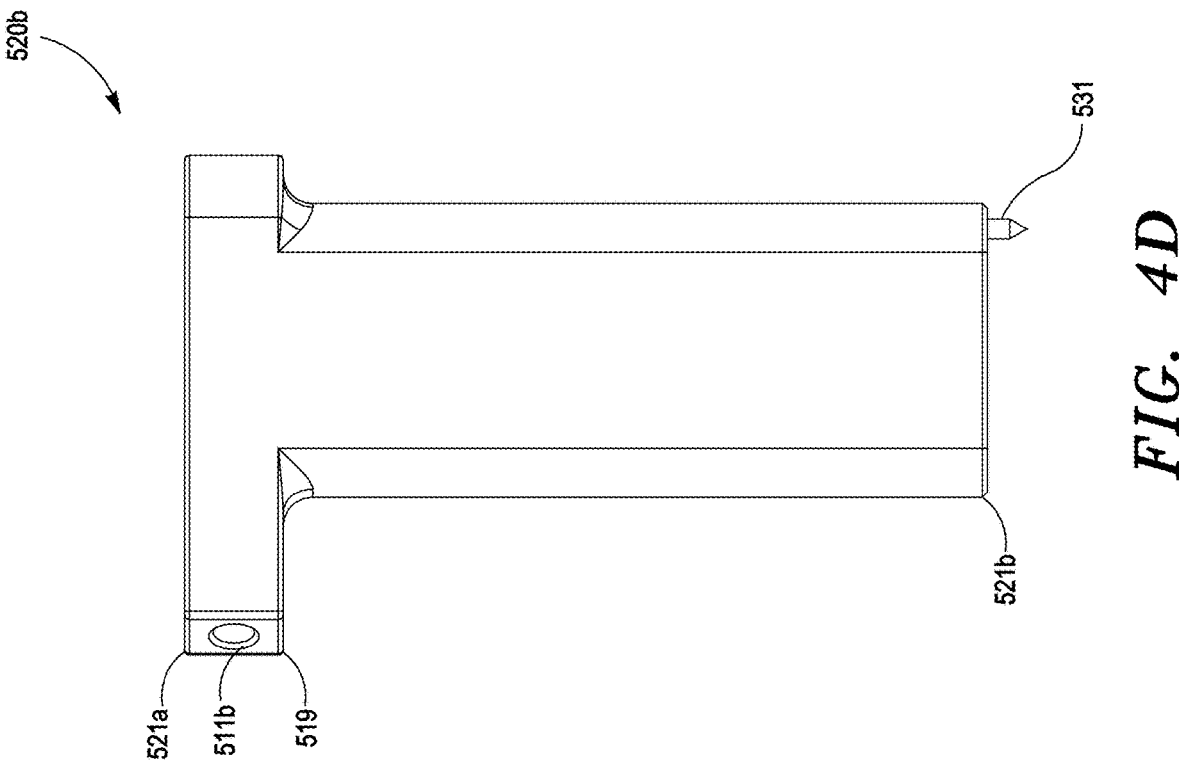
FIG. 4D is a right-side plan view of the drill guide shown in FIG. 4C, in accordance with the invention.
Figure 4C:
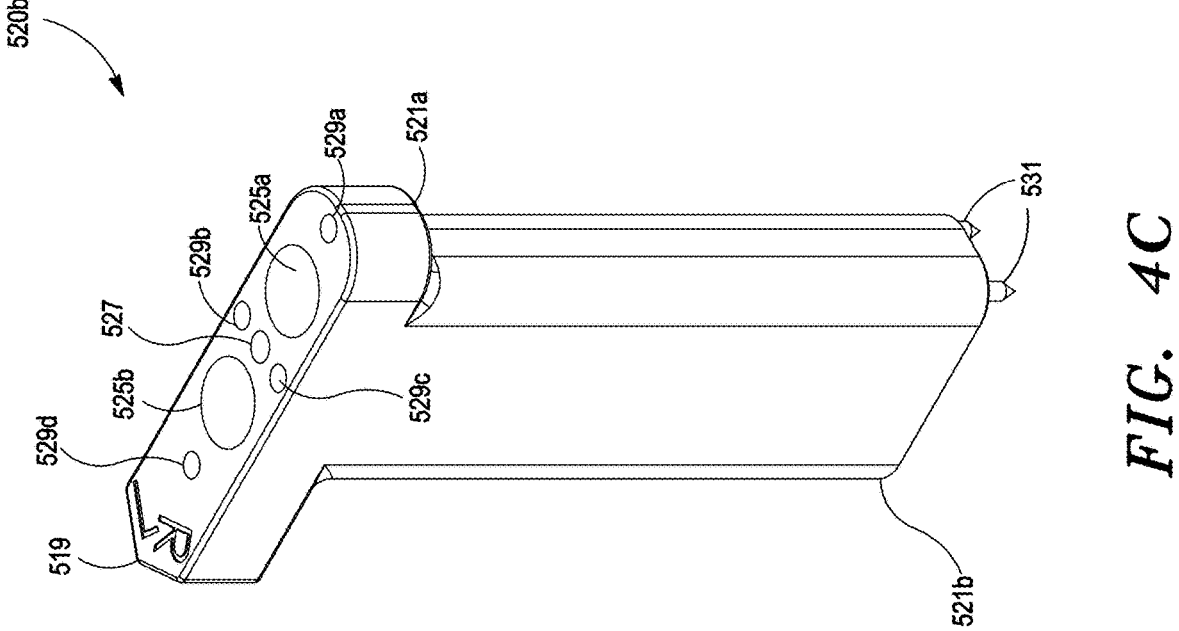
FIG. 4C is a rear perspective view of the drill guide of the drill guide assembly shown in FIGS. 4A and 4B, in accordance with the invention.
Figure 4F:
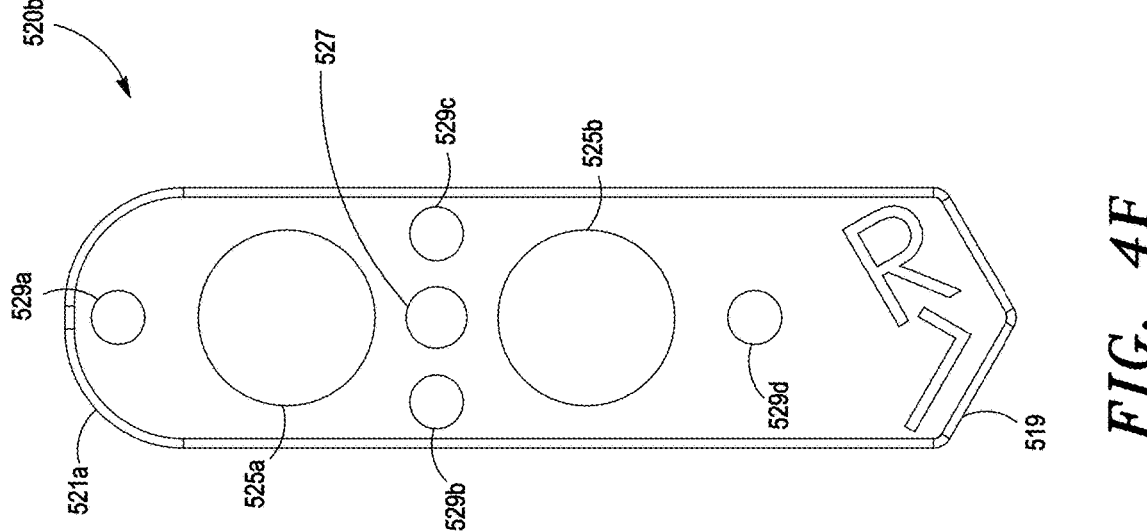
FIG. 4F is a top plan view of the drill guide shown in FIG. 4C, in accordance with the invention.
Figure 4E:
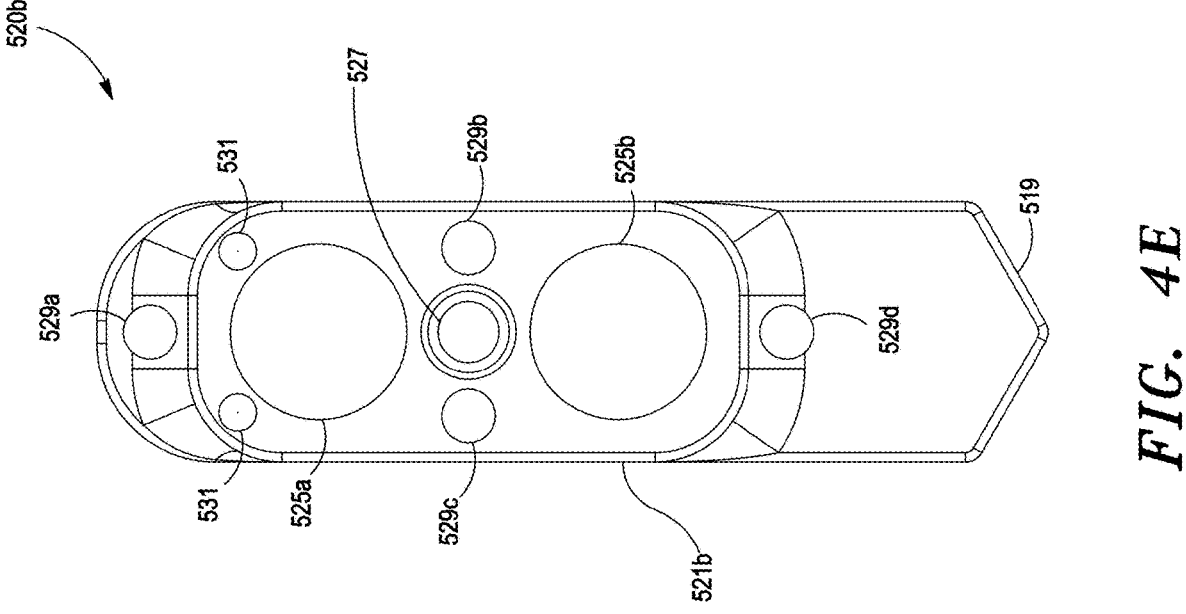
FIG. 4E is a bottom plan view of the drill guide shown in FIG. 4C, in accordance with the invention.
Figure 4H:
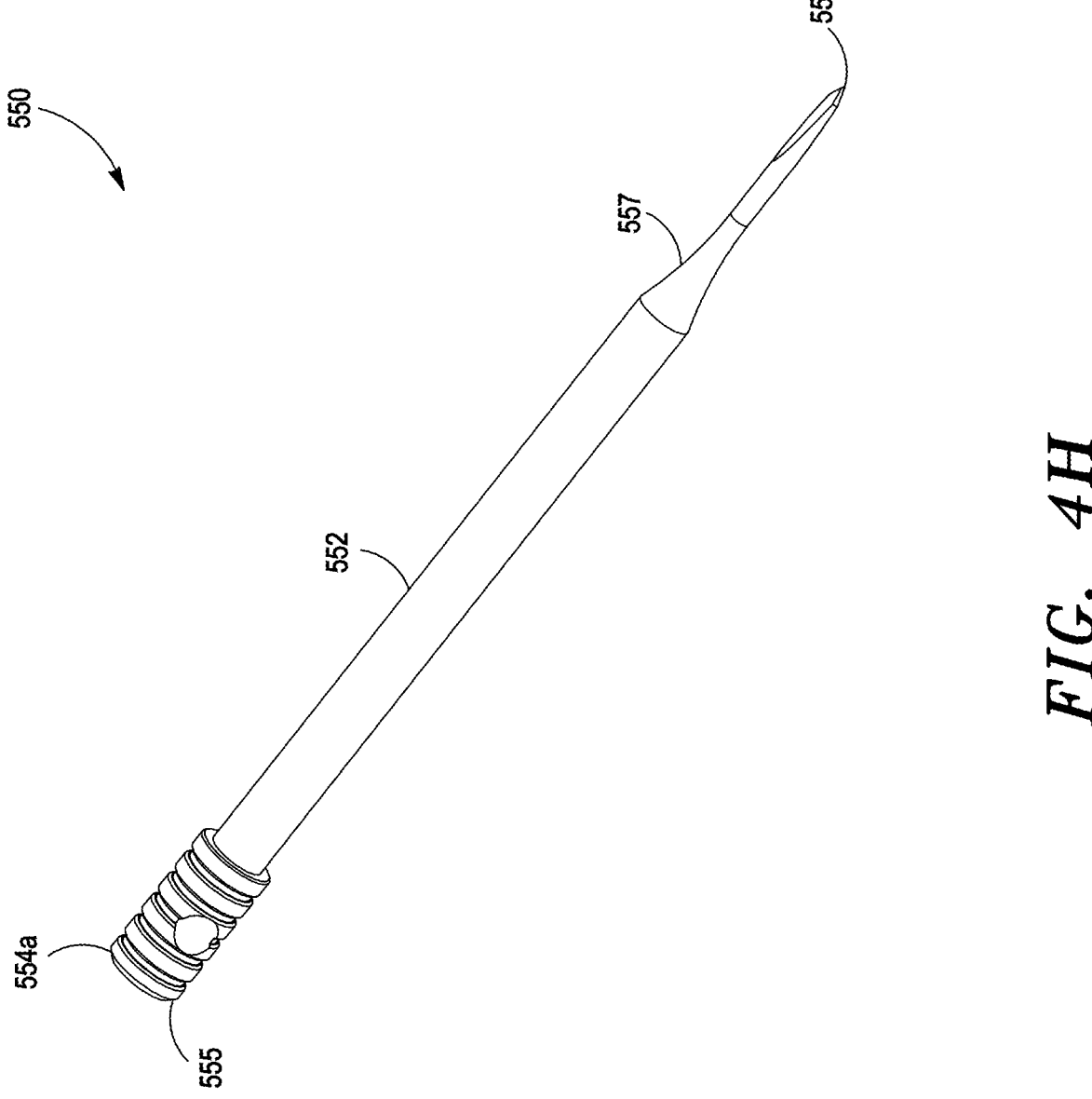
FIG. 4H is a perspective view of the K-wire member of the drill guide assembly shown in FIG. 4A, in accordance with the invention.
Figure 4I:
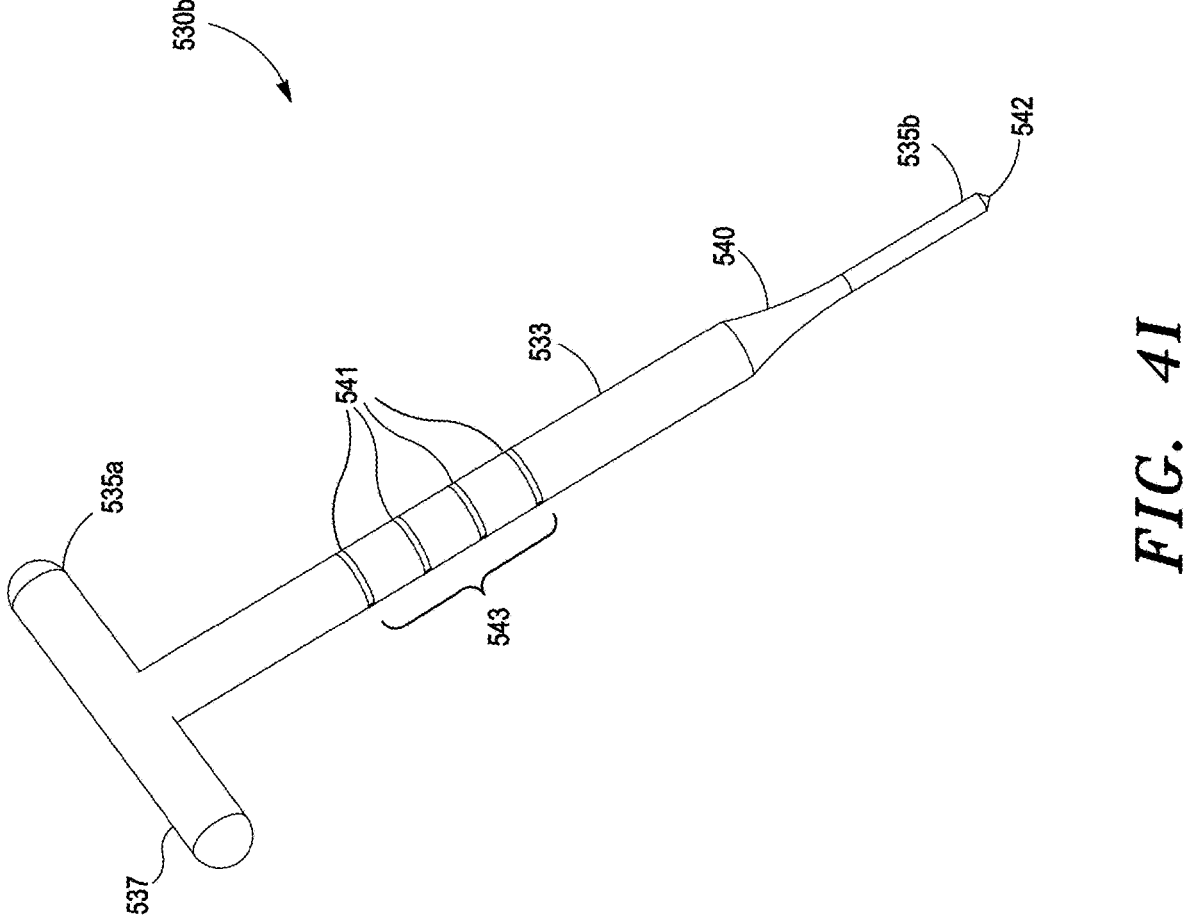
FIG. 4I is a perspective view of the temporary fixation pin of the drill guide assembly shown in FIG. 4B, in accordance with the invention.

As illustrated in FIGS. 4A and 4B, the drill guide assembly 500*b* generally comprises a drill guide 520*b*, a bone dislodging apparatus; preferably, drill bit 501*b*, a K-wire pin member 550, which is shown in FIG. 4H, and a drill alignment pin 530*b* (referred to herein as a "temporary fixation pin"), which is shown in FIG. 4I.

Figure 6B:
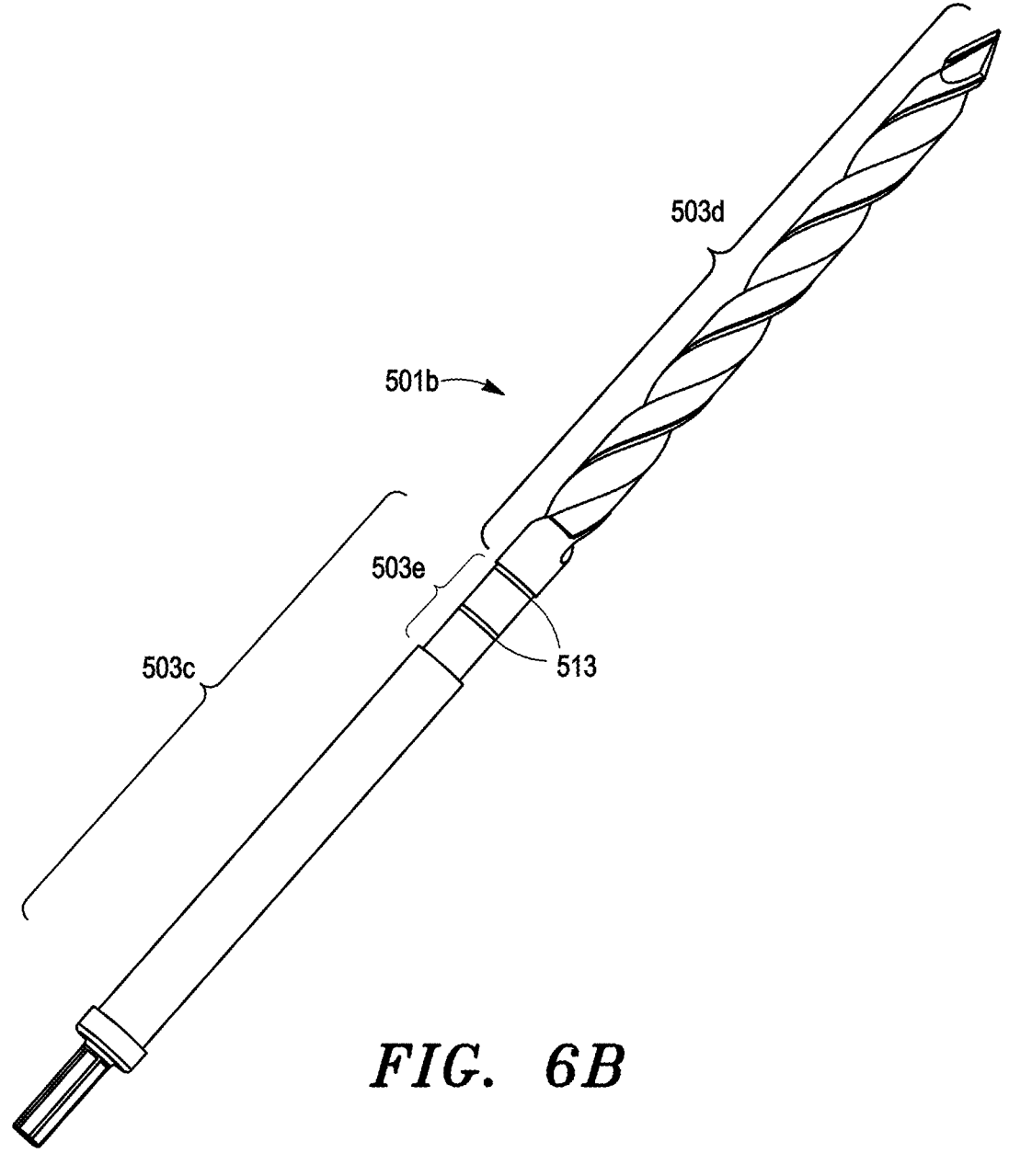
FIG. 6B is a perspective view of another embodiment of a bone dislodging apparatus, in accordance with the invention.

Referring to FIG. 6B, in a preferred embodiment, the drill bit 501*b* similarly comprises an elongated rod structure having a proximal end region 503*c* and a bone dislodging end region 503*d*. However, as illustrated in FIG. 6B, the proximal end region 503*c* comprises a plurality of graduated markings 513 disposed on the distal region 503*e* thereof.

In a preferred embodiment, the graduated markings 513 are spaced approximately 10 mm apart and, by virtue of unique configuration of the drill guide 520*b* and the location of the graduated markings 513, can be directly visualized and, hence, read during creation of pilot SI joint openings with the drill bit 501*b*.

The graduated markings 513 are also readily detectable and, hence, readable via a conventional image capture apparatus, such as a fluoroscope and radiography system.

According to the invention, the graduated markings 513 reflect predetermined depths of the drill bit 501*b* when the drill bit 501*b* is advanced into a bone structure, e.g., 50 mm, 60 mm, etc., during the bone dislodging process.

In a preferred embodiment, the graduated markings 513 are preferably laser etched into the drill bit 501*b*.

As illustrated in FIG. 6B, in a preferred embodiment, the diameter of the bone dislodging end region 503*d* is greater than the diameter of the distal region 503*e* of the proximal end region 503*c* of the drill bit 501*b* to prevent premature wear of the graduated markings 513 and, hence, compromised detection and readability of the markings 513 when the drill bit 501*b* is repeatedly advanced into and through bone structures.

Referring now to FIGS. 4C-4G, there is shown a preferred embodiment of the drill guide 520*b*.

As illustrated in FIGS. 4C-4G, the drill guide 520*b* comprises proximal and distal ends 521*a*, 521*b*, a pair of drill guide lumens 525*a*, 525*b*, four (4) K-wire lumens 529*a*, 529*b*, 529*c*, 529*d*, and a drill guide medial lumen 527; the drill guide lumens 525*a*, 525*b*, four (4) K-wire lumens 529*a*, 529*b*, 529*c*, 529*d*, and drill guide medial lumen 527 extending from the proximal end 521*a* to the distal end 521*b* of the drill guide 520*b*.

As illustrated in FIG. 4B, in a preferred embodiment, the drill guide lumens 525a, 525b are similarly sized and configured to receive (i) a bone dislodging apparatus of the invention, in this instance, drill bit 501b shown in FIG. 6B, and (ii) the temporary fixation pin 530b shown in FIG. 4I and discussed below.

As illustrated in FIG. 4A, in a preferred embodiment, the drill guide lumens 525a, 525b are also sized and configured to receive K-wire pin member 550 shown in FIG. 4H.

In a preferred embodiment, the drill guide medial lumen 527 is similarly sized and configured to receive and guide the guide pin 400 of the invention.

According to the invention, the drill guide lumens 525a, 525b and drill guide medial lumen 527 can similarly also be sized and configured to receive various other suitable instruments, such as surgical scopes, center punches, location pins, drill probes, and drill stop assemblies, to facilitate the creation of a pilot SI joint opening.

Referring back to FIGS. 4C and 4D, in a preferred embodiment, the proximal end 521a of the drill guide 520b comprises an extended region 519, which, as illustrated in FIG. 4G, comprises two (2) threaded holes 511a, 511b.

According to the invention, the threaded holes 511a, 511b are sized and configured to receive the threaded end 514 of a handle, such as the access sleeve handle 510a shown in FIGS. 3E and 3F (and handle 510b shown in FIG. 5D), and discussed above.

As illustrated in FIGS. 4C and 4D, the distal end 521b of the drill guide 520b comprises a pair of anchor members 531 that project from the distal end 521b of the drill guide 520b. According to the invention, the anchor members 531 are designed and configured to pierce and, preferably, engage biological tissue to maintain a fixed position of the drill guide 520b proximate thereto.

Referring now to FIG. 4H, there is shown one embodiment of a K-wire pin member 550.

As illustrated in FIG. 4H, the K-wire pin member 550 comprises an elongated cylindrical shaped member 552 comprising proximal and distal ends 554a, 554b, a head region 555 disposed on the proximal end 554a, and a K-wire tip 557.

As further illustrated in FIG. 4H, in some embodiments of the invention, the head region 555 of the elongated member 552 comprises a textured configuration to facilitate insertion of the K-wire pin member 550 into SI joint structures.

Referring now to FIG. 4I, there is shown another embodiment of a drill alignment pin, i.e., temporary fixation pin, 530b that is preferably employed with drill guide 520b. According to the invention, the temporary fixation pin 530b can also be employed with drill guide 520a.

As illustrated in FIG. 4I, the temporary fixation pin 530b preferably comprises an elongated guide member 533 comprising proximal and distal ends 535a, 535b, and a handle 537 that is disposed on the proximal end 535a of the guide member 533.

As further illustrated in FIG. 4I, the elongated guide member 533 of the temporary fixation pin 530b comprises a center region 543 similarly comprising a plurality of graduated markings 541, which preferably are readily detectable and, hence, readable via a conventional image capture apparatus, and a distal tapered end 540 that tapers to a point 542, which is adapted and configured to pierce bone structures and, as discussed below, when employed during creation of SI joint pilot openings, further supports and stabilizes the drill guide 520b.

The drill guide assembly 500b provides several advantages over drill guide 500a. Among the advantages are the following:

an access sleeve, such as access sleeve 502 shown in FIG. 3B, is not required;

only a minimal incision, i.e., an incision length in the range of 2.0 cm to 3.0 cm, is required to create the pilot openings in the SI joint structures and implant a SI joint prosthesis therein;

direct visualization of the drill bit 501b and, hence, markings (i.e., drill bit depth markings) 513 thereon is provided during creation of pilot SI joint openings;

direct (and optimal) visualization of the SI joint structures is provided after creation of the pilot openings in the SI joint structures; and consistent, optimal arthrodesis of the dysfunctional SI joint is achieved after placement of a SI joint prosthesis therein.

Figure 5A:
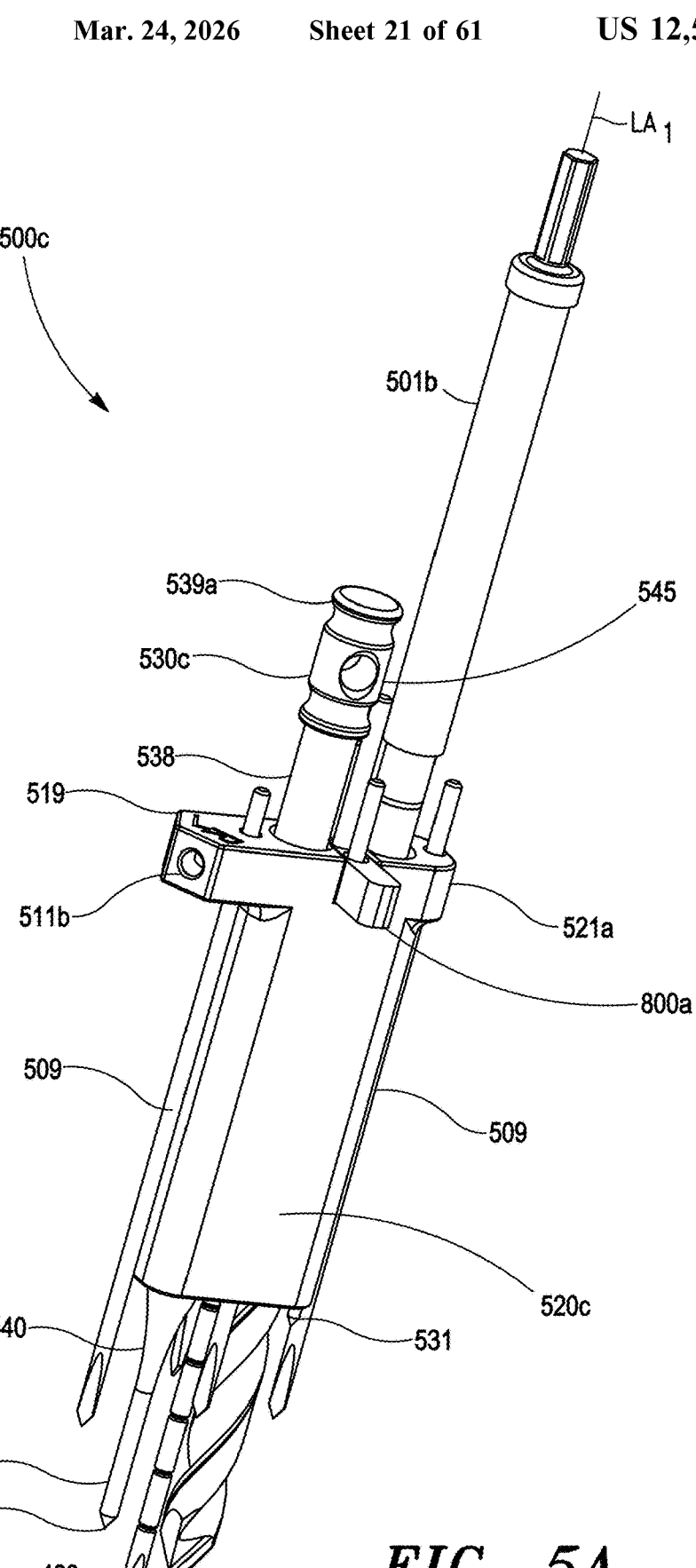
FIG. 5A is a perspective view of another embodiment of a drill guide assembly comprising yet another embodiment of the drill guide having an elongated guide member, bone dislodging apparatus, and another embodiment of a temporary fixation pin disposed in the prosthesis internal access opening thereof, in accordance with the invention.
Figure 5B:
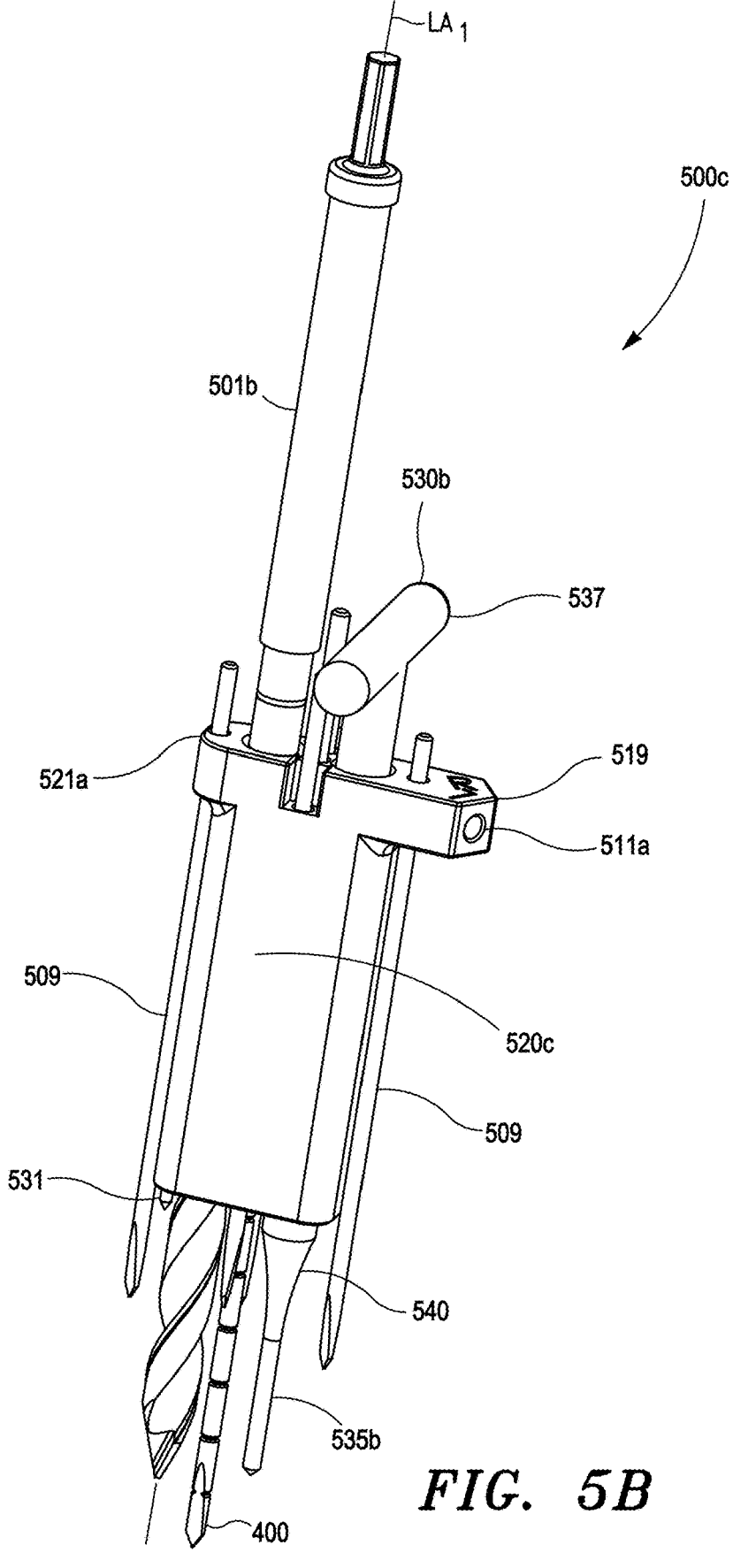
FIG. 5B is a perspective view of the drill guide assembly shown in FIG. 5A comprising the elongated guide member and bone dislodging apparatus shown in FIG. 5A, and the embodiment of the temporary fixation pin shown in FIG. 4I disposed in the prosthesis internal access opening of the drill guide, in accordance with the invention.
Figure 5C:
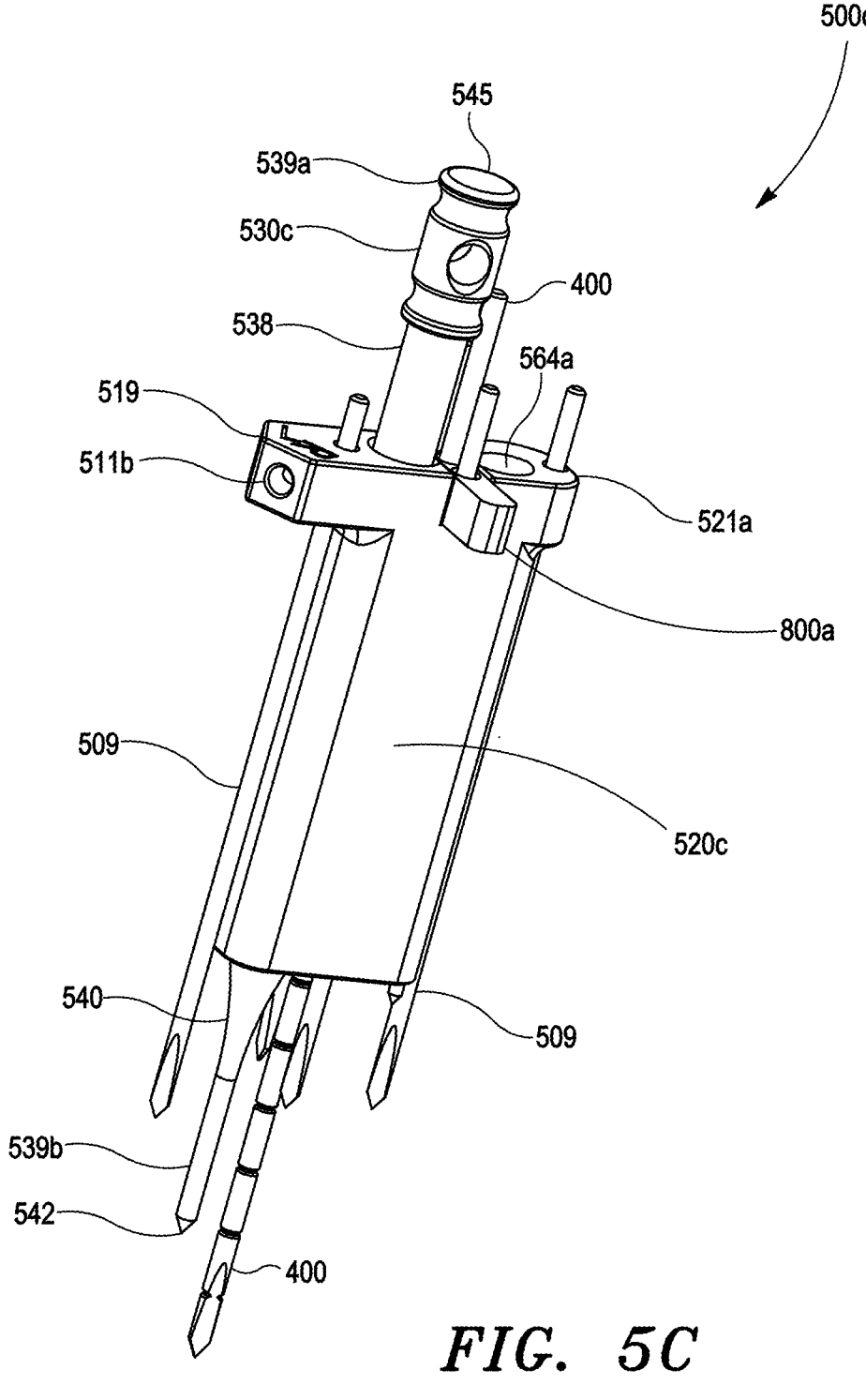
FIG. 5C is a perspective view of the drill guide assembly shown in FIG. 5A comprising the elongated guide member and temporary fixation pin shown in FIG. 5A disposed in the prosthesis internal access opening of the drill guide, in accordance with the invention.

Referring now to FIGS. 5A-5C, there is shown another embodiment of a drill guide assembly of the invention (denoted "500c").

As illustrated in FIGS. 5A and 5B, the drill guide assembly 500c generally comprises a drill guide 520c, a bone dislodging apparatus; preferably, drill bit 501c, temporary fixation pin 530b, which is shown in FIG. 4I and discussed above, and temporary fixation pin 530c, which is shown in FIGS. 5A and 5C.

In some embodiments, the drill guide assembly 500c further comprises K-wire pin member 550, which is shown in FIG. 4H, and drill alignment pin 530a, which is shown in FIG. 3K.

As illustrated in FIGS. 5A and 5C, the temporary fixation pin 503c comprises proximal and distal ends 539a, 539b, and a similar elongated body as K-wire pin member 550 shown in FIG. 4H and a distal tapered end 540 that tapers to a point 542, which is similar to the end region of temporary fixation pin 530b shown in FIGS. 4I and 5B.

As discussed in detail below, in some embodiments, the temporary fixation pin 530c is employed as a bone tamp to provide a guide recess to position or guide a bone dislodging member of the invention into a bone structure and abate undesired trajectories of the bone dislodging member.

Figure 6C:
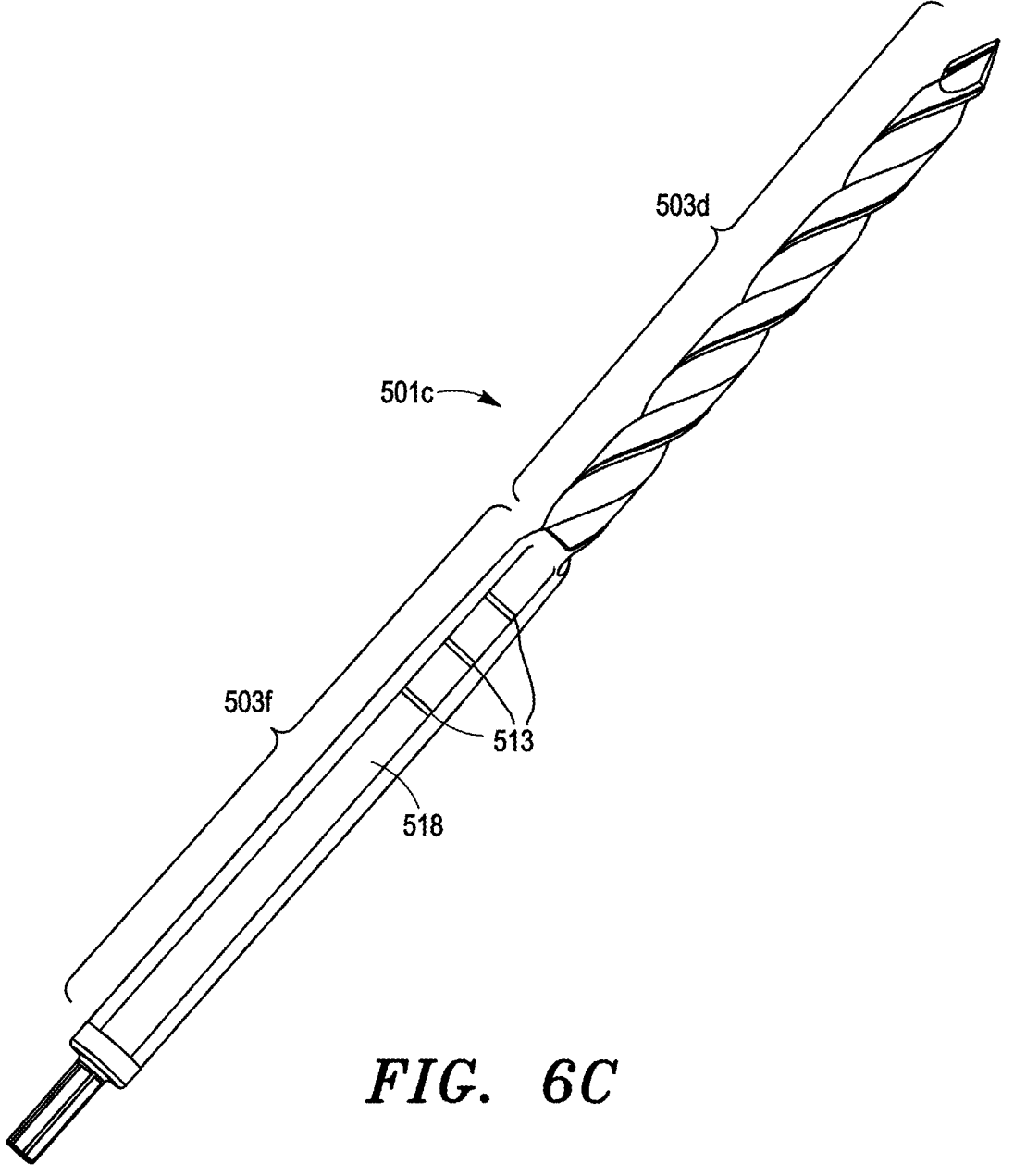
FIG. 6C is a perspective view of yet another embodiment of a bone dislodging apparatus, in accordance with the invention.

Referring now to FIG. 6C, in a preferred embodiment, the drill bit 501c similarly comprises an elongated rod structure having a proximal end region or base 503f and a bone dislodging end region 503d.

As illustrated in FIG. 6C, in some embodiments, the proximal end region 503f of the drill bit 501c comprises a larger circumference than the bone dislodging end region 503d to align the drill bit 501c in the larger lobe portions 564a, 564b of the prosthesis internal access opening 560 in the drill guide 520c (and drill guide 520d), which, as discussed in detail below, is necessary to receive the SI joint prosthesis 70 therein.

As further illustrated in FIG. 6C, in a preferred embodiment, the drill bit 501c similarly comprises the plurality of graduated markings 513 shown on drill bit 501b shown in FIG. 6B and discussed above.

However, in view of the larger circumference (or periphery) of the proximal end region 503f of the drill bit 501c, to abate premature wear of the graduated markings 513 and, hence, compromised detection and readability of the markings 513 when the drill bit 501c is repeatedly advanced into and through bone structures, as illustrated in FIG. 6C, the graduated markings 513 are positioned on a plurality of flat regions 518 on the proximal end region 503f of the drill bit 501c, whereby the graduated markings 513 are inset relative to the outer periphery of the proximal end region 503f of the drill bit 501c.

As illustrated in FIGS. 5F-5M, the drill guide 520c similarly comprises proximal and distal ends 521a, 521b and four (4) K-wire lumens 529a, 529b, 529c, 529d; the four (4) K-wire lumens 529a, 529b, 529c, 529d extending from the proximal end 521a to the distal end 521b of the drill guide 520c.

As illustrated in FIGS. 5A, 5C, 5E, 5L, and 5M and discussed in detail below, the drill guide 520c further comprises an elongated guide member (or sleeve) 800a.

Figure 5D:
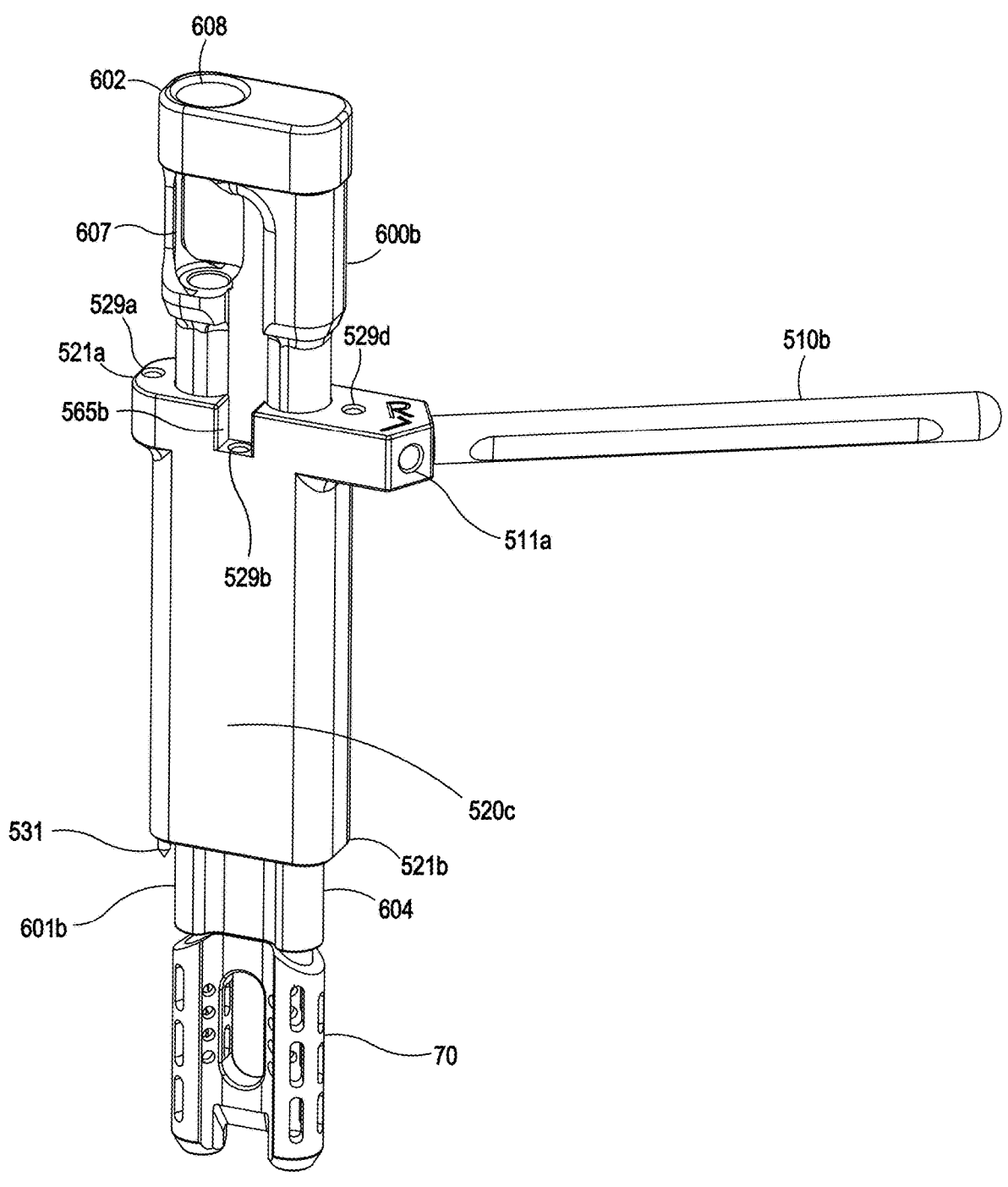
FIG. 5D is a perspective view of the drill guide shown in FIG. 5A showing a handle in communication therewith and a prosthesis deployment member with a SI joint prosthesis engaged thereto disposed in the prosthesis internal access opening of the drill guide, in accordance with the invention.
Figure 5E:
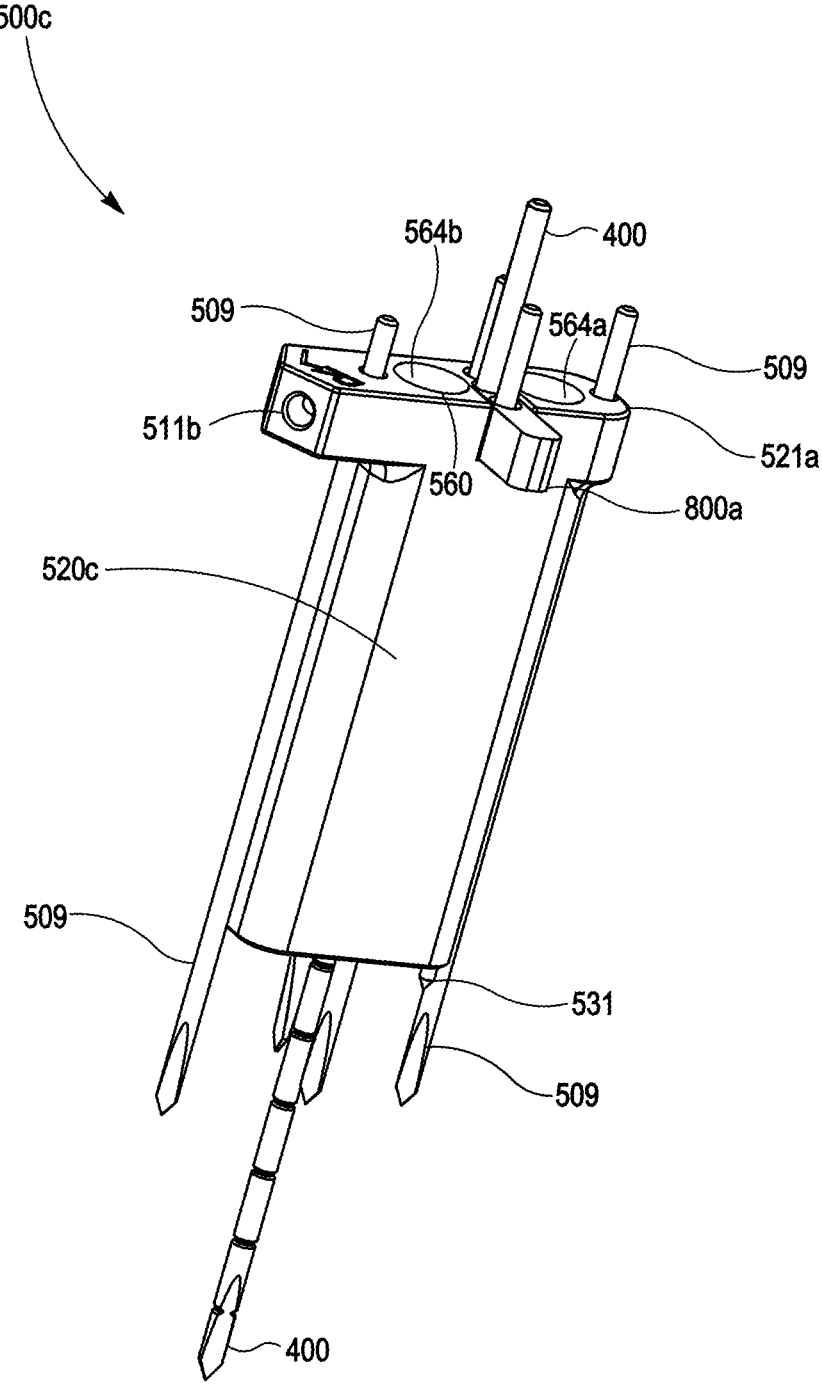
FIG. 5E is another perspective view of the drill guide shown in FIG. 5A showing the elongated guide member disposed in the prosthesis internal access opening thereof and a plurality of K-wires disposed in the K-wire lumens thereof, in accordance with the invention.

As illustrated in FIGS. 5F-5M, the drill guide 520c comprises a prosthesis internal access opening 560, which, as discussed in detail below, is sized and configured to receive and position SI joint prosthesis 70 therein. As also shown in FIG. 5D and discussed below, the prosthesis internal access opening 560 is also sized and configured to receive and position a prosthesis deployment assembly of the invention, in this instance, prosthesis deployment assembly 600b, therein.

Figures 5F, 5G:
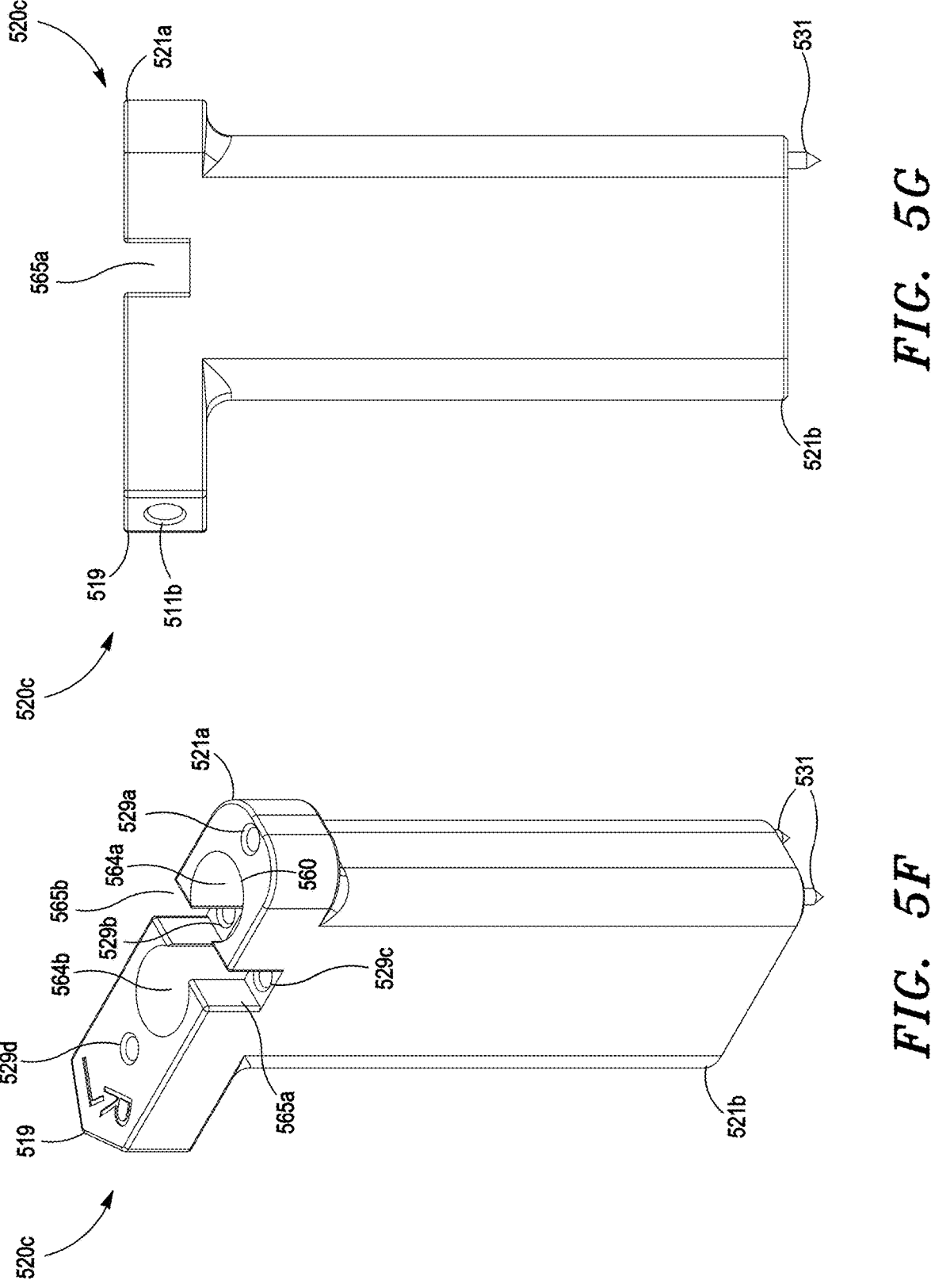
FIG. 5F is a rear perspective view of the drill guide shown in FIG. 5A, in accordance with the invention.
FIG. 5G is a right-side plan view of the drill guide shown in FIG. 5F, in accordance with the invention.
Figure 5I:
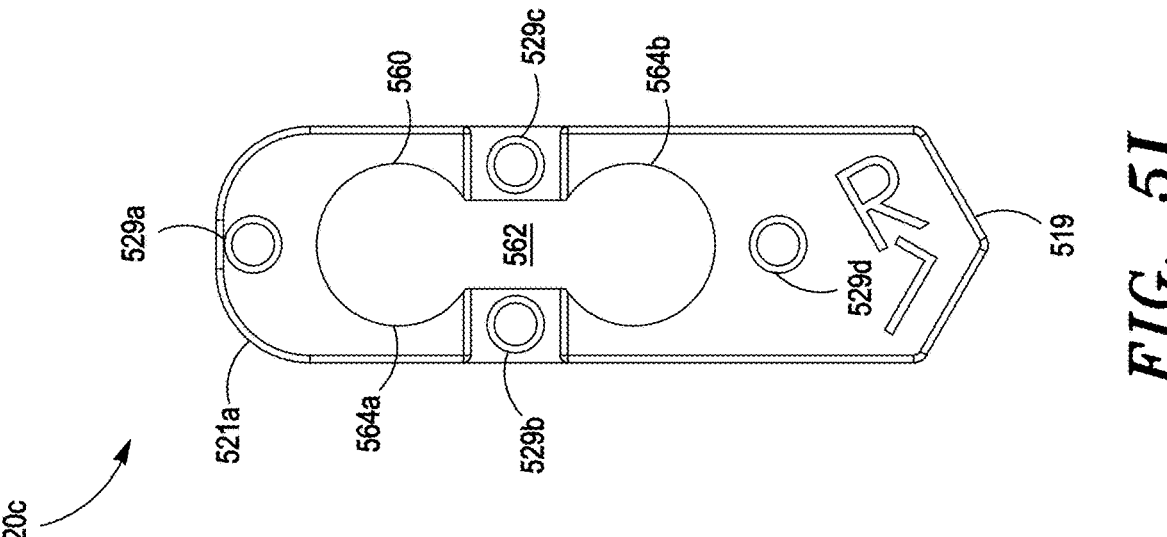
FIG. 5I is a top plan view of the drill guide shown in FIG. 5F, in accordance with the invention.
Figure 5H:
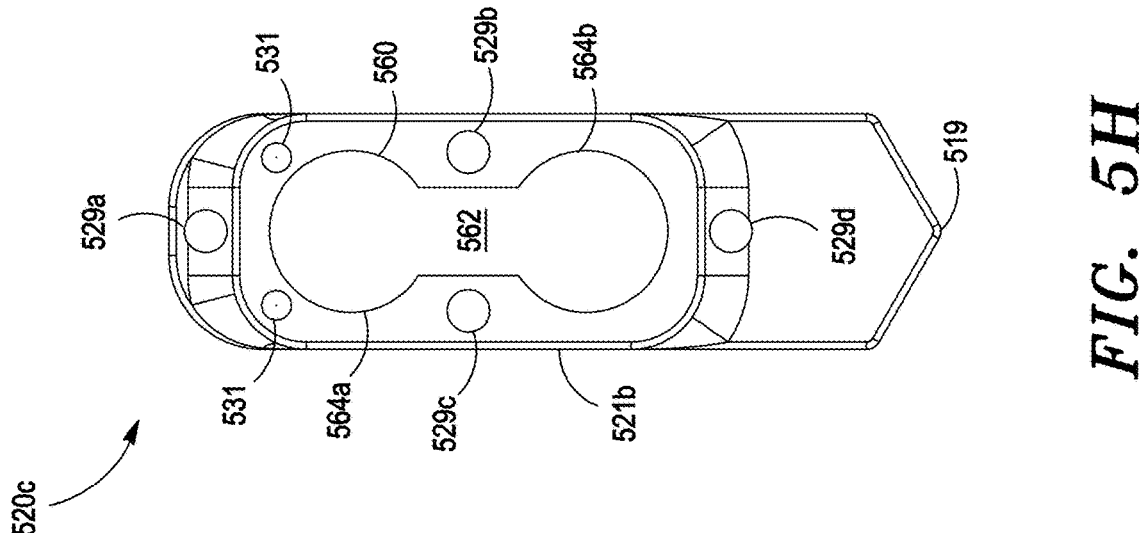
FIG. 5H is a bottom plan view of the drill guide shown in FIG. 5F, in accordance with the invention.

As illustrated in FIGS. 5H and 5I, the prosthesis internal access opening 560 extends from the proximal end 521a to the distal end 521b of the drill guide 520c and comprises a "dogbone" or "bi-lobe" cross-sectional shape comprising contiguous first and second lobe portions 564a, 564b connected by a medial portion 562.

As illustrated in FIGS. 5H and 5I, in a preferred embodiment, the medial portion 562 of the prosthesis internal access opening 560 is sized and configured to receive the elongated guide member 800a of drill guide 520c.

Figure 5K:
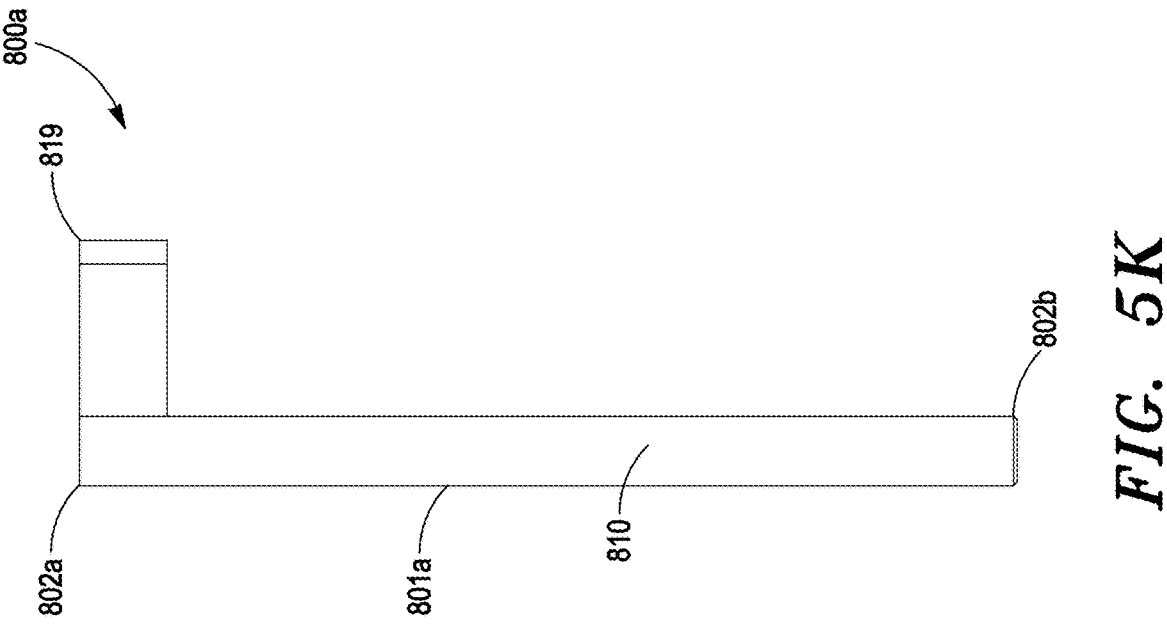
FIG. 5K is a left-side plan view of the elongated guide member shown in FIG. 5J, in accordance with the invention.
Figure 5J:
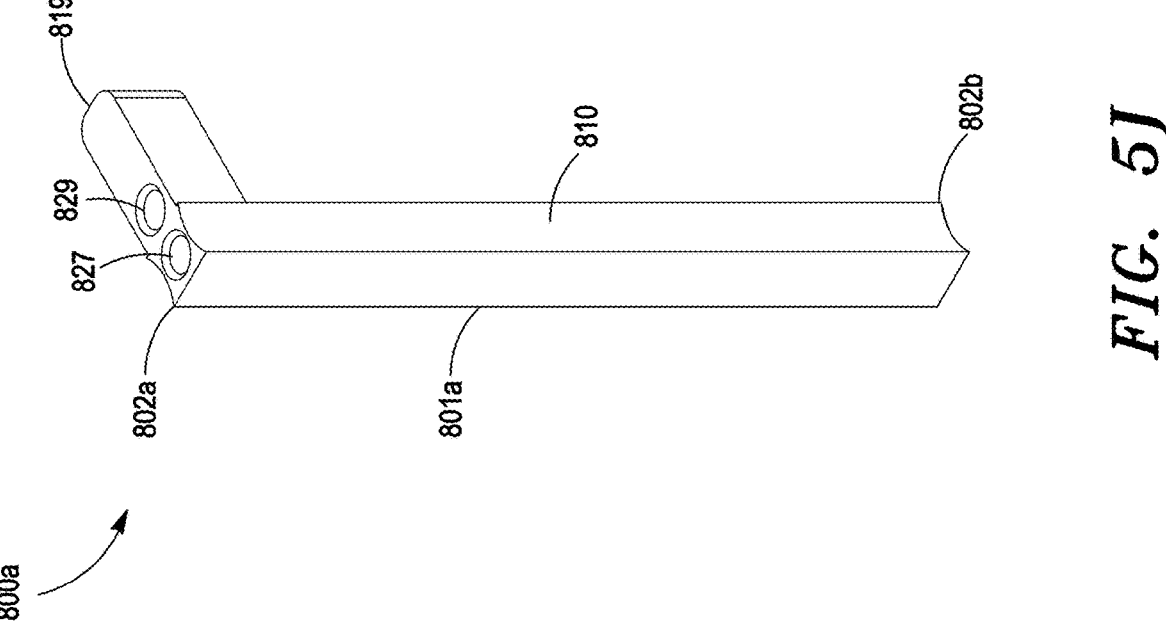
FIG. 5J is a rear perspective view of the elongated guide member shown in FIGS. 5A, 5C, and 5E, in accordance with the invention.
Figures 5L, 5M:
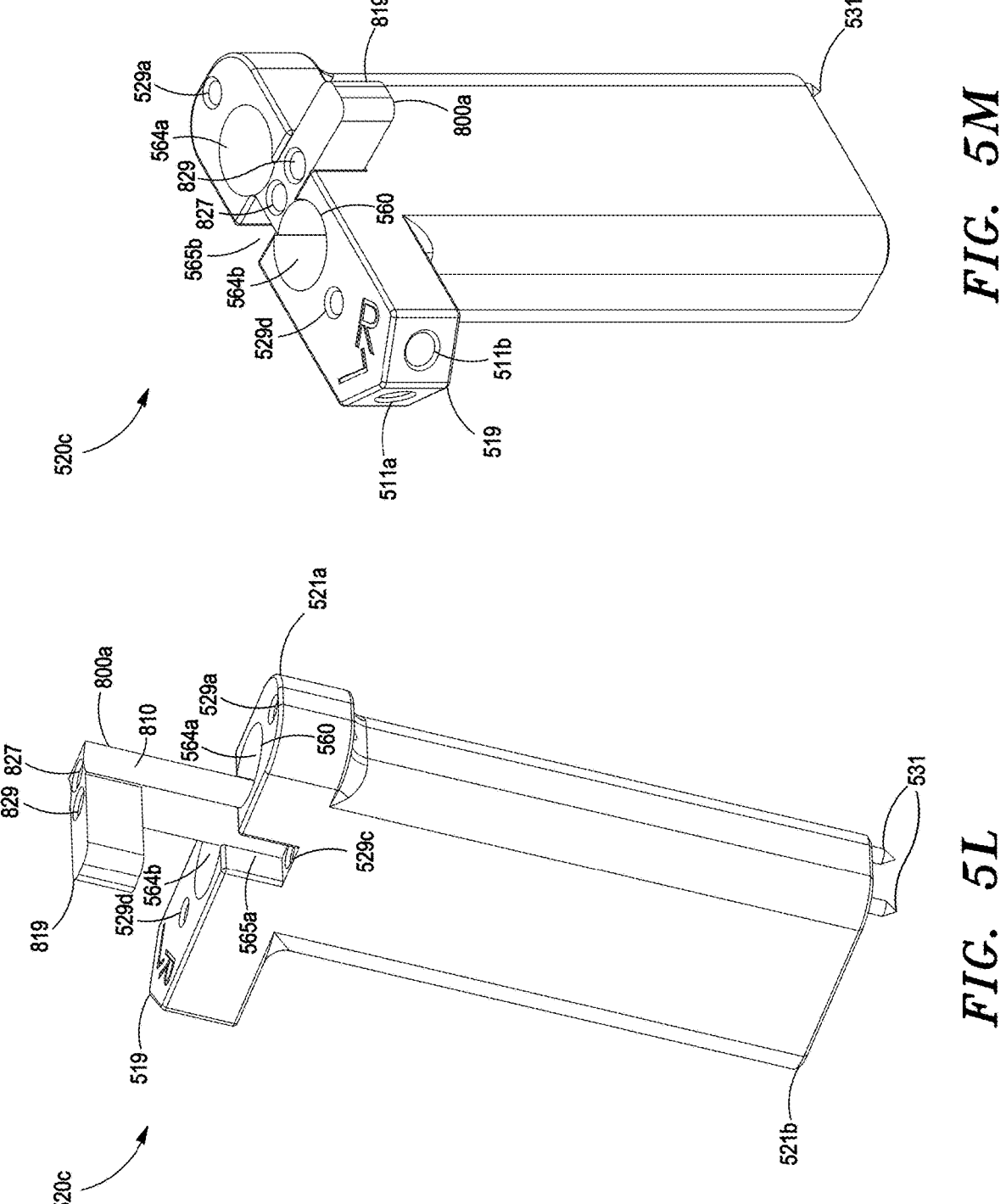
FIG. 5L is another rear perspective view of the drill guide shown in FIG. 5F showing the elongated guide member partially disposed in the prosthesis internal access opening thereof, in accordance with the invention.
FIG. 5M is a front perspective view of the drill guide shown in FIG. 5F showing the elongated guide member fully disposed in the prosthesis internal access opening thereof, in accordance with the invention.

Referring now to FIGS. 5J and 5K, there is shown one embodiment of elongated guide member 800a.

As illustrated in FIGS. 5J and 5K, the elongated guide member 800a preferably comprises an elongated body 801a comprising proximal and distal ends 802a, 802b and an extended, substantially perpendicular end region 819 that is disposed on the proximal end 802a of the guide member 800a.

As further illustrated in FIGS. 5J and 5K, the elongated body 801a of the guide member 800a preferably comprises opposed concave regions 810 having a curvature substantially similar to the outer periphery of the first and second lobe portions 564a, 564b of the prosthesis internal access opening 560 of the drill guide 520c.

As further illustrated in FIGS. 5J and 5K, in a preferred embodiment, the elongated guide member 800a further comprises a guide member lumen 827 that extends through the guide member 800a, i.e., the elongated body 801a thereof, and is sized and configured to receive a guide pin of the invention, such as guide pin 400 shown in FIGS. 2A and 2B, and a guide member K-wire lumen 829 disposed on the extended end region 819 of the guide member 800a that is sized and configured to receive a K-wire of the invention, such as K-wires 509 shown in FIGS. 5A-5C.

According to the invention, the guide member lumen 827 of the elongated guide member 800a can similarly also be sized and configured to receive various other suitable instruments, such as surgical scopes, center punches, location pins, drill probes, and drill stop assemblies, to facilitate the creation of a pilot SI joint opening.

As illustrated in FIGS. 5A, 5C, 5E, 5L, and 5M, the elongated guide member 800a is sized and configured to slidably translate into the medial portion 562 of the prosthesis internal access opening 560.

As further illustrated in FIGS. 5A, 5C, 5E, 5L, and 5M, and the extended region 819 is also sized and configured to slidably translate into one of the two (2) guide member receiving slots 565a, 565b disposed on the proximal end 521a of the drill guide 520c.

Referring back to FIGS. 5F-5M, in a preferred embodiment, the first and second lobe portions 564a, 564b of the prosthesis internal access opening 560 of the drill guide 520c are similarly sized and configured to receive (i) a bone dislodging apparatus of the invention, such as drill bit 501c shown in FIG. 6C, and (ii) drill alignment pin 530a, temporary fixation pins 530b, 530c, and, if employed, K-wire pin member 550.

In a preferred embodiment, the opposed concave regions 810 of the elongated guide member 800a are sized and configured to allow slidable translation of a bone dislodging apparatus of the invention, e.g., drill bit 501c, and drill alignment pin 530a, temporary fixation pins 530b, 530c, and/or K-wire pin member 550 into and through the first and second lobe portions 564a, 564b when the elongated guide member 800a is positioned in the medial portion 562 of the prosthesis internal access opening 560.

As will readily be appreciated by one having ordinary skill in the art, the first and second lobe portions 564a, 564b and medial portion 562 can also readily accommodate various other suitable instruments, such as surgical scopes, center punches, location pins, drill probes, and drill stop assemblies.

Referring back to FIGS. 5L and 5M, in a preferred embodiment, the proximal end 521a of the drill guide 520c similarly comprises an extended region 519, which, as illustrated in FIG. 5M, similarly comprises two (2) threaded holes 511a, 511b.

According to the invention, the threaded holes 511a, 511b are similarly sized and configured to receive the threaded end of a handle, such as the threaded end 514 of access sleeve handle 510a shown in FIGS. 3E and 3F, and the handle 510b shown in FIG. 5D, and discussed above.

As illustrated in FIGS. 5F, 5G, and 5H, the distal end 521b of the drill guide 520c similarly comprises anchor members 531 that project from the distal end 521b of the drill guide 520c. As indicated above, the anchor members 531 are designed and configured to pierce and, preferably, engage biological tissue to maintain a fixed position of the drill guide 520c proximate thereto.

Referring now to FIGS. 5N-5U, there is shown another embodiment of a drill guide (denoted "520d") and an associated elongated guide member of the invention (denoted "800b") that can also be employed with the drill guide assembly 500c.

As illustrated in FIGS. 5N-5U, the drill guide 520d similarly comprises proximal and distal ends 521a, 521b and four (4) K-wire lumens 529a, 529b, 529c, 529d; the four (4) K-wire lumens 529a, 529b, 529c, 529d extending from the proximal end 521a to the distal end 521b of the drill guide 520d.

As illustrated in FIGS. 5R-5U and discussed in detail below, the drill guide 520d also similarly comprises an elongated guide member or sleeve (denoted "800b").

As illustrated in FIGS. 5N-5U, the drill guide 520d similarly comprises prosthesis internal access opening 560, which, as discussed in detail below, is sized and configured to receive and position SI joint prosthesis 70 therein.

Figures 5N, 5O:
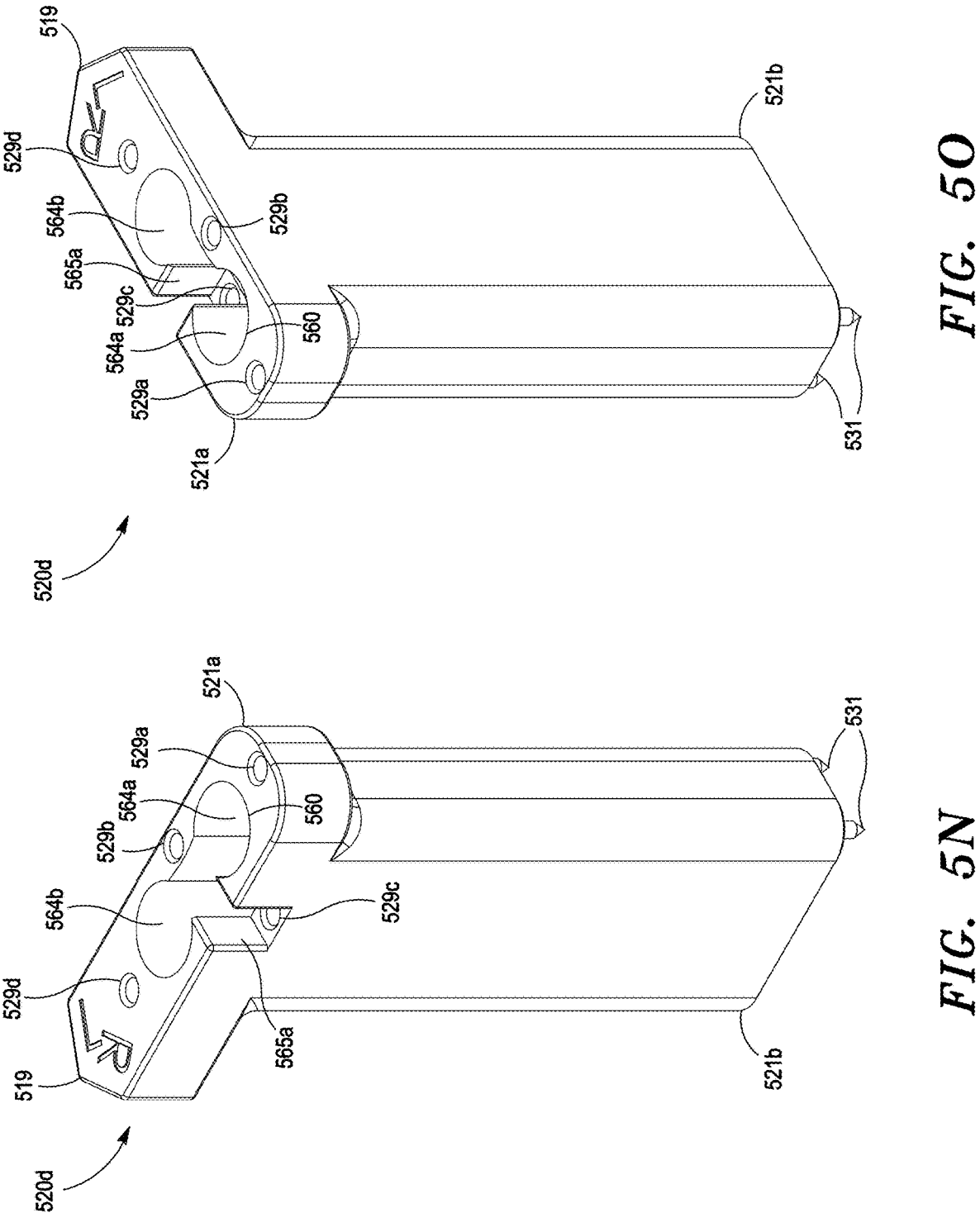
FIG. 5N is a rear perspective view of another embodiment of a drill guide, in accordance with the invention.
FIG. 5O is another rear perspective view of the drill guide shown in FIG. 5N, in accordance with the invention.
Figure 5Q:
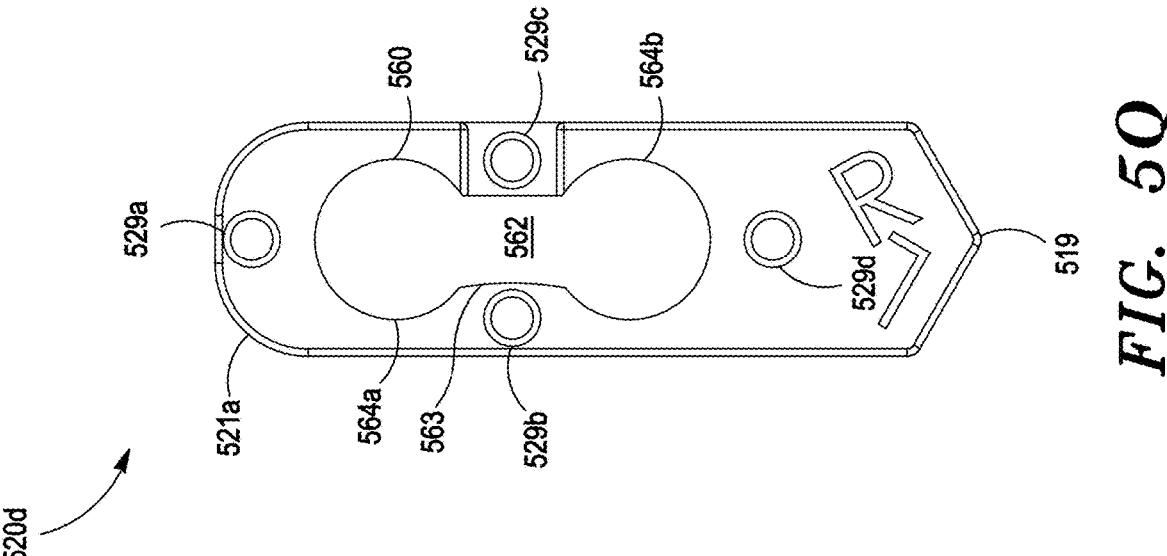
FIG. 5Q is a top plan view of the drill guide shown in FIG. 5N, in accordance with the invention.
Figure 5P:
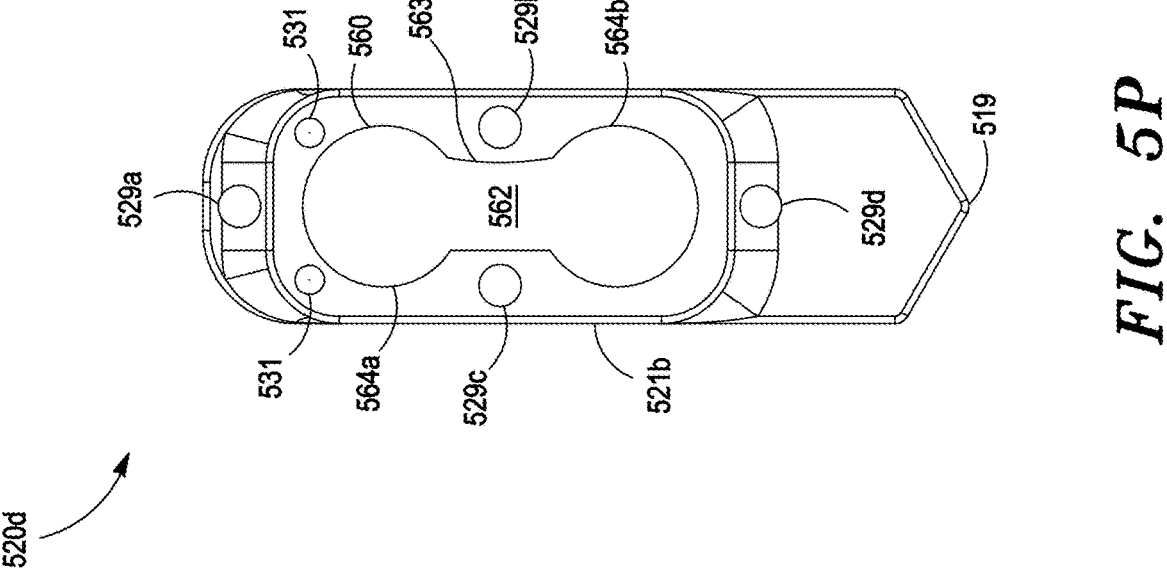
FIG. 5P is a bottom plan view of the drill guide shown in FIG. 5N, in accordance with the invention.

As illustrated in FIG. 5P and 5Q, the prosthesis internal access opening 560 similarly comprises a "dogbone" or "bi-lobe" cross-sectional shape comprising contiguous first and second lobe portions 564a, 564b connected by a medial portion 562.

As illustrated in FIGS. 5P and 5Q, in a preferred embodiment, the medial portion 562 of the prosthesis internal access opening 560 is sized and configured to receive the elongated guide member 800b of drill guide 520d.

As further illustrated in FIGS. 5P and 5Q, the medial portion 562 of the prosthesis internal access opening 560 comprises a convex portion 563 that is sized and configured to allow elongated guide member 800b to be received in the prosthesis internal access opening 560.

Figures 5R, 5S:
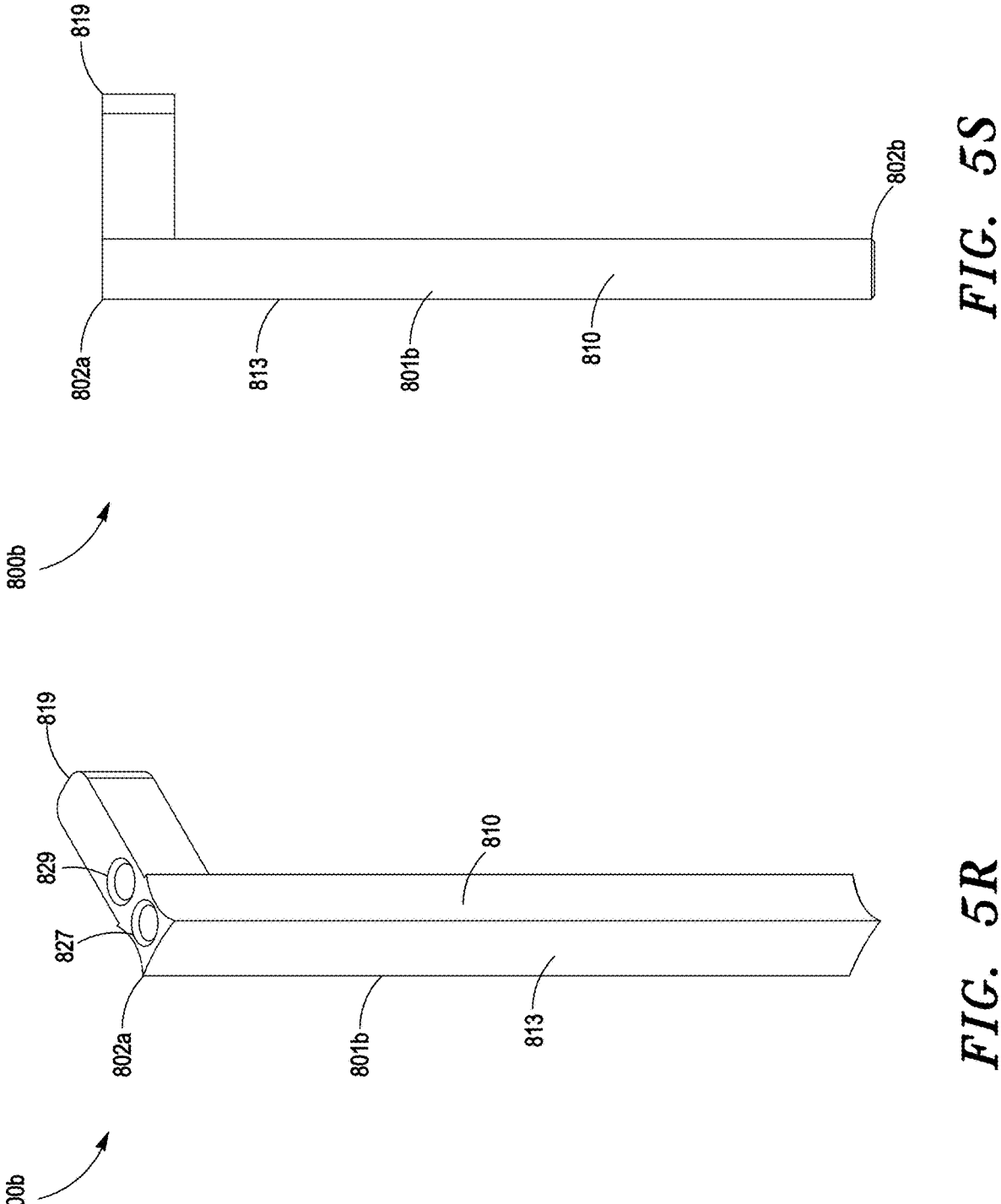
FIG. 5R is a rear perspective view of another embodiment of an elongated guide member, in accordance with the invention.
FIG. 5S is a left-side plan view of the elongated guide member shown in FIG. 5R, in accordance with the invention.

Referring now to FIGS. 5R and 5S, the elongated guide member 800b similarly comprises an elongated body 801b comprising proximal and distal ends 802a, 802b and an extended, substantially perpendicular end region 819 that is disposed on the proximal end 802a of the guide member 800b.

As further illustrated in FIGS. 5R and 5S, the elongated body 801b of the guide member 800b similarly comprises opposed concave regions 810 having a curvature substantially similar to the outer periphery of the first and second lobe portions 564a, 564b of the prosthesis internal access opening 560 of the drill guide 520d.

As further illustrated in FIGS. 5R and 5S, the elongated body 801b of the guide member 800b also comprises a further concave region 813 having a curvature substantially similar to (i.e., corresponding to) the outer periphery of the convex portion 563 of the medial portion 562 of the prosthesis internal access opening 560.

As further illustrated in FIGS. 5R and 5S, in a preferred embodiment, the elongated guide member 800b similarly comprises guide member lumen 827, which, as discussed above, is sized and configured to receive a guide pin of the invention, such as guide pin 400 shown in FIGS. 2A and 2B, and guide member K-wire lumen 829 disposed on the extended end region 819 of the guide member 800b.

Figures 5T, 5U:
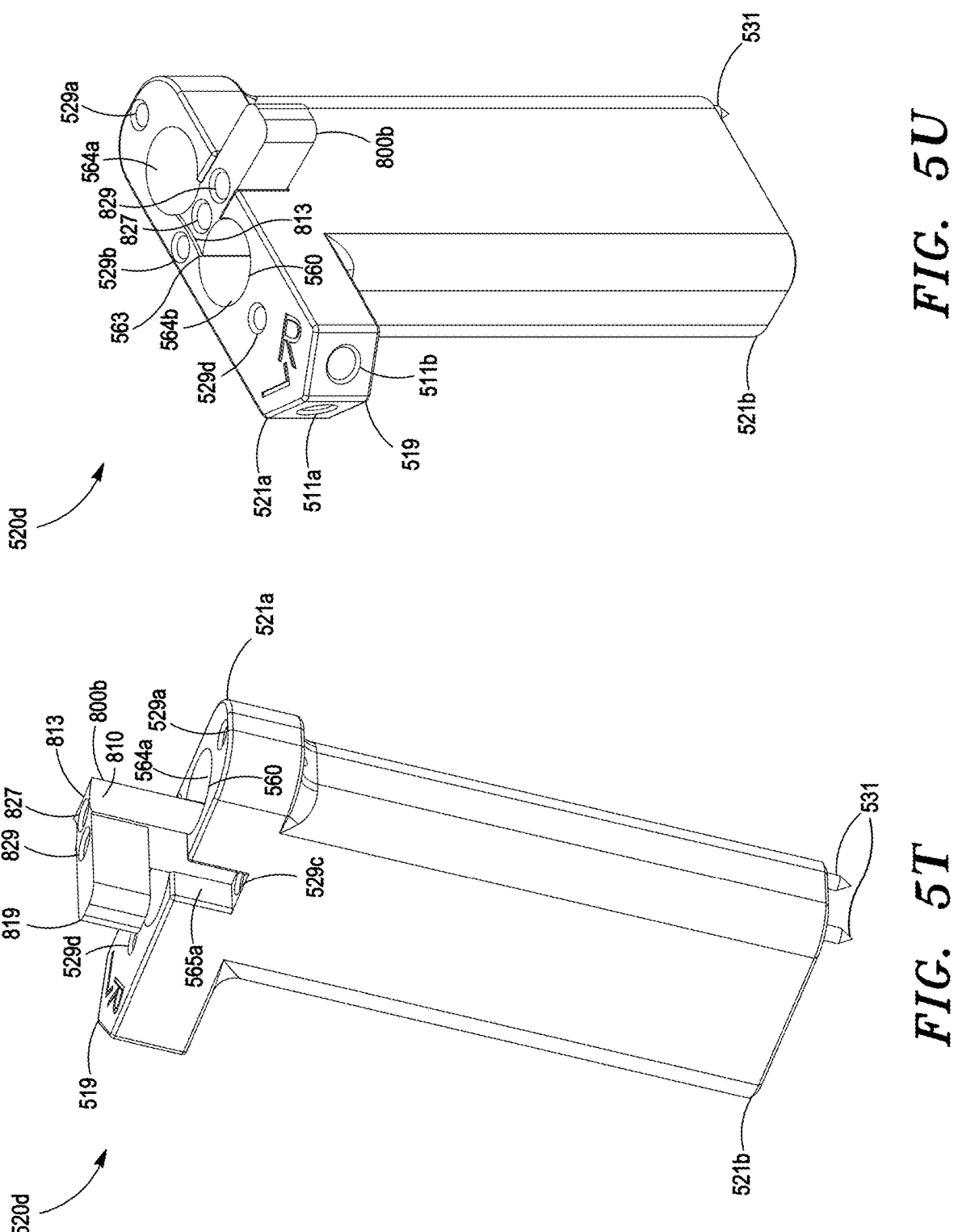
FIG. 5T is another rear perspective view of the drill guide shown in FIG. 5N showing the elongated guide member shown in FIGS. 5R and 5S partially disposed in the prosthesis internal access opening thereof, in accordance with the invention.
FIG. 5U is a front perspective view of the drill guide shown in FIG. 5N showing the elongated guide member shown in FIGS. 5R and 5S fully disposed in the prosthesis internal access opening thereof, in accordance with the invention.

As illustrated in FIGS. 5T and 5U, the elongated guide member 800b is similarly sized and configured to slidably translate into the medial portion 562 of the prosthesis internal access opening 560 in drill guide 520d.

As further illustrated in FIGS. 5T and 5U, the extended region 819 of the elongated guide member 800b is also sized and configured to slidably translate into the guide member receiving slot 565a disposed on the proximal end 521a of the drill guide 520d.

Referring back to FIGS. 5N-5U, in a preferred embodiment, the first and second lobe portions 564a, 564b of the prosthesis internal access opening 560 of the drill guide 520d are similarly sized and configured to receive (i) a bone dislodging apparatus of the invention, such as drill bit 501c shown in FIG. 6C, and (ii) drill alignment pin 530a, temporary fixation pins 530b, 530c, and, if employed, K-wire pin member 550.

In a preferred embodiment, the opposed concave regions 810 of the elongated guide member 800b are similarly sized and configured to allow slidable translation of a bone dislodging apparatus of the invention, e.g., drill bit 501c, and drill alignment pin 530a, temporary fixation pins 530b, 530c, and/or K-wire pin member 550 into and through the first and second lobe portions 564a, 564b when the elongated guide member 800b is positioned in the medial portion 562 of the prosthesis internal access opening 560.

Referring again to FIG. 5U, in a preferred embodiment, the proximal end 521a of the drill guide 520d similarly comprises an extended region 519, which, as illustrated in FIG. 5U, similarly comprises threaded holes 511a, 511b. The threaded holes 511a, 511b are similarly sized and configured to receive the threaded end of a handle, such as the threaded end 514 of access sleeve handle 510a shown in FIGS. 3E and 3F, and handle 510b shown in FIG. 5D, and discussed above.

As illustrated in FIGS. 5N, 5O, and 5P, the distal end 521b of the drill guide 520d similarly comprises anchor members 531 that project from the distal end 521b of the drill guide 520d, which, as indicated above, are designed and configured to pierce and, preferably, engage biological tissue to maintain a fixed position of the drill guide 520d proximate thereto.

As will readily appreciated by one having ordinary skill in the art, the drill guide assembly 500c provides all the seminal advantages provided by drill guide assembly 500b, including:

an access sleeve, such as access sleeve 502 shown in FIG. 3B, is not required;

only a minimal incision, i.e., an incision length in the range of 2.0 cm to 3.0 cm, is required to create the pilot openings in the SI joint structures and implant a SI joint prosthesis therein;

direct visualization of the drill bit 501c (or drill bit 501b, if employed) and, hence, markings (i.e., drill bit depth markings) 513 thereon is provided during creation of pilot SI joint openings;

direct (and optimal) visualization of the SI joint structures is provided after creation of the pilot openings in the SI joint structures; and consistent, optimal arthrodesis of the dysfunctional SI joint is achieved after placement of a SI joint prosthesis therein.

The drill guide assembly 500c also provides consistent, optimal guidance of SI joint prostheses of the invention, e.g., SI joint prosthesis 70, into pilot SI joint openings.

As indicated above, in a preferred embodiment, the drill guide assemblies 500a, 500b, 500c are configured and adapted to create pilot SI joint openings in SI joint bone structures to accommodate placement of a SI joint prosthesis of the invention therein.

According to the invention, the drill guide assemblies of the invention 500a, 500b, 500c are configured and adapted to create pilot SI joint openings in SI joint bone structures of various sizes and configurations.

Figure 7A:
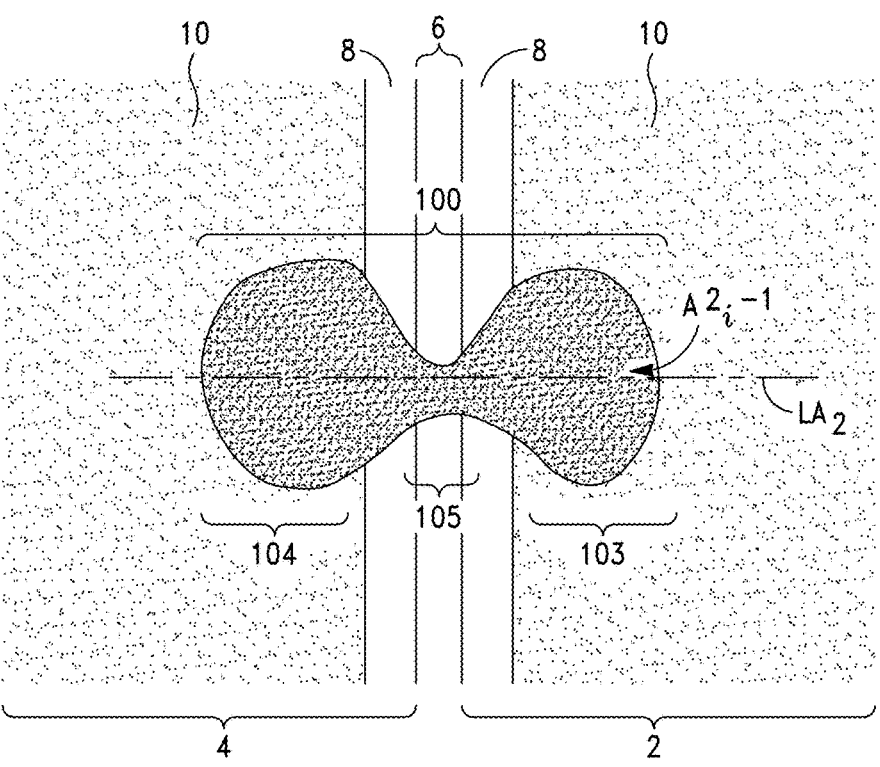
FIG. 7A is a further illustration of the SI joint shown in FIG. 1F showing one embodiment of a pilot SI joint opening, in accordance with the invention.

Referring now to FIG. 7A, there is shown one embodiment of a pilot SI joint opening of the invention (denoted "100") that can be created with the defect creation assemblies of the invention; particularly, drill guide assemblies 500a, 500b, 500c.

As illustrated in FIG. 7A, the pilot SI joint opening 100 comprises a three-dimensional opening comprising first and second lobe regions 103, 104; the first lobe region 103 being disposed in the sacrum 2 and comprising a sacrum opening three-dimensional shape, and the second lobe region 104 being disposed in the ilium 4 and comprising an ilium opening three-dimensional shape.

As further illustrated in FIG. 7A, the three-dimensional pilot SI joint opening 100 further comprises an SI joint opening cross-sectional shape in a plane that intersects the sacrum 2 and ilium 4; the plane being substantially perpendicular to the longitudinal axis $LA_1$ of the drill guide assemblies 500a, 500b, 500c when the drill guide assemblies 500a, 500b, 500c and, hence, drill bits 501a, 501b, 501c thereof, are disposed in a defect creation position in the dysfunctional SI joint. The three-dimensional pilot SI joint opening cross-sectional shape thus comprises the sacrum opening three-dimensional shape and ilium opening three-dimensional shape.

In some embodiments, the pilot SI joint opening cross-sectional shape (i.e., pilot SI joint opening 100) is defined in part by at least one noncircular cross-sectional shaped region (denoted "105") in the noted plane.

As additionally illustrated in FIG. 7A, the three-dimensional pilot SI joint opening 100, i.e., cross-sectional shape thereof, also defines a cross-sectional area of the three-dimensional pilot SI joint opening cross-sectional shape (denoted "$A^2_i$-1").

The three-dimensional pilot SI joint opening 100, i.e., cross-sectional shape thereof, also comprises a longitudinal axis (denoted "$LA_2$") in the plane that intersects the sacrum 2 and ilium 4 and an initial pilot SI joint opening length along the axis $LA_2$.

Figure 7B:
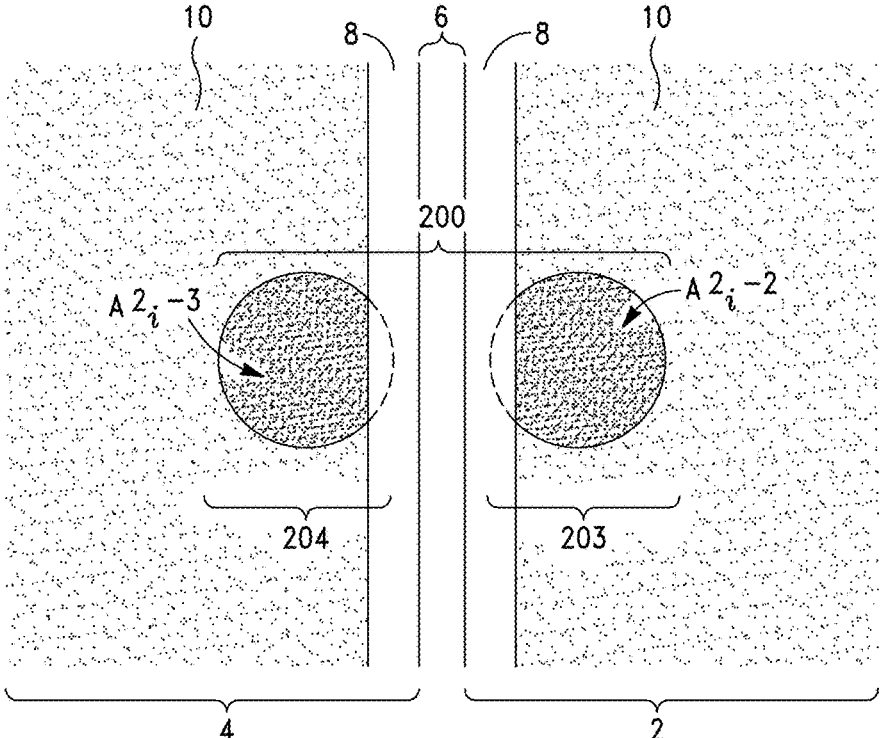
FIGS. 7B and 7C are illustrations of further embodiments of SI joint openings, in accordance with the invention.

Referring now to FIG. 7B, there is shown a further pilot SI joint opening of the invention (denoted "200") that can be created with a defect creation assembly of the invention.

As illustrated in FIG. 7B, the pilot SI joint opening 200 comprises two three-dimensional pilot or guide portions or regions 203, 204; the first guide portion 203 being disposed in the sacrum 2 and the second guide portion 204 being disposed in the ilium 4.

According to the invention, the sacrum and ilium guide portions 203, 204 can comprise various configurations, e.g., cross-sectional shapes, and sizes to, as discussed in detail below, accommodate insertion of defined regions of a prosthesis of the invention therein and transition of the sacrum and ilium guide portions 203, 204 from pilot or first configurations and sizes to expanded second configurations and sizes when the prosthesis is inserted therein.

According to the invention, the sacrum and ilium guide portions 203, 204 can also be disposed at various locations in the sacrum 2 and ilium 4. In some embodiments, the sacrum and ilium guide portions 203, 204 are disposed in the sacrum 2 and ilium 4 such that at least a portion of the sacrum and ilium guide portions 203, 204 extends into the cortical bone 8 of the SI joint structures, i.e., sacrum 2 and ilium 4, as shown in FIG. 7B, or the juncture between the sacrum 2 and ilium 4.

In some embodiments, the sacrum and ilium guide portions 203, 204 are solely disposed in the sacrum 2 and ilium 4, as shown in FIG. 4C.

As illustrated in FIG. 7B, in one preferred embodiment, the sacrum and ilium guide portions 203, 204 comprise substantially circular cross-sectional shapes.

As further illustrated in FIG. 7B, the sacrum and ilium guide portions 203, 204 of the pilot SI joint opening 200, i.e., cross-sectional shape thereof, define cross-sectional areas of the sacrum and ilium guide portions 203, 204 (denoted "$A^2_i$-2" and "$A^2_i$-3", respectively).

In a preferred embodiment, the sacrum and ilium guide portions 203, 204 of the pilot SI joint opening 200 are disposed on a plane that similarly intersects the sacrum 2 and ilium 4.

SI Joint Prostheses

According to the invention, various suitable SI joint prostheses, such as the prostheses illustrated in FIGS. 12A-12C, 13A-13B, 14A-14C and 15A-15D of Co-pending U.S. application Ser. No. 13/857,977, are suitable for insertion into pilot SI joint openings of the invention (i.e., SI joint openings 100, 200 described above) in a SI joint created by the drill guide assemblies 500a, 500b, and 500c, and into and through articular cartilage and cortical bone 8 (and trabecular bone 10), which define the SI joint.

Referring now to FIGS. 10A-10I, there is shown a preferred SI joint prosthesis (denoted "70") of the invention, which is particularly suitable for placement in pilot SI joint openings of the invention in a SI joint, and into and through articular cartilage and bone structures (i.e., cortical and trabecular bone 8, 10), which define the SI joint.

Figure 10A:
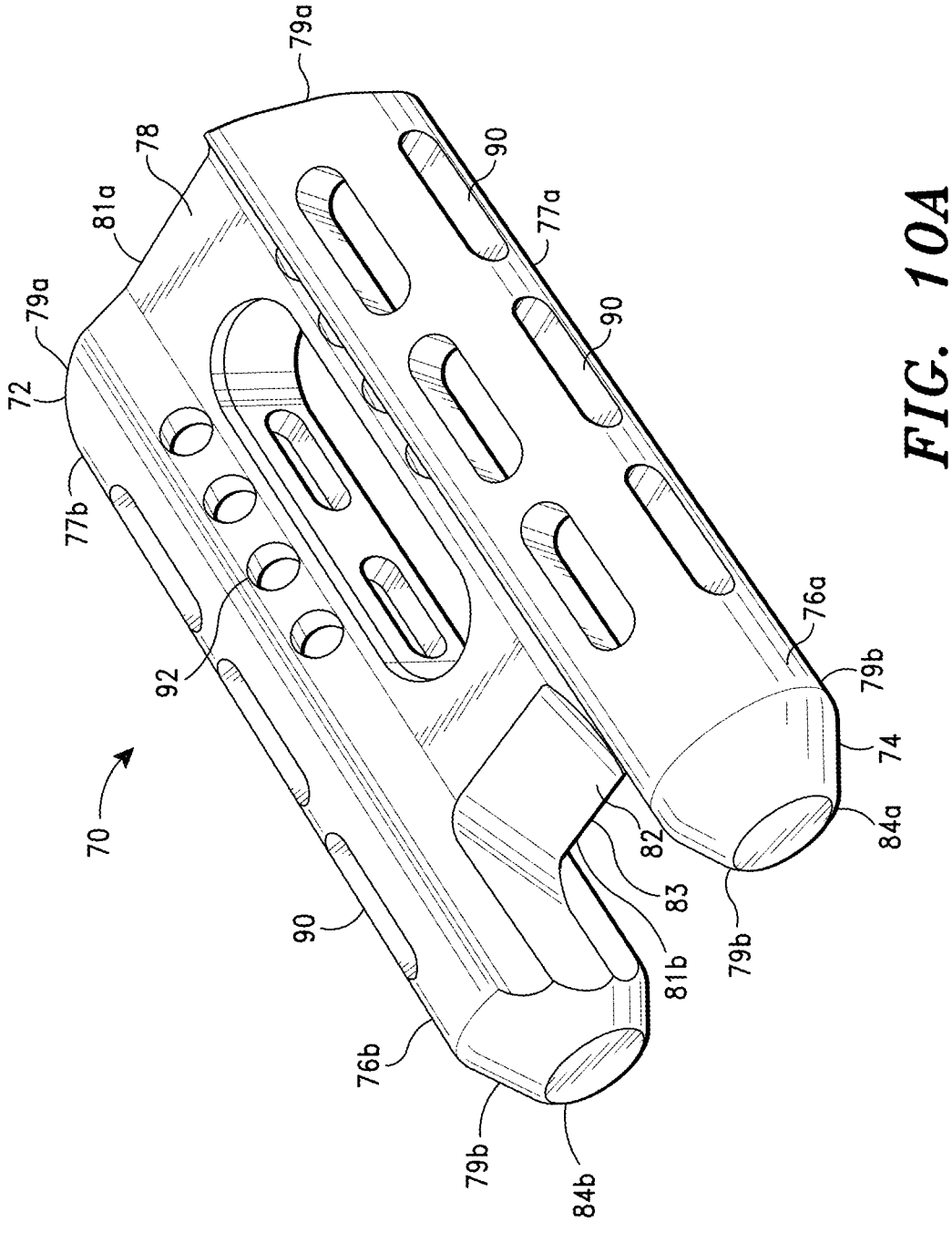
FIG. 10A is a perspective view of one embodiment of a SI joint prosthesis, in accordance with the invention.
Figure 10B:
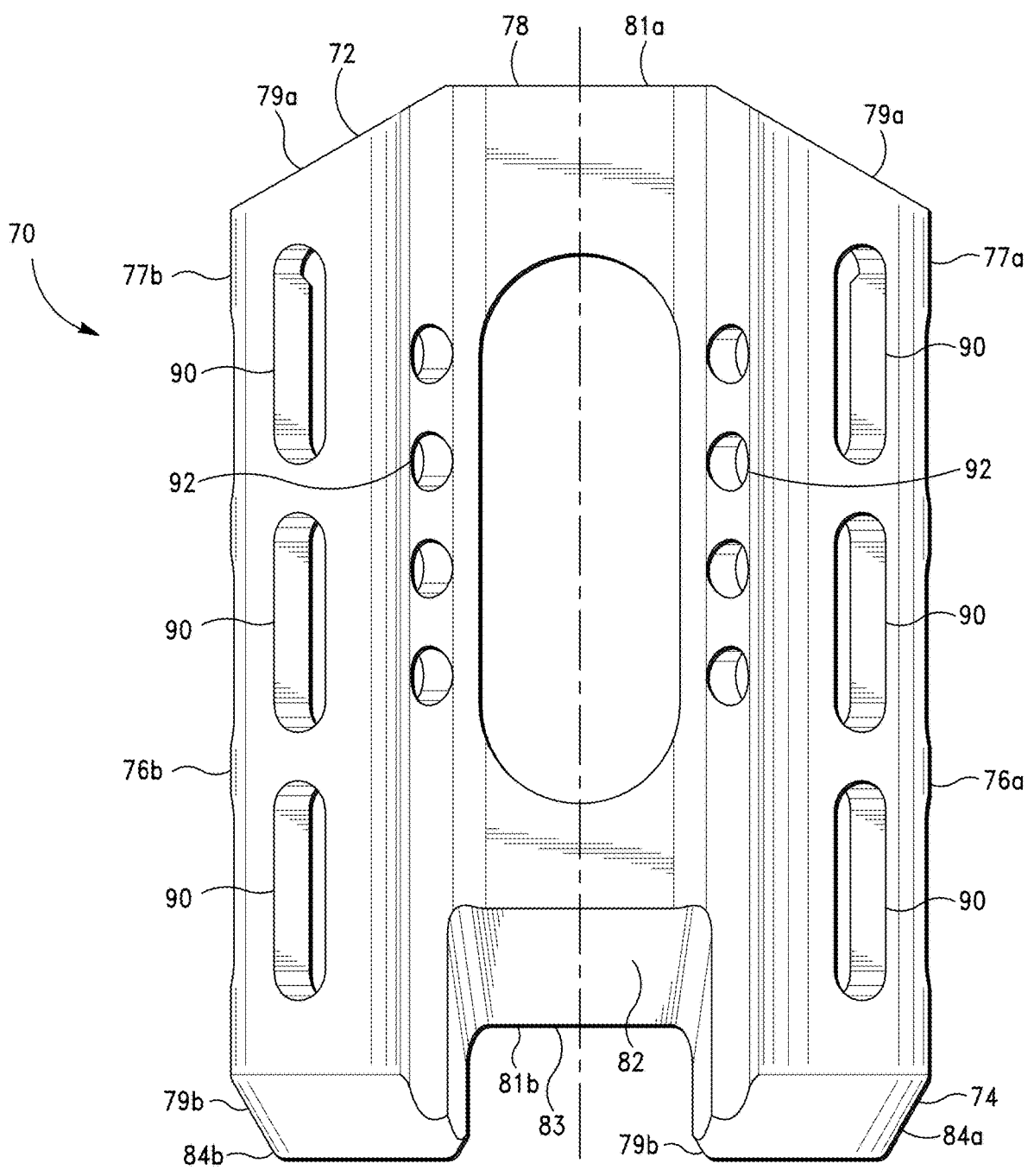
FIG. 10B is a top plan view of the SI joint prosthesis shown in FIG. 10A, in accordance with the invention.
Figure 10C:
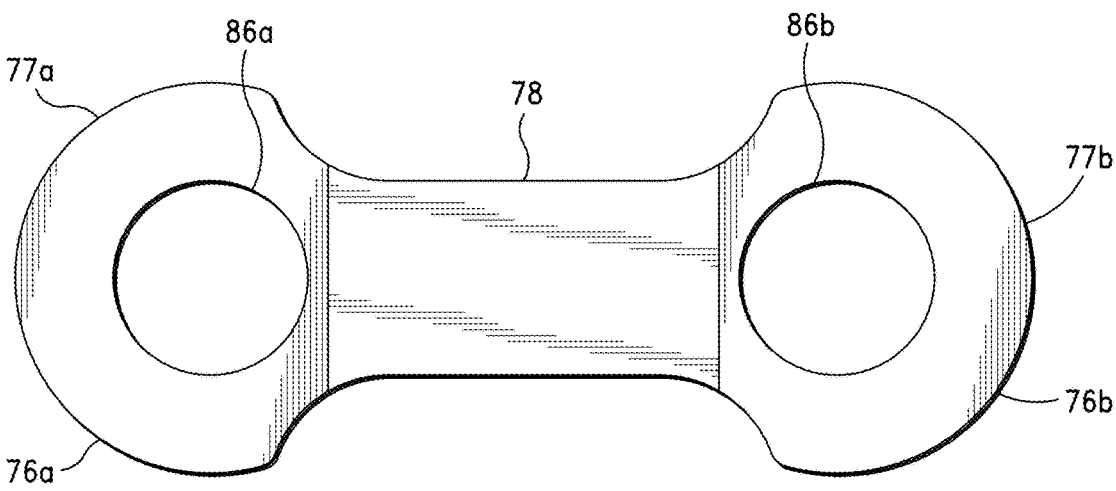
FIG. 10C is a rear plan view of the SI joint prosthesis shown in FIG. 10A, in accordance with the invention.
Figure 10D:
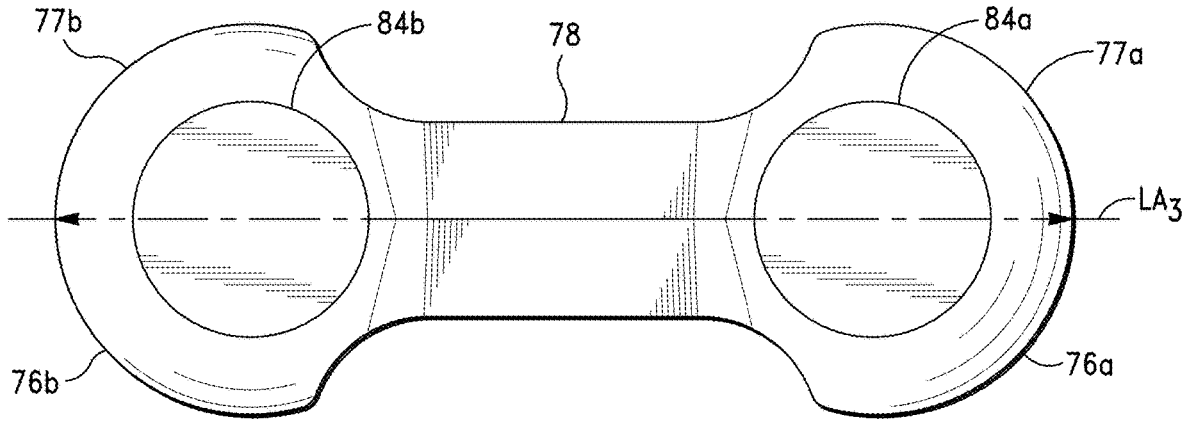
FIG. 10D is a front plan view of the SI joint prosthesis shown in FIG. 10A, in accordance with the invention.
Figures 10E, 10F:
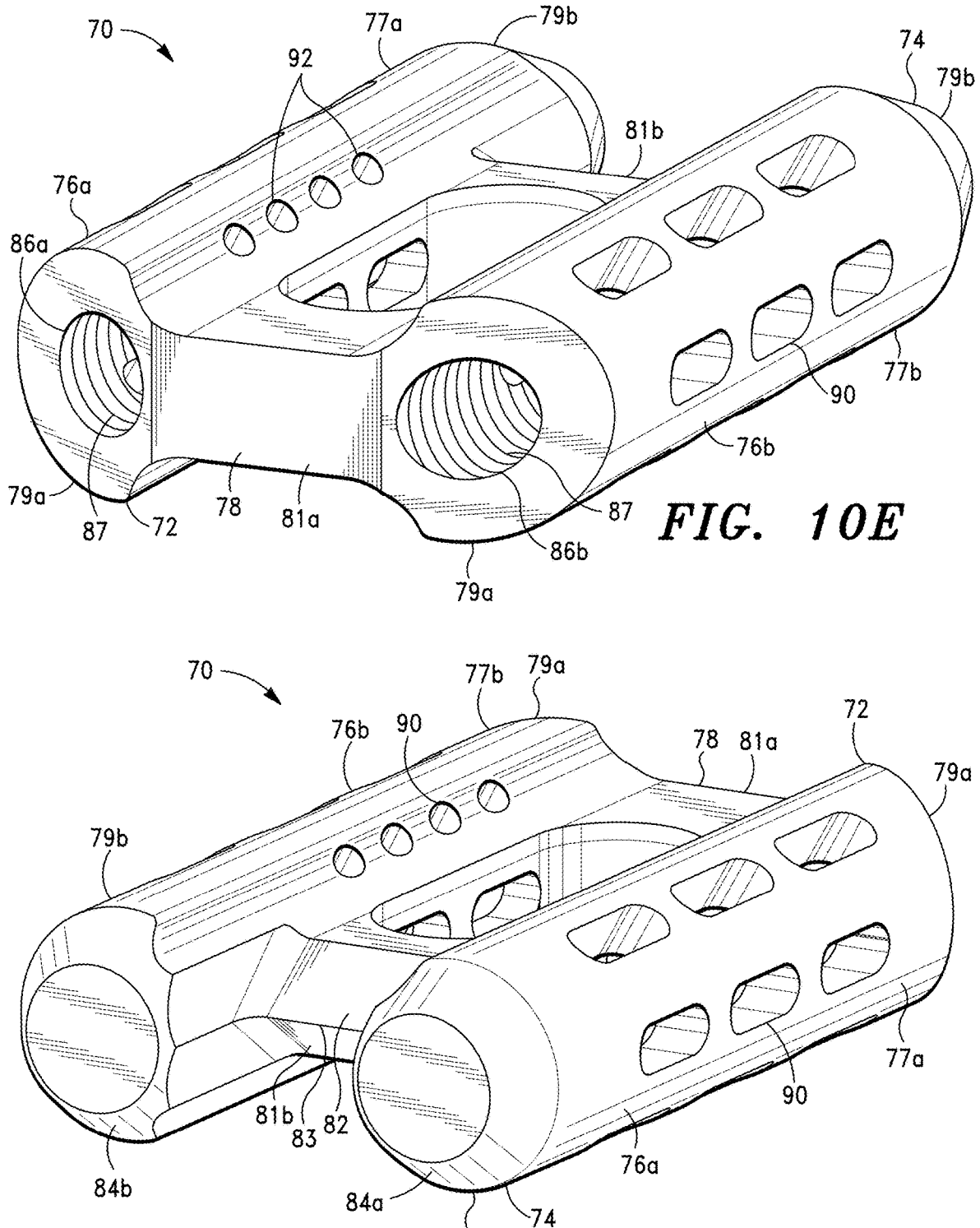
FIG. 10E is a rear perspective view of the SI joint prosthesis shown in FIG. 10A, in accordance with the invention.
FIG. 10F is a front perspective view of the SI joint prosthesis shown in FIG. 10A, in accordance with the invention.

As illustrated in FIGS. 10A, 10E, and 10F, the SI joint prosthesis 70 comprises a biocompatible and, hence, implantable member comprising proximal and distal ends 72, 74, and first and second elongated partially cylindrical sections 76a, 76b connected to a bridge section 78, whereby the SI joint prosthesis 70 comprises a continuous exterior surface comprising first and second partially cylindrical surface regions 77a, 77b.

As further illustrated in FIGS. 10A, 10E, and 10F, the first and second partially cylindrical sections 76a, 76b comprise proximal and distal ends 79a, 79b. The bridge section 78 similarly comprises proximal and distal ends 81a, 81b.

According to the invention, the SI joint prosthesis 70 can comprise any suitable length from the proximal ends 79a to the distal ends 79b of the partially cylindrical sections 76a, 76b. In some embodiments, the SI joint prosthesis 70 comprises a length in the range of 20-50 mm, more preferably, a length in the range of 30-40 mm.

As illustrated in FIGS. 10C, 10E, and 10F, and FIGS. 7A and 7B, the first partially cylindrical surface region 77a preferably comprises a partially cylindrical surface region shape that corresponds to at least a portion of the first lobe region 103 of the pilot SI joint opening 100 and/or the sacrum guide portion 203 of the pilot SI joint opening 200, and/or the second lobe region 104 of the pilot SI joint opening 100 and/or the ilium guide portion 204 of the pilot SI joint opening 200, depending on the entry position of the prosthesis 70 into the pilot SI joint openings 100, 200.

The second partially cylindrical surface region 77b similarly preferably comprises a partially cylindrical surface region shape that corresponds to at least a portion of the first lobe region 103 of the pilot SI joint opening 100 and/or the sacrum guide portion 203 of the pilot SI joint opening 200, or the second lobe region 104 of the pilot SI joint opening 100 and/or the ilium guide portion 204 of the pilot SI joint opening 200, again depending on the entry position of the prosthesis 70 into the pilot SI joint openings 100, 200.

As illustrated in FIGS. 10A, 10B, and 10F-10H, the distal end 81b of the bridge section 78 preferably comprises a taper region 82, which is configured and adapted to disrupt, i.e., cut into and through, articular cartilage and cortical bone 8 (and, in some aspects, trabecular bone 10), which define a SI joint.

According to the invention, the taper region 82 of the bridge section 78 can comprise various configurations including, without limitation, X-bevel, wedge-shaped or bevel, including top and bottom wedge bevels, Y-bevel, including top and bottom Y-bevels, and K-bevel configurations.

In some embodiments of the invention, the taper region 82 comprises two angled regions that intersect at a central point 83, i.e., pointed proximate the mid-region of the bridge section 78, such as shown in FIGS. 10A and 10F. In some embodiments, the taper region 82 comprises a single angled or sloped region defining a plane that intersects the plane defined by the bottom surface of the SI joint prosthesis 70, i.e., wedge shaped or bevel configuration.

In a preferred embodiment, the distal ends 79b of the first and second elongated partially cylindrical sections 76a, 76b also comprise tapered regions 84a, 84b, which facilitate (i) insertion of the distal ends 79b of the first and second elongated partially cylindrical sections 76a, 76b into the first and second lobe regions 103, 104 of the pilot SI joint opening 100 and/or the sacrum and ilium guide portions 203,

204 of the pilot SI joint opening 200, and (ii) as discussed in detail below, in some embodiments, transition of the pilot SI joint opening 100 from a first configuration and size (and, hence, cross-sectional area, i.e., $A^2_i$-1 shown in FIG. 7A) to a second expanded configuration and size (and, hence, cross-sectional area, i.e., $A^2_i$-4 shown in FIG. 12A) when the SI joint prosthesis 70 is inserted therein, and transition of the sacrum and ilium guide portions 203, 204 of pilot SI opening 200 from first configurations and sizes (and, hence, cross-sectional areas, i.e., $A^2_i$-2 and $A^2_i$-3 shown in FIG. 7B) to expanded second configurations and sizes (and, hence, cross-sectional areas, i.e., $A^2_i$-5 and $A^2_i$-6 shown in FIG. 12B) when the SI joint prosthesis 70 is inserted therein.

Figures 10G, 10H:
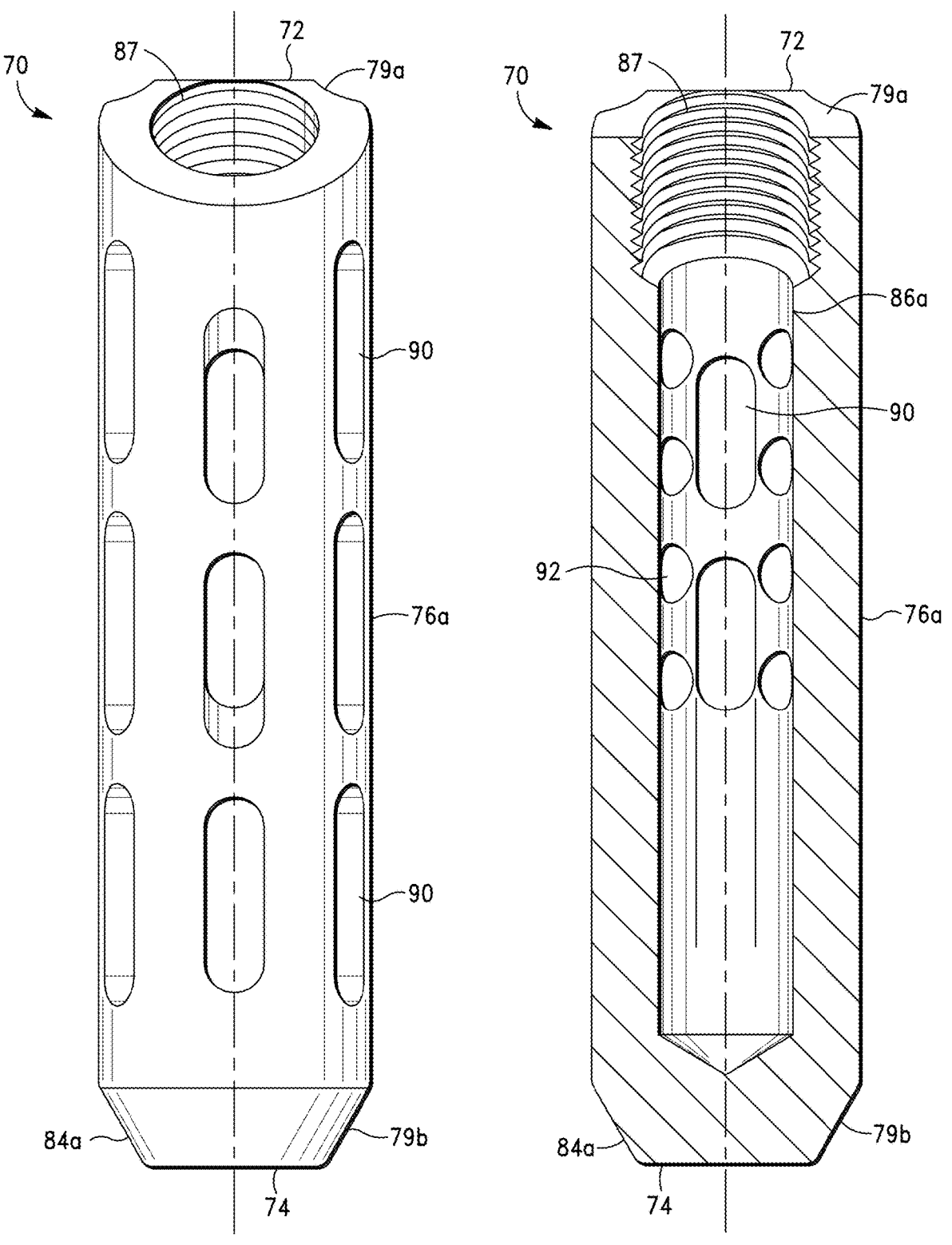
FIG. 10G is a right-side plan view of the SI joint prosthesis shown in FIG. 10A, in accordance with the invention.
FIG. 10H is a right-side sectional plan view of the SI joint prosthesis shown in FIG. 10A, in accordance with the invention.

As illustrated in FIGS. 10C, 10E, and 10H, the first elongated partially cylindrical section 76a of the SI joint prosthesis 70 comprises an internal prosthesis engagement member lumen 86a that extends from the proximal end 79a of the first elongated partially cylindrical section 76a.

As illustrated in FIGS. 10C and 10E, the second elongated partially cylindrical section 76b of the SI joint prosthesis 70 also comprises an internal prosthesis engagement member lumen 86b that extends from the proximal end 79a of the first elongated partially cylindrical section 76b.

In a preferred embodiment, the internal prosthesis engagement member lumens 86a, 86b of the SI joint prosthesis 70 are sized and configured to receive the prosthesis guide pins 606 of the prosthesis deployment assemblies 600a, 600b, discussed below, and the prosthesis engagement rod 700 of the prosthesis deployment assemblies 600a, 600b.

Figures 8C, 8D, 8E:
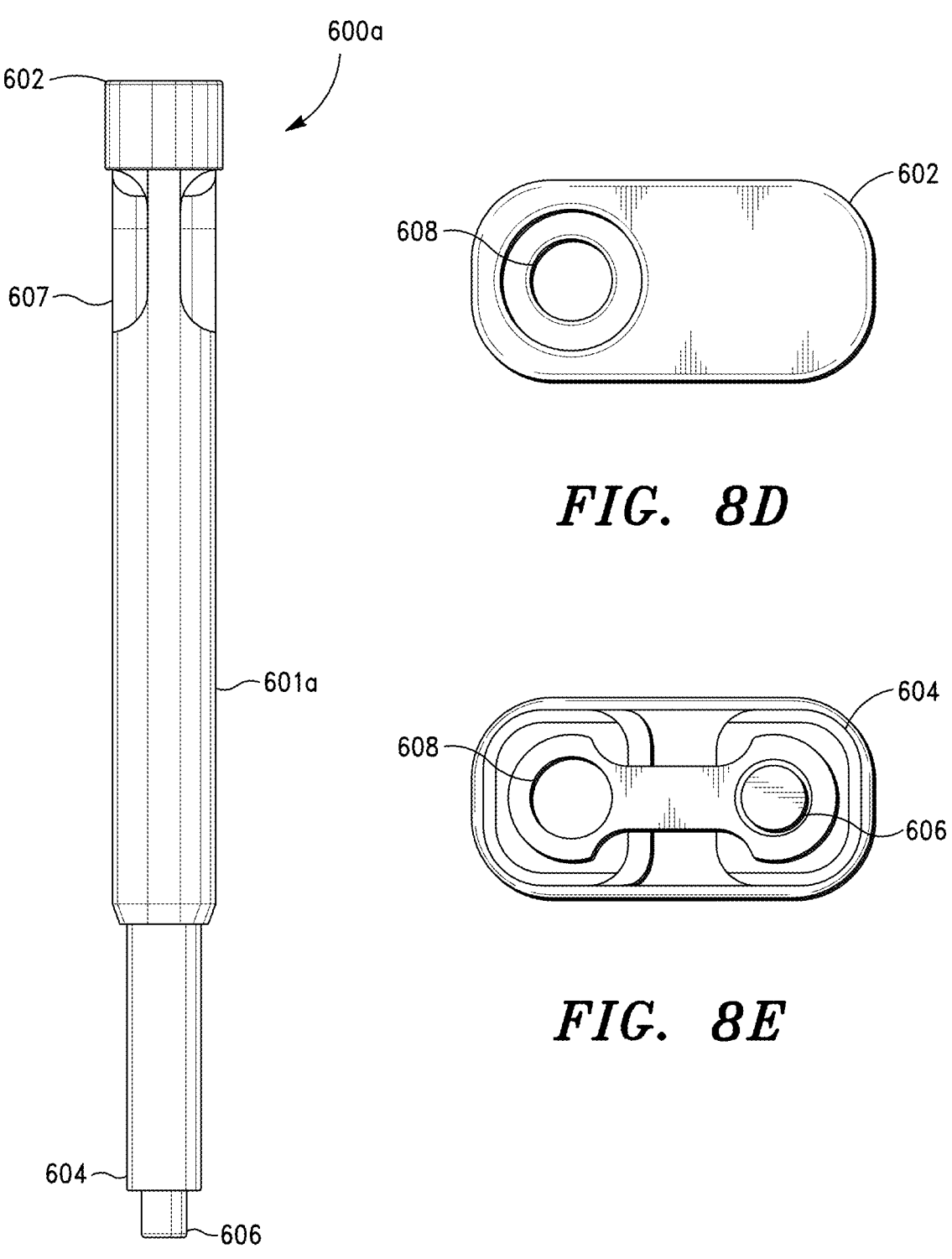
FIG. 8C is a left-side plan view of the prosthesis deployment assembly shown in FIG. 8A, in accordance with the invention.
FIG. 8D is a top plan view of the prosthesis deployment assembly shown in FIG. 8A, in accordance with the invention.
FIG. 8E is a bottom plan view of the prosthesis deployment assembly shown in FIG. 8A, in accordance with the invention.
Figure 9B:
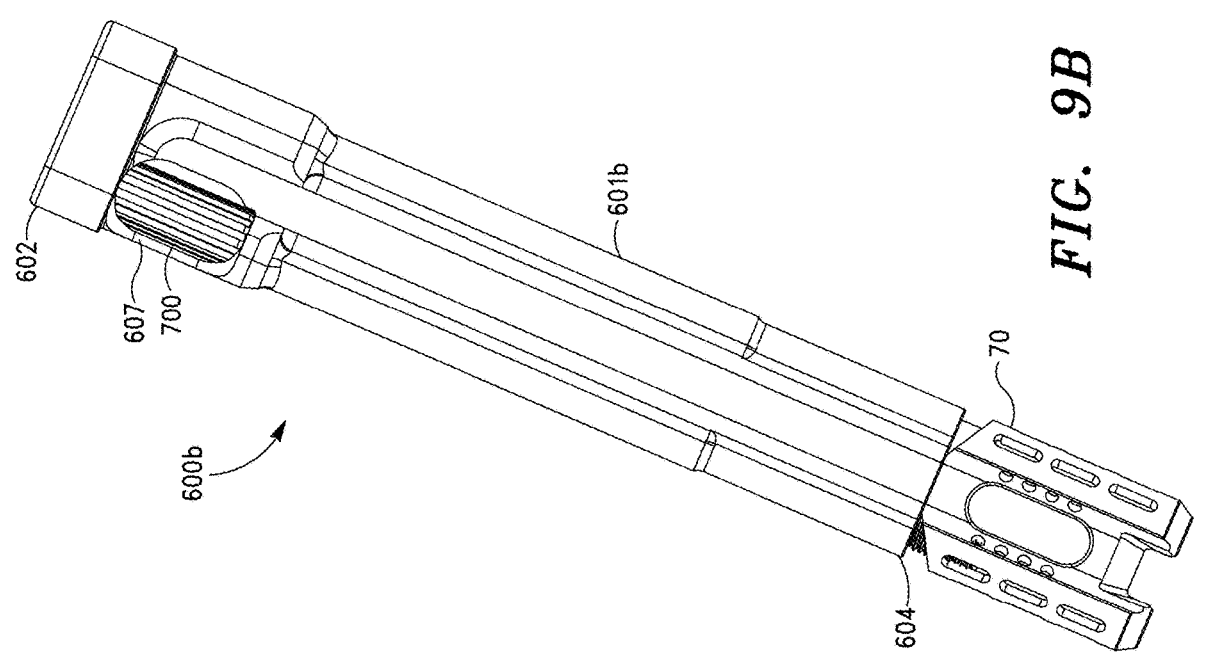
FIG. 9B is a perspective view of the prosthesis deployment assembly shown in FIG. 9A engaged to a prosthesis of the invention, in accordance with the invention.

As illustrated in FIGS. 10E and 10G, in a preferred embodiment, the internal prosthesis engagement member lumens 86a, 86b of the first and second elongated partially cylindrical sections 76a, 76b comprise a threaded region 87 proximate the proximal end 79a that is sized and configured to receive and threadably engage the threaded distal end 704 of the prosthesis engagement rod 700 of the prosthesis deployment assemblies 600a, 600b (see FIGS. 8F, 8G, and 9B).

In a preferred embodiment, the internal prosthesis engagement lumens 86a, 86b are also configured to receive agents and compositions that further facilitate adhesion of the SI joint prosthesis 70 to the pilot SI openings 100, 200 of the invention and, thereby, sacrum and/or ilium, and the aforementioned biologically active agents and compositions, including osteogenic agents and compositions, and pharmacological agents and compositions that facilitate osseous or bone tissue ingrowth into the SI joint prosthesis 70 and healing of the SI joint bone structures.

Referring back to FIGS. 10A and 10B, in a preferred embodiment, the SI joint prosthesis 70 further comprises a plurality of slots 90 and holes 92, which preferably are in communication with the internal prosthesis engagement member lumens 86a, 86b.

In a preferred embodiment, the agents and compositions referenced above are adapted to extrude through the slots 90 and holes 92 of the SI joint prosthesis 70 when the SI joint prosthesis 70 is inserted in a pilot SI joint opening (i.e., pilot SI joint openings 100 or 200), to, as indicated above, (i) further facilitate adhesion of the SI joint prosthesis 70 to the pilot SI openings 100, 200 of the invention and, thereby, sacrum and/or ilium, and (ii) facilitate osseous or bone tissue ingrowth into the SI joint prosthesis 70 and healing of the SI joint bone structures.

Figure 10I:
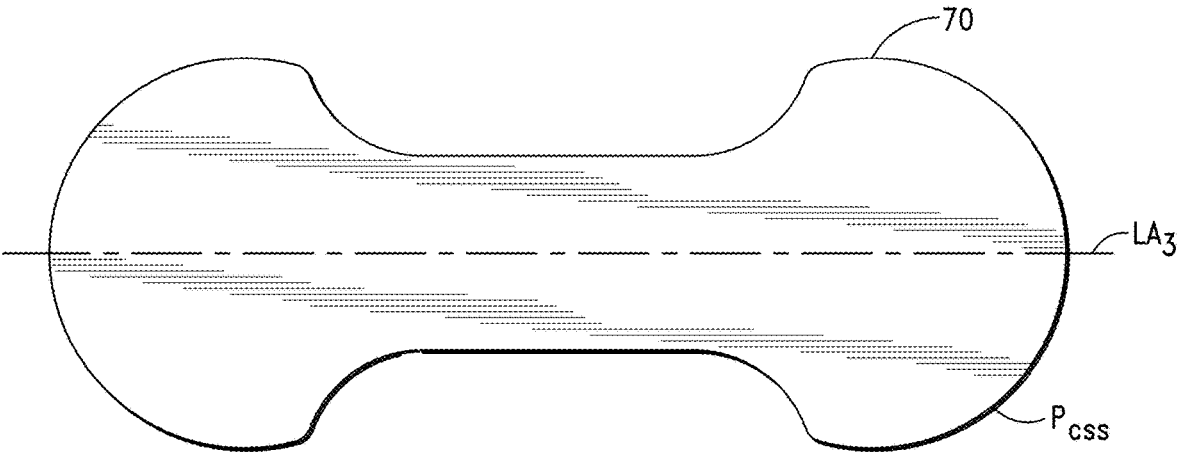
FIG. 10I is another rear plan view of the SI joint prosthesis shown in FIG. 10A showing the cross-sectional shape defined by the outer surface of the prosthesis, in accordance with the invention.

Referring now to FIG. 10I, according to the invention, the continuous exterior surface of the SI joint prosthesis 70, which is illustrated in FIGS. 10C and 10D, defines a substantially bi-lobe prosthesis cross-sectional shape (denoted "$P_{CSS}$") having a longitudinal axis $LA_3$.

Figure 11A:
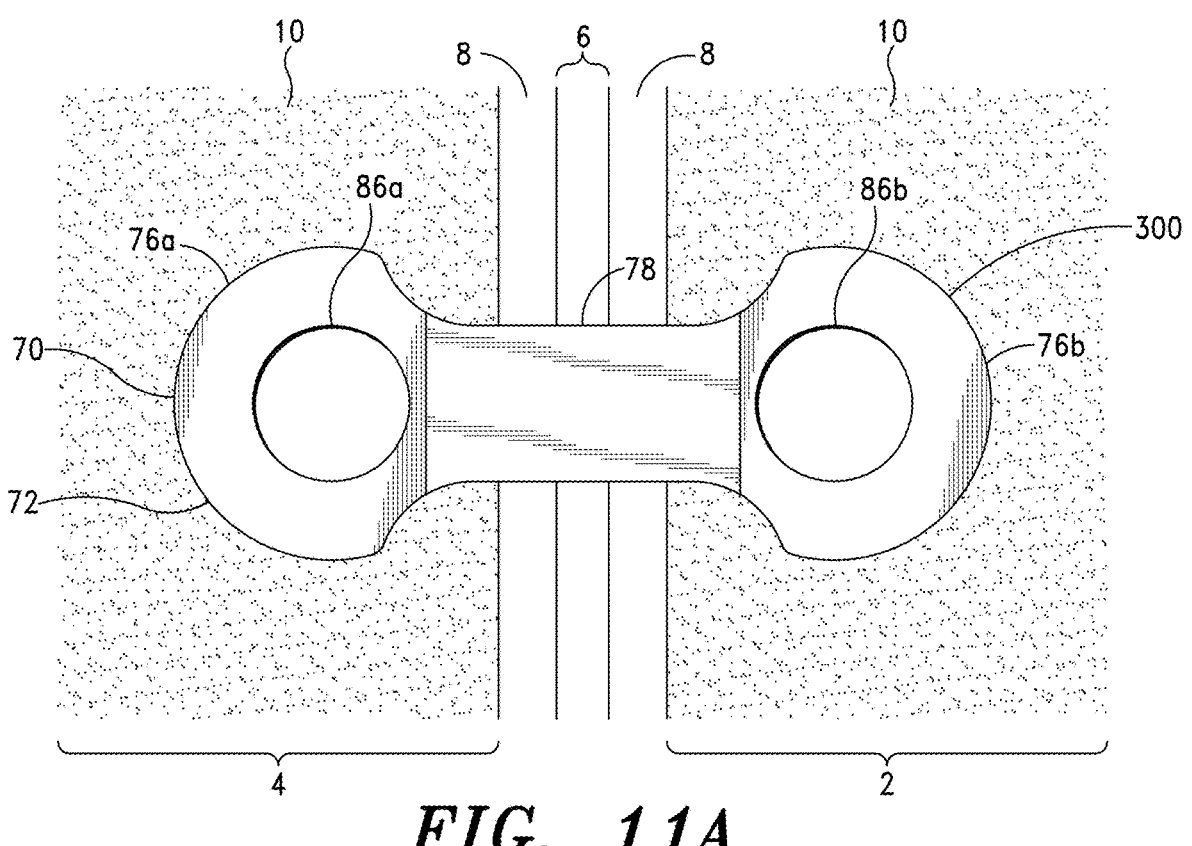
FIG. 11A is an illustration of the SI joint prosthesis shown in FIG. 10A inserted into the pilot SI joint opening shown in FIG. 7A and the resulting or induced post-prosthesis insertion SI joint opening, in accordance with the invention.

As set forth in Co-pending U.S. application Ser. No. 17/463,779, according to one embodiment of the invention, the length of the prosthesis cross-sectional shape $P_{CCS}$ along longitudinal axis $LA_3$ is greater than the length of the pilot SI joint opening 100, i.e., cross-sectional shape thereof illustrated in FIG. 7A, along the longitudinal axis $LA_2$ thereof, whereby, when the SI joint prosthesis 70 is inserted into pilot SI joint opening 100, as illustrated in FIG. 11A, the pilot SI opening 100 transitions to a post-prosthesis insertion SI joint opening 300 comprising a larger cross-sectional length shape that corresponds to the length of the prosthesis cross-sectional shape $P_{CCS}$.

Figure 12A:
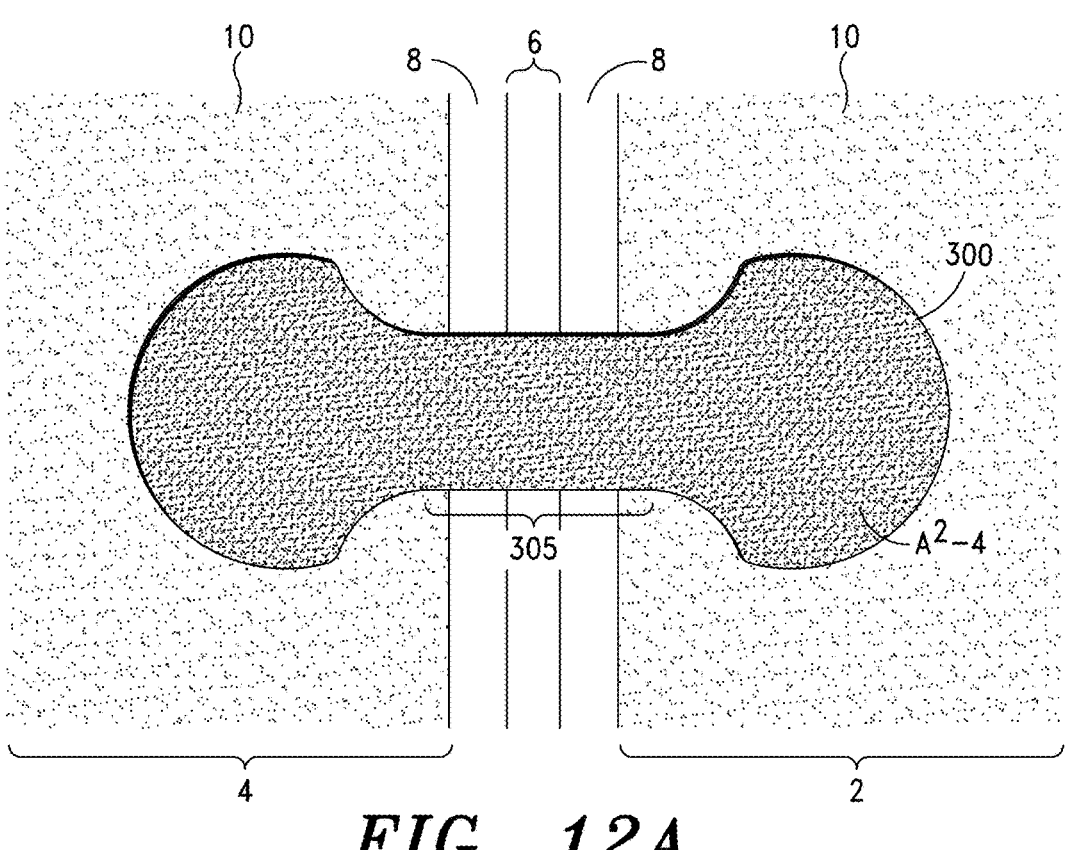
FIG. 12A is an illustration of the post-prosthesis insertion SI joint opening generated or induced when the SI joint prosthesis shown in FIG. 10A is inserted in the pilot SI joint opening shown in FIG. 7A, in accordance with the invention.

As illustrated in FIG. 12A, in a preferred embodiment, when the SI joint prosthesis 70 is inserted into pilot SI joint opening 100, the cross-sectional area of the post-prosthesis insertion SI joint opening 300 also comprises a cross-sectional area (denoted "$A^2$-4") that is greater than the cross-sectional area $A^2_i$-1 of the pilot SI joint opening 100.

As further illustrated in FIG. 12A, the noncircular region 105 of pilot SI joint opening 100 also transitions to a much larger noncircular region (denoted "305"), which is achieved by virtue of the tapered bridge section 78 of the SI joint prosthesis 70 cutting into and through the articular cartilage and cortical bone 8, which define the SI joint 6, and the trabecular bone 10 proximate the SI joint 6.

Figure 11B:
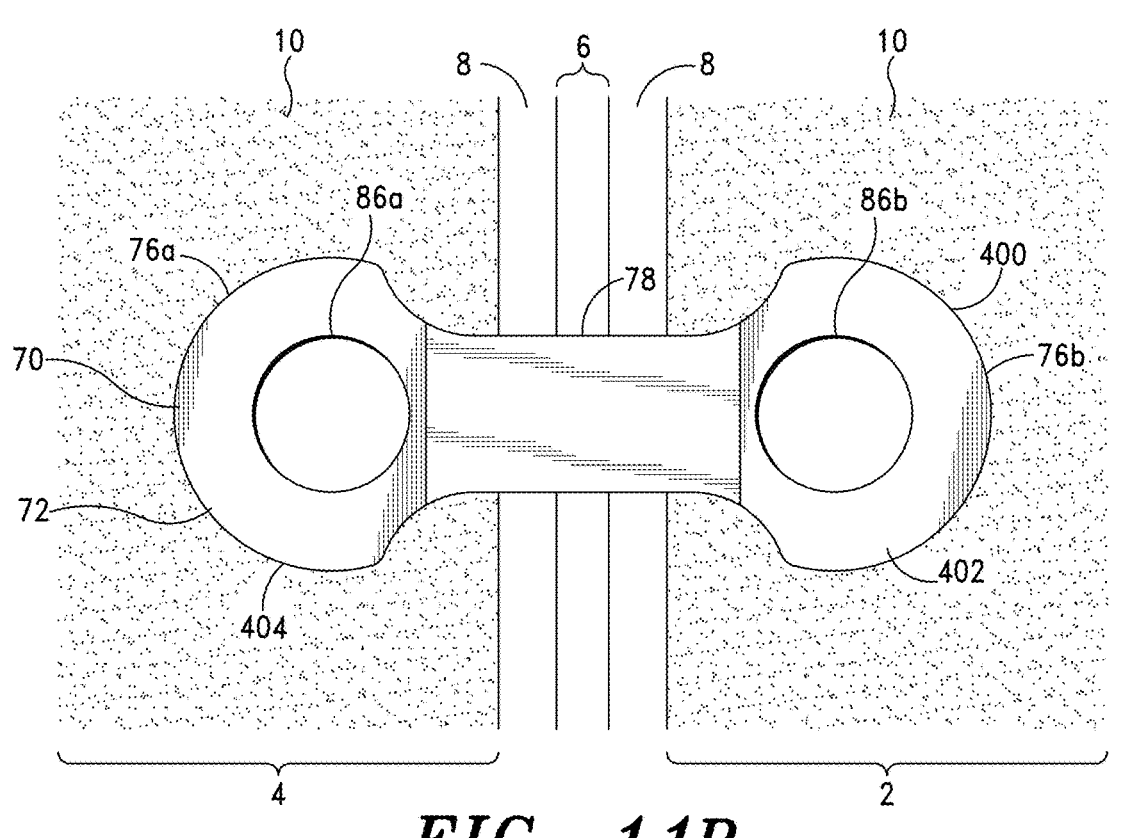
FIG. 11B is an illustration of the SI joint prosthesis shown in FIG. 10A inserted in the pilot SI joint opening shown in FIG. 7B and the resulting or induced post-prosthesis insertion SI joint opening, in accordance with the invention.
Figure 12B:
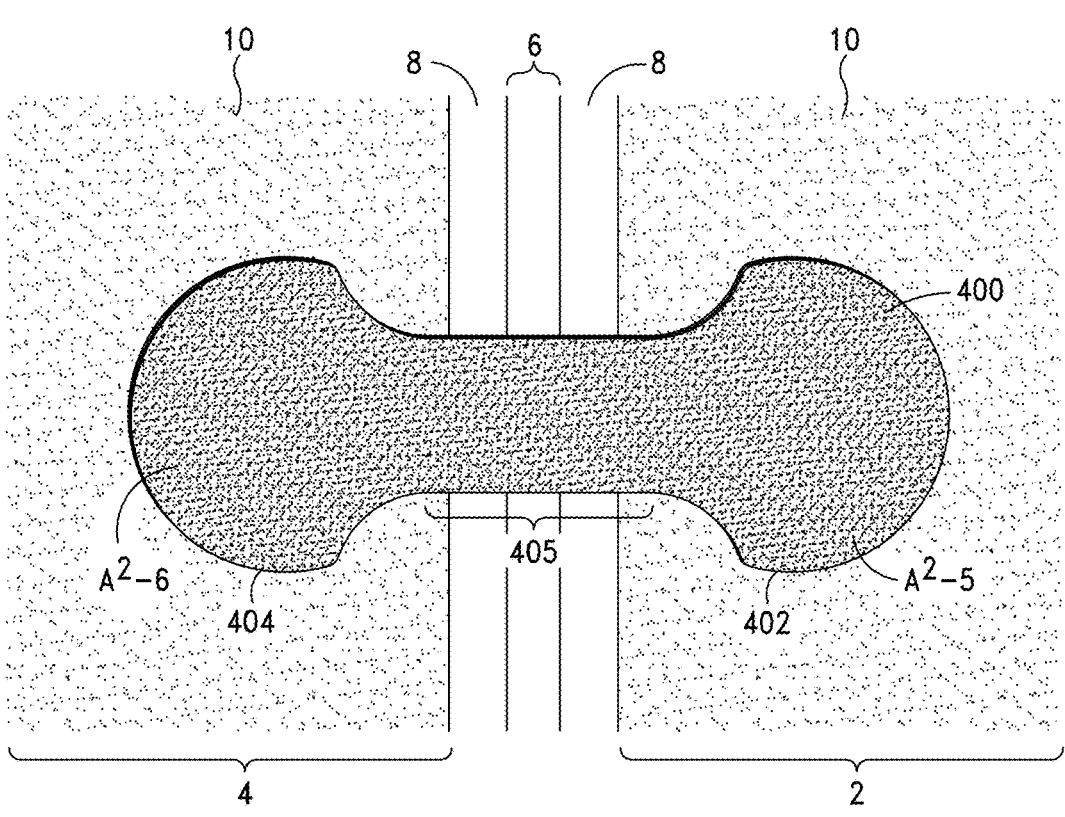
FIG. 12B is an illustration of the post-prosthesis insertion SI joint opening generated or induced when the SI joint prosthesis shown in FIG. 10A is inserted in the pilot SI joint opening shown in FIG. 7B and/or 7C, in accordance with the invention.

According to the noted embodiment of the invention, when the SI joint prosthesis 70 is inserted into pilot SI joint opening 200, as illustrated in FIG. 11B, the pilot SI joint opening 200 similarly transitions to a post-prosthesis insertion SI joint opening 400, wherein, as illustrated in FIG. 12B, the cross-sectional areas of the post-prosthesis sacrum and ilium guide portions of the post-prosthesis insertion SI joint opening 400 (now denoted "402" and "404", respectively) comprise greater cross-sectional areas (denoted "$A^2$-5" and "$A^2$-6").

As further illustrated in FIG. 12B, the post-prosthesis insertion SI joint opening 400 also comprises a noncircular region (denoted "405"), which is similarly achieved by virtue of the tapered bridge section 78 of the SI joint prosthesis 70 cutting into and through the articular cartilage and cortical bone 8, which define the SI joint 6, and the trabecular bone 10 proximate the SI joint 6.

As illustrated in FIGS. 10I, 12A and 12B, the post-prosthesis insertion SI joint openings 300, 400 also preferably comprise cross-sectional shapes that correspond to the prosthesis cross-sectional shape "$P_{CSS}$" defined by the outer surface of the SI joint prosthesis 70, including the first and second elongated partially cylindrical sections 76a, 76b and bridge section 78.

In a preferred embodiment of the invention, to achieve sufficient expansion of the pilot SI joint openings 100, 200 when the SI joint prosthesis 70 is inserted therein, preferably, the cross-sectional areas of the regions defined by the first and second elongated partially cylindrical sections 76a, 76b of the SI joint prosthesis 70 are at least 0.05% greater than the cross-sectional areas defined by the first and second lobe regions 103, 104 of the pilot SI joint opening 100, and the cross-sectional areas defined by the sacrum and ilium guide portions 203, 204 of pilot SI joint opening 200.

In some embodiments of the invention, the cross-sectional areas of the regions defined by the first and second elongated partially cylindrical sections 76a, 76b of the SI joint prosthesis 70 are substantially equal to or slightly smaller, e.g., <0.05%, than the cross-sectional areas defined by the first and second lobe regions 103, 104 of the pilot SI joint opening 100, and the cross-sectional areas defined by the sacrum and ilium guide portions 203, 204 of pilot SI joint opening 200.

As set forth in Co-pending U.S. application Ser. No. 17/463,779, the SI joint prosthesis 70 can comprise various biocompatible materials, including metals and metal alloys, such as titanium, stainless-steel, cobalt-chromium alloys and nickel-titanium alloys, and various biocompatible polymers, including, without limitation, reinforced polymers, such as carbon fiber reinforced polymers and metal-framed polymers.

The SI joint prosthesis 70 can additionally comprise a porous structure to facilitate (i) adhesion of the prosthesis 70 to a post-prosthesis insertion SI joint opening of the invention; particularly, post-prosthesis insertion SI joint openings 300, 400 and, thereby, to SI joint bone structures, i.e., sacrum and ilium bone structures, and (ii) bone or osseous tissue ingrowth into the prosthesis 70.

The SI joint prosthesis 70 can further comprise various exterior surface textures and roughness to facilitate or enhance engagement of the prosthesis to a post-prosthesis insertion SI joint opening, such as post-prosthesis insertion SI joint openings 300, 400, and, thereby, to SI joint bone structures, i.e., sacrum and ilium bone structures, and/or maintain engagement thereto and positioning therein.

The surface of the SI joint prosthesis 70 can, thus, comprise a roughness grade number of N1 (Ra=~0.025 μm), N2 (Ra=~0.05 μm), N3 (Ra=~0.1 μm), N4 (Ra=~0.2 μm), N5 (Ra=~0.4 μm), N6 (Ra=~0.08 μm), N7 (Ra=~1.6 μm), N8 (Ra=~3.2 μm), N9 (Ra=~6.3 μm), N10 (Ra=~12.5 μm), N11 (Ra=~25 μm), or N12 (Ra=~50 μm).

In some embodiments of the invention, the SI joint prosthesis comprises an outer coating.

In some embodiments, the outer coating comprises one of the aforementioned osteogenic compositions.

In some embodiments, the osteogenic composition comprises a demineralized bone matrix, autograft bone material, allograft bone material, xenograft bone material, polymethyl-methacrylate or calcium-based bone material.

In some embodiments, the osteogenic composition comprises a bone morphogenic protein (BMP).

In some embodiments, the BMP comprises BMP-1, BMP2a, BMP2b, BMP3, BMP4, BMP5, BMP6, BMP7, or BMP8a.

In some embodiments, the outer coating comprises one of the aforementioned biologically active agents.

In some embodiments, the biologically active agent comprises a basic fibroblast growth factor (bFGF), a transforming growth factor-β(TGF-β), a vascular endothelial growth factor (VEGF), a platelet derived growth factor (PDGF), an insulin-like growth factor (IGF), an epidermal growth factor (EGF), or a growth and differentiation factor-5 (GDF-5).

In some embodiments, the outer coating comprises one of the aforementioned pharmacological agents.

In some embodiments, the pharmacological agent comprises penicillin, a carboxypenicillin, a tetracycline, gentamicin, vancomycin, ciprofloxacin, amikacin, an aminoglycoside, a cephalosporin, clindamycin, erythromycin, a fluoroquinolone, a macrolide, an azolide, metronidazole, trimethoprim-sulfamethoxazole, polymyxin B, oxytetracycline, tobramycin, cefazolin, or rifampin.

In some embodiments, the pharmacological agent comprises dexamethasone, betamethasone, prednisone, prednisolone, methylprednisolone sodium succinate, methylprednisolone, cortisone, ketorolac, diclofenac, or ibuprofen.

In some embodiments of the invention, the outer coating comprises a biocompatible adhesive composition.

According to the invention, suitable adhesive compositions include, without limitation, poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol and combinations thereof; fibrin-based compositions, collagen-based compositions, including collagen and poly(L-glutamic acid) compositions; albumin-based compositions, including Bio-Glue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and radiation curable materials, such as poly (glycerol-co-sebacate) acrylate (PGSA), discussed below.

In some embodiments, the outer coating comprises one of the aforementioned polymers and/or compositions comprising same.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

PGS and derivatives thereof possess a unique property of inducing remodeling of damaged osseous or bone tissue, such as at pilot SI joint openings, and, hence, healing of the associated bone structures when disposed proximate thereto.

As set forth in Loh, et al., *Poly(glycerol sebacate) Biomaterial: Synthesis and Biomedical Applications*, Journal of Materials Chemistry B, vol. 3(39), pp. 7641-7652 (2015) and indicated in Table 1 below, a further seminal property of PGS is that its physical state can be modulated during synthesis by controlling the "degree of esterification" via at least one crosslinking agent, e.g., methylene diphenyl diisocyanate (MDI).

TABLE 1

| Degree of Esterification | Physical State |
| --- | --- |
| ≤46% | Solid (Brittle Wax) |
| ~47%-64% | Semi-Solid (Soft Wax) |
| ~65%-75% | Viscous Liquid |
| ~76%-83% | Sticky Elastomer |
| ≥84% | Elastomer |

According to the invention, any suitable degree of esterification of PGS can be employed for PGS when employed in or for PGS based outer coatings (i.e., polymer compositions comprising PGS) and biologically active agent compositions of the invention.

In some embodiments, the PGS based outer coatings comprise a degree of esterification in the range of ~76%-83%, whereby the PGS exhibits adhesive properties, which will enhance engagement of prosthesis 70 (as well as the prostheses disclosed in Co-pending priority application Ser. No. 13/857,977) to the post-prosthesis insertion SI joint openings 300, 400 and, thereby, to the SI joint bone structures, i.e., sacrum and ilium bone structures.

As is well established, the physical state of poly(glycerol-co-sebacate) acrylate (PGSA) can also be modulated by combining the PGSA with a suitable photoinitiator and subjecting the PGSA to radiation.

Indeed, as set forth in Nijst, et al., *Synthesis and Characterization of Photocurable Elastomers from Poly(Glycerol-Co-Sebacate)*, Biomacromolecules, vol. 8, no. 10, pp. 3067-3073 (2007), PGSA can be induced to transition from a liquid or flowable state to a solid elastomer state when combined with a photoinitiator, such as 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl and methylcyclopentadienyl manganese tricarbonyl, and subjected to radiation, such as visible light; particularly, radiation in the range of approximately 380-750 nm, and ultraviolet (UV) light, particularly, radiation in the range of 10-400 nm.

Thus, in some embodiments, a composition comprising PGSA (also referred to herein as a "PGSA based composition") is employed to enhance the engagement of the SI joint prosthesis 70 to a post-prosthesis insertion SI joint opening, such as post-prosthesis insertion SI joint openings 300, 400, and, thereby, SI joint bone structures, i.e., sacrum and ilium bone structures.

As set forth in Co-pending U.S. application Ser. No. 17/463,779, in such embodiments, the PGSA based composition (in a flowable state) is disposed in the internal prosthesis engagement member lumens 86a, 86b of the SI joint prosthesis 70, whereby the PGSA based composition is dispersed when the SI joint prosthesis 70 is positioned in the dysfunctional SI joint and fills any gaps between the prosthesis 70 and a post-prosthesis insertion SI joint opening of the invention; particularly, post-prosthesis insertion SI joint openings 300, 400, and thereafter cured via radiation and solidified, whereby the solidified PGSA enhances the engagement of the prosthesis 70 to the post-prosthesis insertion SI joint opening and, thereby, to the sacrum and ilium bone structures.

As further set forth in Co-pending U.S. application Ser. No. 17/463,779, PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS outer coatings and PGS and PGSA based compositions further comprise one or more of the aforementioned biologically active or pharmacological agents.

Prosthesis Deployment Assembly

Referring now to FIGS. 8A-8G, there is shown one embodiment of a prosthesis deployment assembly of the invention (denoted "600a").

As illustrated in FIG. 8G, in a preferred embodiment, the prosthesis deployment assembly 600a comprises prosthesis engagement means that is configured and adapted to connect the prosthesis deployment assembly 600a to SI joint prostheses of the invention; particularly, SI joint prosthesis 70 shown in FIG. 8G, and guide the prostheses into pilot SI joint openings created by the drill guide assemblies 500a, 500b, 500c.

As illustrated in FIGS. 8A-8C, the prosthesis deployment assembly 600a comprises an elongated guide member 601a comprising proximal and distal ends 602, 604.

As further illustrated in FIGS. 8B and 8E, the elongated guide member 601a further comprises a prosthesis guide pin 606 that extends from the guide member distal end 604. As indicated above and shown in FIG. 8G, the prosthesis guide pin 606 is sized and configured to seat in an internal prosthesis engagement member lumen 86a or 86b of the preferred SI joint prosthesis 70 of the invention.

As illustrated in FIGS. 8A, 8D, and 8E, the elongated guide member 601a further comprises an internal lumen 608 that extends from the proximal end 602 of the elongated guide member 601 to the distal end 604 of the elongated guide member 601a.

As illustrated in FIG. 8G, in a preferred embodiment of the invention, the internal lumen 608 is sized and configured to receive the prosthesis engagement rod 700 (i.e., prosthesis engagement means) of the prosthesis deployment assembly 600a (and prosthesis deployment assembly 600b, discussed below).

Referring now to FIG. 8F, there is shown a preferred embodiment of a prosthesis engagement rod 700 of the invention. As illustrated in FIG. 8F, the prosthesis engagement rod 700 comprises a proximal end 702 and a threaded distal end 704, which is sized and configured to threadably engage an internal prosthesis engagement member lumen of a SI joint prosthesis of the invention, e.g., internal prosthesis engagement member lumens 86a and/or 86b of prosthesis 70.

As further illustrated in FIG. 8F, in a preferred embodiment, the proximal end 702 of the prosthesis engagement rod 700 comprises a knurled configuration to facilitate threading the prosthesis engagement rod 700 into an internal prosthesis engagement member lumen of a SI joint prosthesis of the invention, e.g., prosthesis 70.

Referring back to FIGS. 8A and 8B, to further facilitate threading the prosthesis engagement rod 700 into an internal prosthesis engagement member lumen of a SI joint prosthesis of the invention, in a preferred embodiment, the elongated guide member 600a (and prosthesis deployment assembly 600b) further comprises an access port 607 that provides access to the knurled proximal end 602 of the prosthesis engagement rod 700 when positioned in the internal lumen 608 of the elongated guide member 601a, as shown in FIG. 8G, and elongated guide member 601b, as shown in FIG. 9B.

Figure 9A:
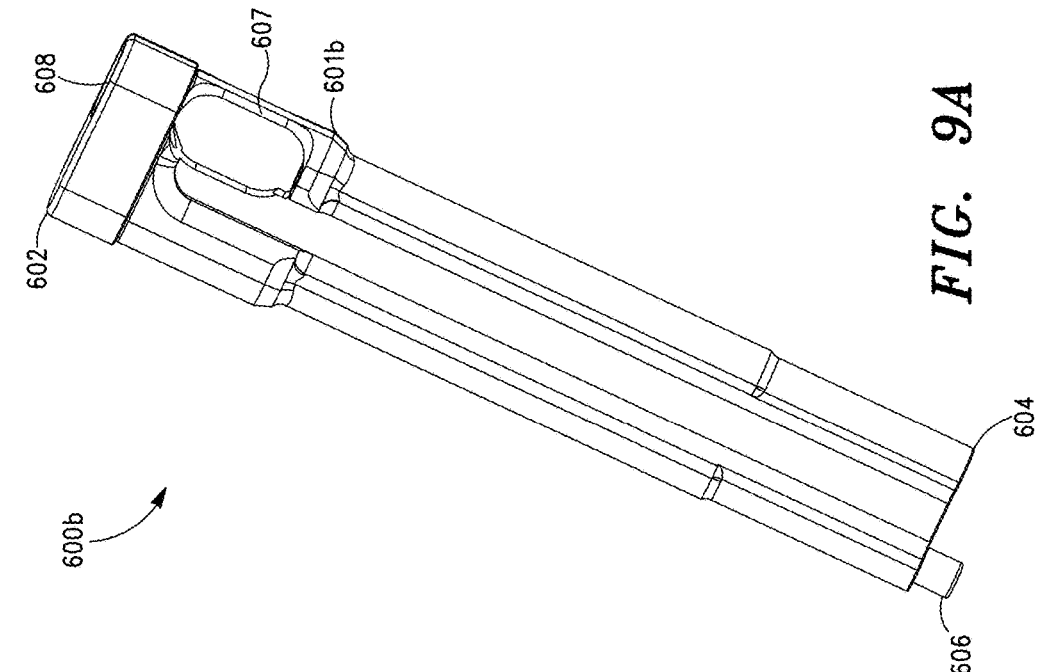
FIG. 9A is a perspective view of another embodiment of a prosthesis deployment assembly, in accordance with the invention.

Referring now to FIGS. 9A and 9B, there is shown another embodiment of a prosthesis deployment assembly of the invention (denoted "600b").

As illustrated in FIG. 9A, in a preferred embodiment, the prosthesis deployment assembly 600b is similarly configured and adapted to connect to SI joint prostheses of the invention; particularly, SI joint prosthesis 70 shown in FIGS. 10A-10I, and guide the prostheses into pilot SI joint openings created by the drill guide assemblies 500a, 500b, 500c.

As illustrated in FIGS. 9A and 9B, the prosthesis deployment assembly 600b similarly comprises an elongated guide member (denoted 601b in this embodiment) comprising proximal and distal ends 602, 604, prosthesis guide pin 606, internal lumen 608, access port 607, and prosthesis engagement rod 700.

As illustrated in FIGS. 9A and 9B, in this embodiment, the elongated guide member 601b has a narrower body that preferably comprises a cross-sectional shape that corresponds to the cross-sectional shapes of the SI joint prosthesis 70 and the prosthesis internal access opening 560 in the drill guide assembly 500c, whereby the elongated guide member 601b (and, hence, prosthesis 70 engaged thereto) can be readily received and positioned in the prosthesis internal access opening 560 in the drill guide assembly 500c, as shown in FIGS. 5F and 5G.

Figure 13A:
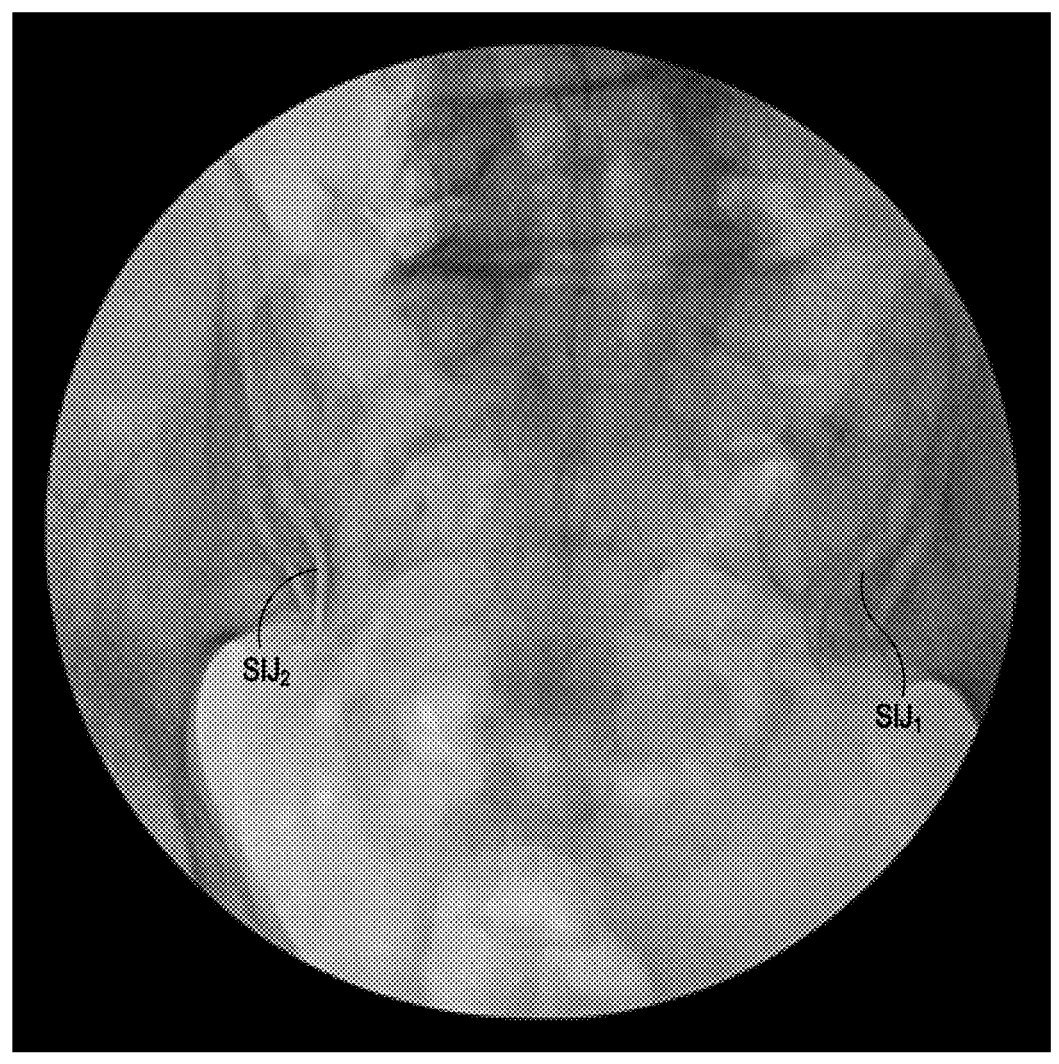
FIG. 13A is a conventional computed tomography (CT) scan image showing an anteroposterior (AP) view of a pelvic structure and SI joints associated therewith.
Figure 13B:
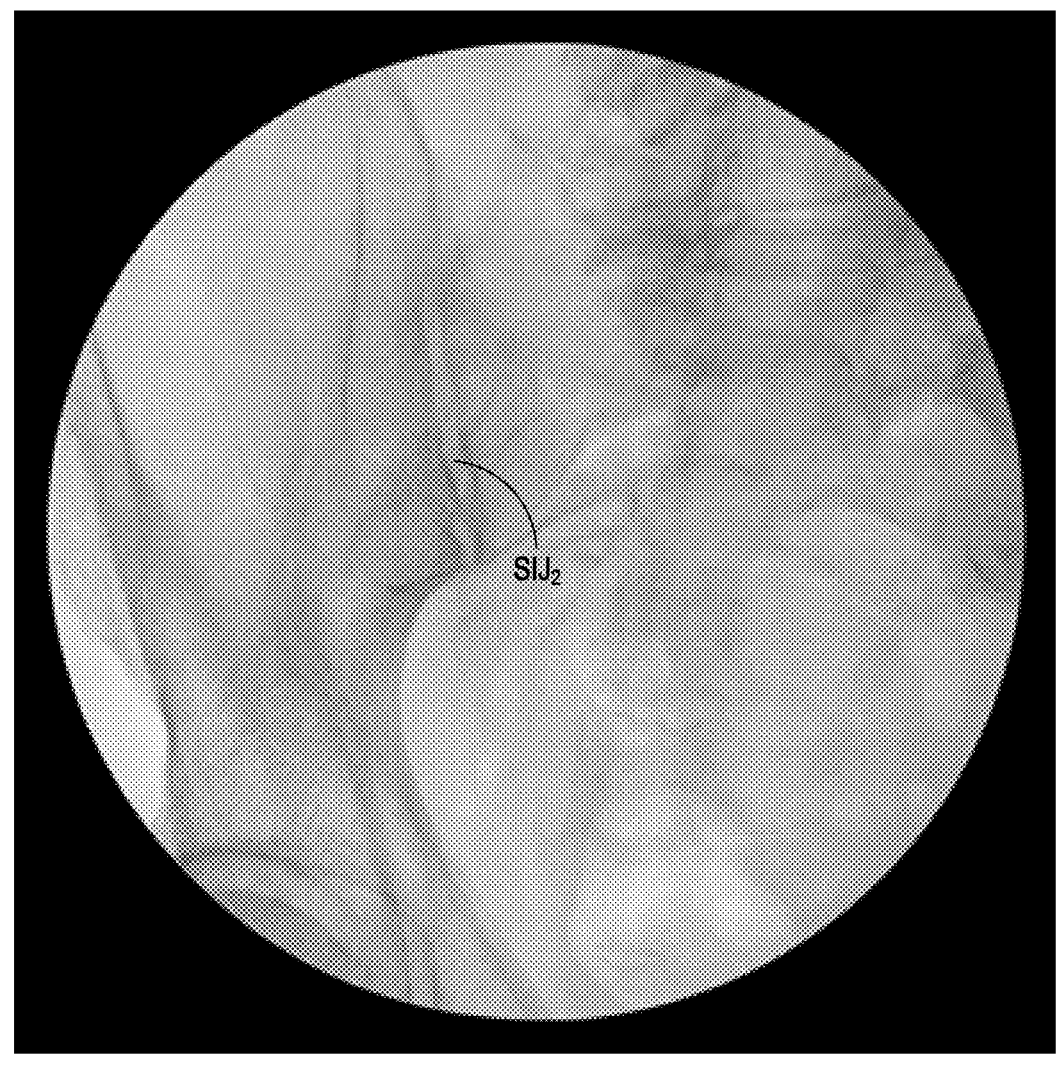
FIG. 13B is a CT scan image showing a modified AP view of a dysfunctional SI joint, in accordance with the invention.
Figure 13C:
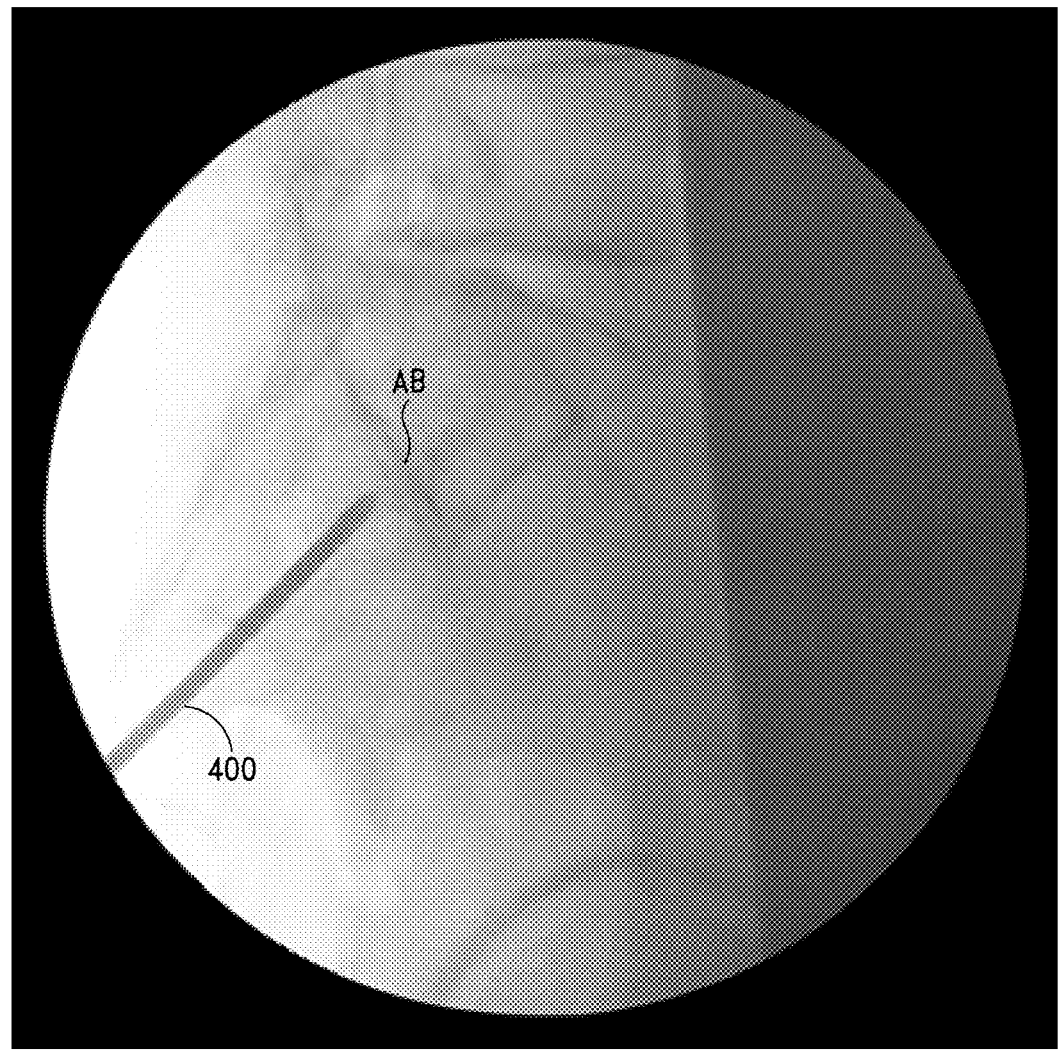
FIG. 13C is a CT scan image showing a tangent lateral view of the dysfunctional SI joint shown in FIG. 13B, showing a guide pin properly positioned therein, in accordance with the invention.
Figure 13D:
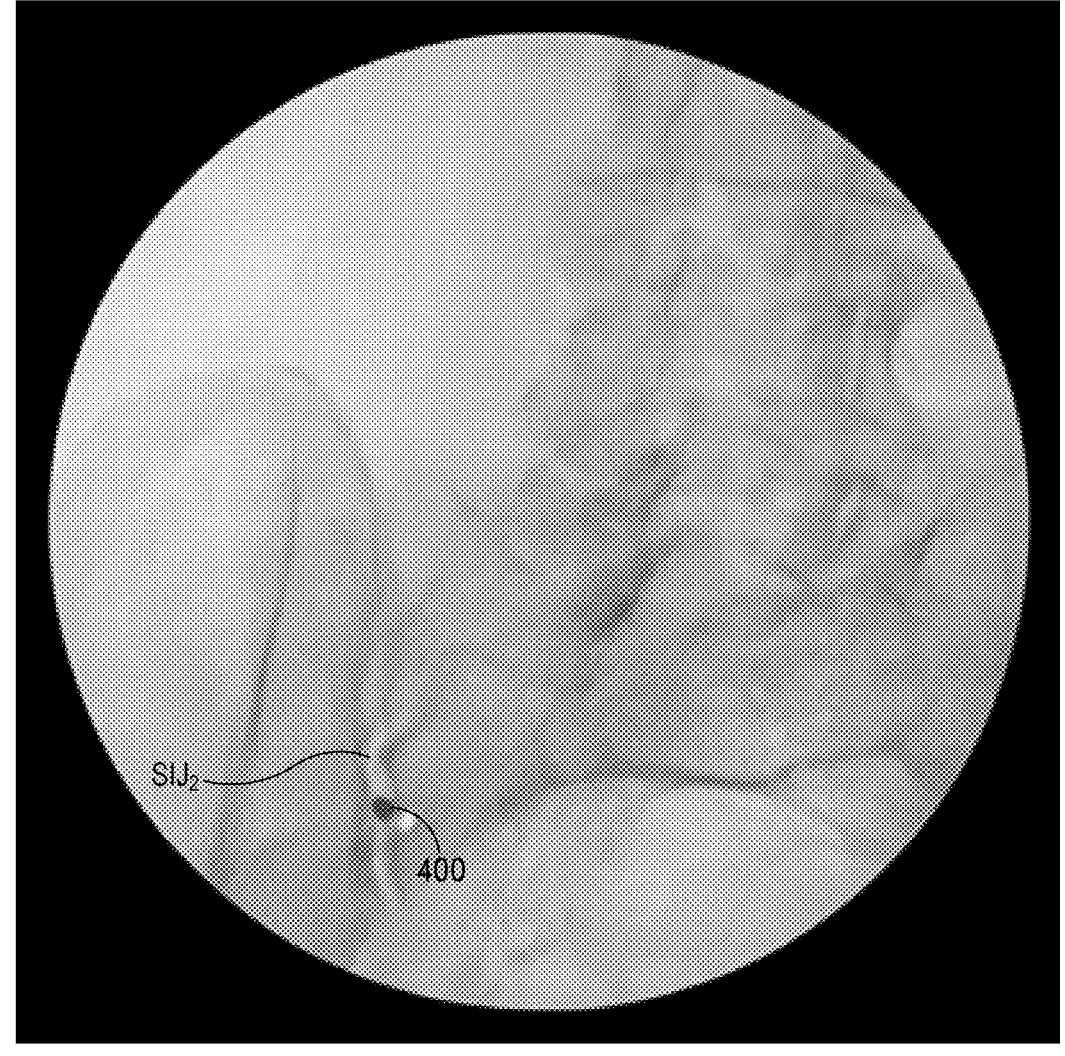
FIG. 13D is a CT scan image showing a trajectory inlet view of the dysfunctional SI joint shown in FIG. 13B, showing a guide pin properly positioned therein, in accordance with the invention.
Figure 13E:
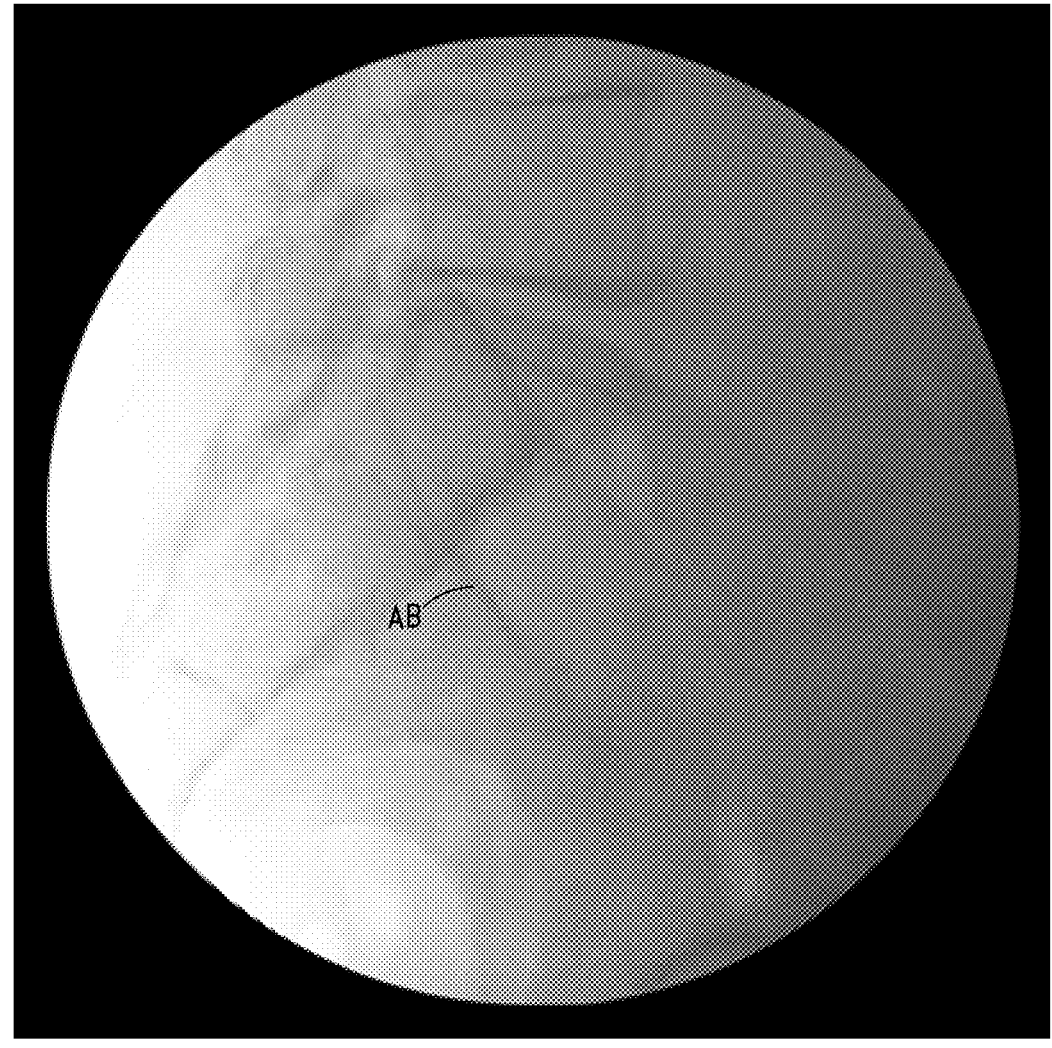
FIG. 13E is a CT scan image showing a lateral view of the dysfunctional SI joint shown in FIG. 13B, showing the alar boundary thereof, in accordance with the invention.
Figure 13F:
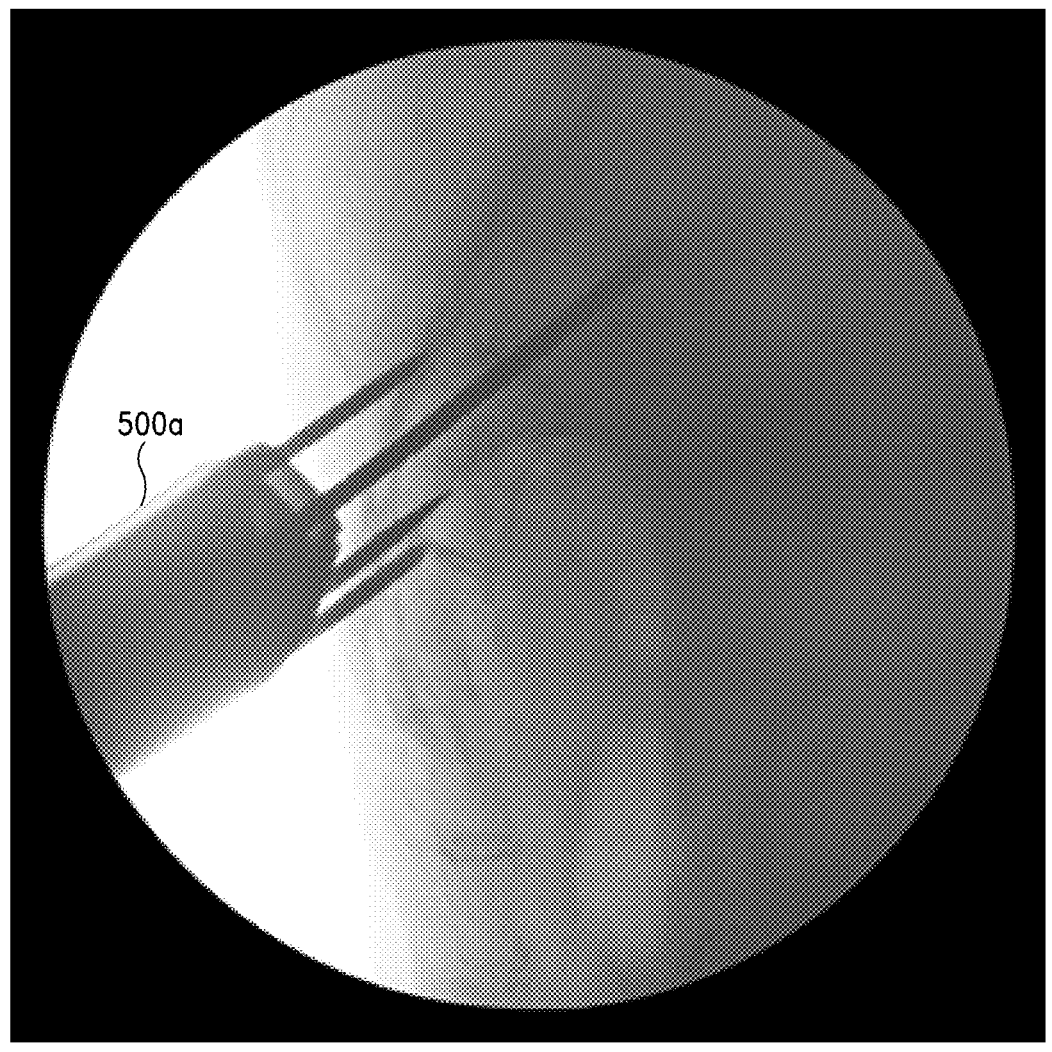
FIG. 13F is a CT scan image showing a lateral view of a drill guide assembly disposed proximate a dysfunctional SI joint, in accordance with the invention.
Figure 13G:
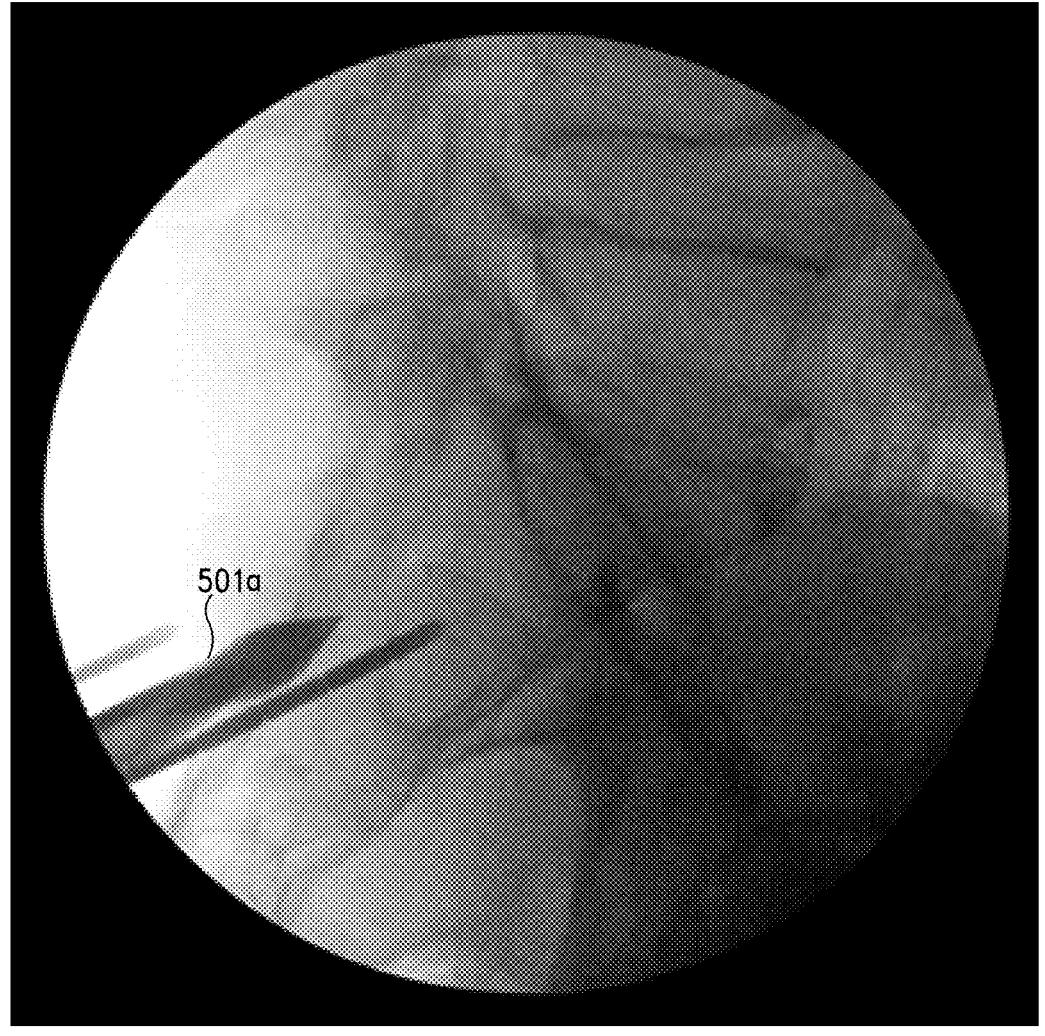
FIG. 13G is a CT scan image showing a further lateral view of the drill guide assembly disposed proximate a dysfunctional SI joint, in accordance with the invention.
Figure 13H:
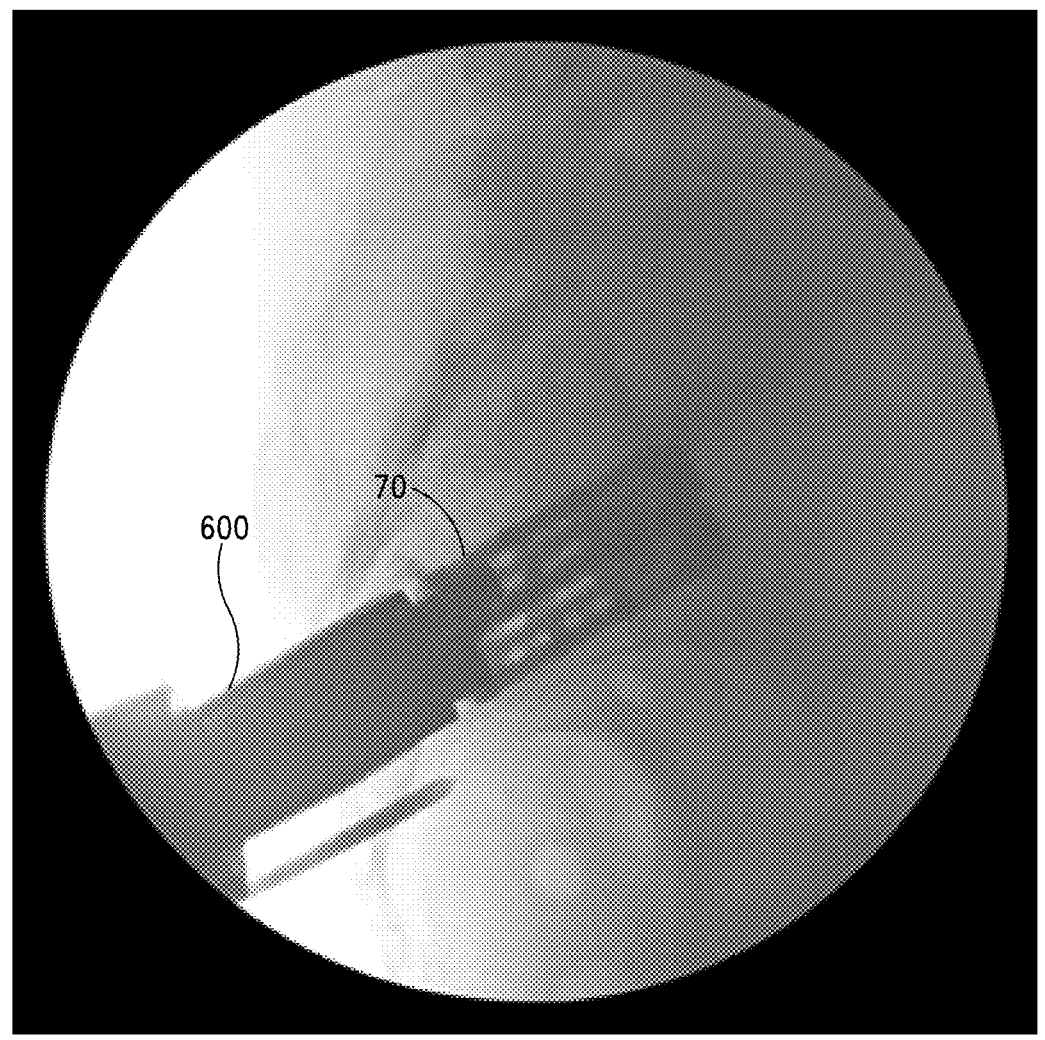
FIG. 13H is a CT scan image showing a lateral view of the prosthesis deployment assembly with a SI joint prosthesis engaged thereto disposed proximate a dysfunctional SI joint, in accordance with the invention.
Figure 131:
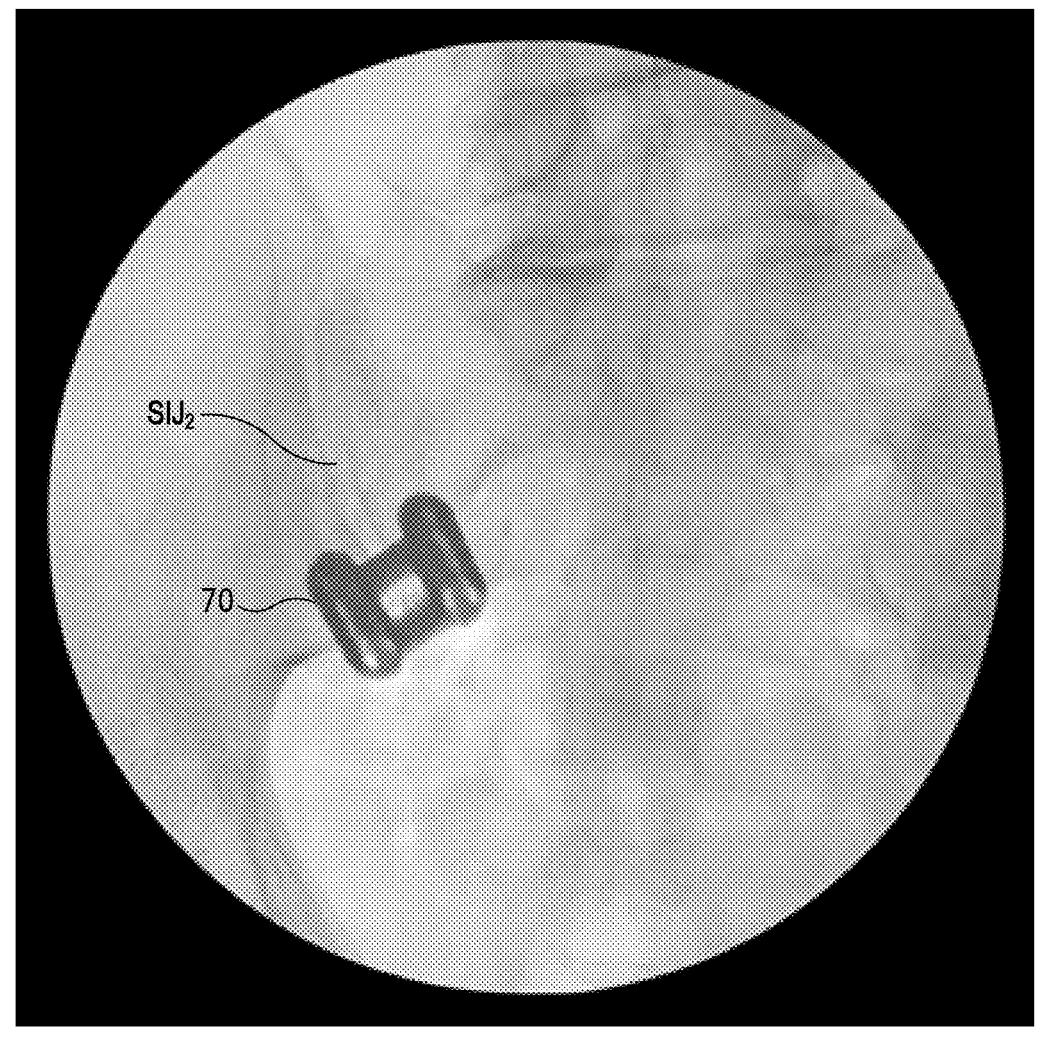
Figure 13J:
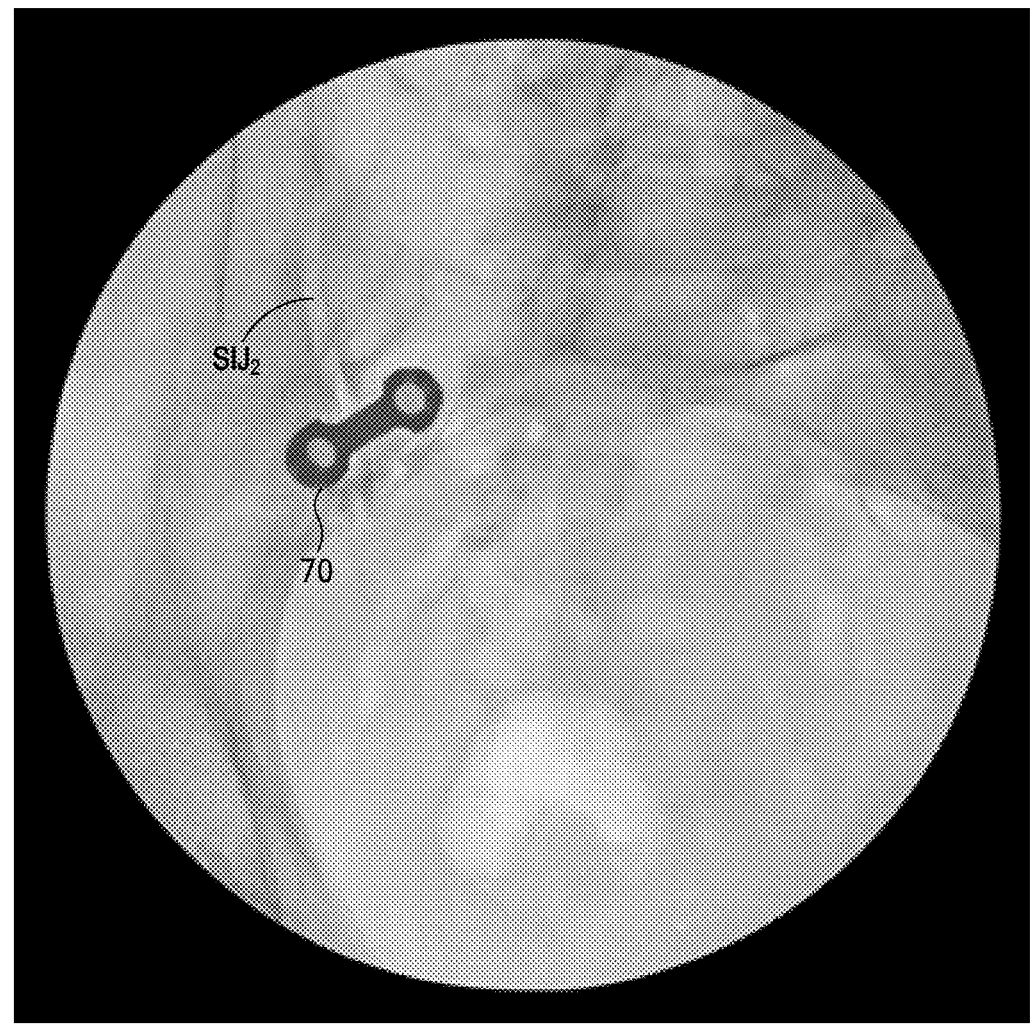
FIG. 13J is a CT scan image showing a trajectory inlet view of the dysfunctional SI joint shown in FIG. 13B, showing a SI joint prosthesis properly positioned therein, in accordance with the invention.
Figure 14A:
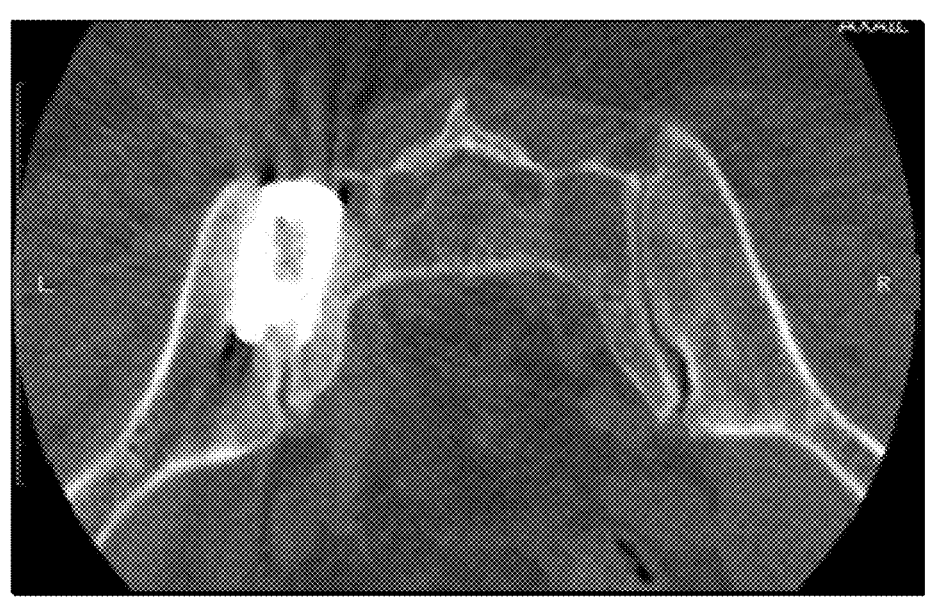
FIGS. 14A and 14B are further CT scan images of the SI joint prosthesis shown in FIG. 10A properly positioned in a dysfunctional SI joint, in accordance with the invention.
Figure 14B:
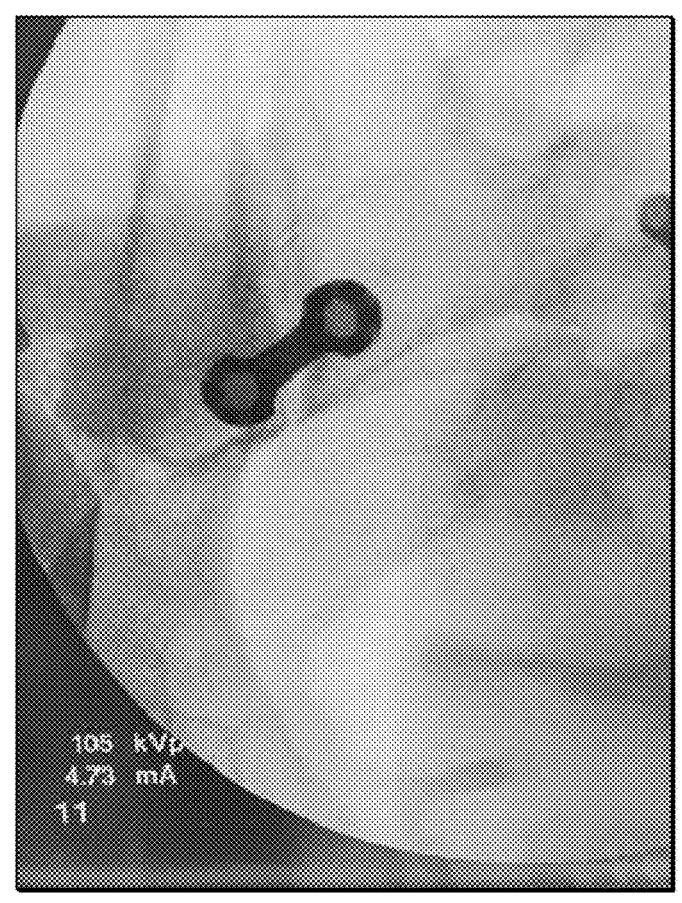

In accordance with the one embodiment of the invention, there is thus provided a method of stabilizing a dysfunctional SI joint comprising the following steps:

providing a tool assembly of the invention, in this instance, a tool assembly comprising drill guide assembly 500a;

providing a SI joint prosthesis of the invention, in this instance, SI joint prosthesis 70;

providing a prosthesis deployment assembly of the invention, in this instance prosthesis deployment assembly 600a;

making an incision in and through tissue of the subject to provide posterior access to the subject's dysfunctional SI joint;

advancing the guide pin 400 of the tool assembly 500a from a posterior approach in and through the incision;

advancing the guide pin 400 into the dysfunctional SI joint, wherein the guide pin 400 is positioned in the dysfunctional SI joint at an angle in the range of 25°-35° relative to the cephalocaudal axis of the subject;

assembling the drill guide assembly 500a, i.e., positioning the drill guide 520a in the access sleeve 502;

inserting the guide pin 400 into the drill guide medial lumen 526 of the drill guide assembly 500a;

advancing the drill guide assembly 500a from a posterior approach in and through the incision site and, thereby positioning the drill guide assembly 500a proximate the dysfunctional SI joint;

inserting K-wires 509 into and through lumens 507 of the access sleeve 502 of the drill guide assembly 500a and into dysfunctional SI joint structures, e.g., SI joint soft and hard tissue, to position and stabilize the drill guide assembly 500a proximate the dysfunctional SI joint;

advancing the drill bit 501a through a first drill guide internal lumen, i.e., drill guide internal lumen 524a of the drill guide 520a and to a first bone structure, i.e., ilium or sacrum, of the dysfunctional SI joint;

creating a first portion of a pilot SI joint opening in the first bone structure with the drill bit 501a;

retracting the drill bit 501a out of the first bone structure and drill guide internal lumen 524a of the drill guide 520a;

inserting the drill alignment pin 530a of the drill guide assembly 500a into the first portion of the pilot SI joint opening to further stabilize the drill guide assembly 500a proximate the dysfunctional SI joint;

advancing the drill bit 501a through the second drill guide internal lumen, i.e., drill guide internal lumen 524b, of the drill guide 520a to the second (or opposing) bone structure of the dysfunctional SI joint;

creating a second portion of the pilot SI joint opening in the second bone structure with the drill bit 501a;

retracting the drill bit 501a out of the second bone structure and drill guide 520a; retracting the drill alignment pin 530a out of the first portion of the pilot SI joint opening; removing the drill guide 520a from the access sleeve 502 of the drill guide assembly 500a, wherein the guide pin 400 is also retracted out of the drill guide medial lumen 526;

retracting the guide pin 400 out of the dysfunctional SI joint;

connecting the prosthesis deployment assembly 600a to the SI joint prosthesis (in this instance SI joint prosthesis 70), wherein, as indicated above, the prosthesis guide pin 606 of the prosthesis deployment assembly 600a is inserted into the first internal prosthesis engagement member lumen 86a of the first elongated partially cylindrical section 76a of the SI joint prosthesis, i.e., SI joint prosthesis 70, and the threaded distal end 704 of the prosthesis engagement rod 700 is threaded into the second internal prosthesis engagement member lumen 86b of the second elongated partially cylindrical section 76b of the SI joint prosthesis, i.e., SI joint prosthesis 70, or, alternatively, the prosthesis guide pin 606 of the prosthesis deployment assembly 600a is inserted into the second internal prosthesis engagement member lumen 86b of the first elongated partially cylindrical section 76b of the SI joint prosthesis, i.e., SI joint prosthesis 70, and the threaded distal end 704 of the prosthesis engagement rod 700 is threaded into the first internal prosthesis engagement member lumen 86a of the first elongated partially cylindrical section 76a of the SI joint prosthesis, i.e., SI joint prosthesis 70;

inserting the SI joint prosthesis, i.e., SI joint prosthesis 70, into and through the internal opening 506 of the access sleeve 502 and into the pilot SI joint opening with the prosthesis deployment assembly 600a, wherein the SI joint prosthesis, i.e., SI joint prosthesis 70, is spaced a predetermined distance away from the SI joint dorsal recess (such as shown in FIG. 13H);

retracting the prosthesis deployment assembly 600a out of the dysfunctional SI joint; retracting the K-wires 509 out of the dysfunctional SI joint structures; and retracting the access sleeve 502 out of the subject's body.

In accordance with another embodiment of the invention, the method for stabilizing a dysfunctional SI joint similarly comprises the steps of (i) providing a tool assembly of the invention, in this instance, a tool assembly comprising drill guide assembly 500b, (ii) providing a SI joint prosthesis configured and adapted to be inserted into the pilot SI joint opening created by the tool assembly, in this instance, SI joint prosthesis 70, (iii) providing a prosthesis deployment assembly of the invention, in this instance, prosthesis deployment assembly 600a, and (iv) making an incision in and through tissue at a predetermined incision site of the subject.

However, as discussed in detail below, by virtue of the unique configuration of drill guide 520b of the drill guide assembly 500b, the length of the incision required is only in the range of approximately 2.0 cm to 3.0 cm, i.e., approximately ½ the incision length required with drill guide assembly 500a.

After the 2.0 cm to 3.0 cm incision is made in and through tissue at a predetermined incision site of the subject, the next steps in the noted method preferably comprise the following:

advancing the guide pin 400 from a posterior approach into and through the incision and into the dysfunctional SI joint, as indicated above;

inserting the guide pin 400 into the drill guide medial lumen 527 of the drill guide 520b;

attaching the drill guide handle, i.e., handle 510a shown in FIG. 3E or handle 510b shown in FIG. 5D, to the drill guide 520b, the handle being attached to drill guide lumen 511b of the drill guide 520b (denoted by letter "R") when positioned on the right side of the patient, or attached to drill guide lumen 511a of the drill guide 520b (denoted by letter "L") when positioned on the left side of the patient, wherein, when the drill guide 520b is positioned proximate the incision site, the drill guide handle 510a (or handle 510b) is substantially perpendicular to the patient's spine;

positioning the drill guide 520b proximate the incision site, where, as discussed above, the drill guide handle 510*a* (or handle 510*b*) is substantially perpendicular to the patient's spine;

inserting K-wires 509 into and through at least K-wire lumens 529*b* and 529*c*, more preferably K-wires 529*a*, 529*b*, 529*c*, 529*d*, of the drill guide 520*b* and into dysfunctional SI joint structures, e.g., SI joint soft and hard tissue, to position and stabilize the drill guide 520*b* and, hence, drill guide assembly 500*b* proximate the incision;

inserting the K-wire pin member 550 into and through a first drill guide internal lumen, i.e., drill guide internal lumen 525*a*, of the drill guide 520*b* and to a first bone structure, e.g., ilium, of the dysfunctional SI joint to further support and stabilize the drill guide assembly 520*b*;

advancing the bone dislodging member, i.e., drill bit 501*b*, through the second drill guide internal lumen, i.e., drill guide internal lumen 525*b*, of the drill guide 520*b* and to the second bone structure, i.e., sacrum, of the dysfunctional SI joint;

creating a first portion of a pilot SI joint opening in the second bone structure of the dysfunctional SI joint with the drill bit 501*b* of the drill guide assembly 500*b*; retracting the drill bit 501*b* out of the second bone structure and second drill guide internal lumen 525*b* of the drill guide 520*b*;

inserting the temporary fixation pin 530*b* into the first portion of the pilot SI joint opening to further stabilize the drill guide assembly 500*b*;

retracting the K-wire pin member 550 out of the first drill guide internal lumen, i.e., drill guide internal lumen 525*a*, and first bone structure;

advancing the drill bit 501*b* through the first drill guide internal lumen, i.e., drill guide internal lumen 525*b*, to the first bone structure of the dysfunctional SI joint; creating a second portion of the pilot SI joint opening in the first bone structure with the drill bit 501*b*;

retracting the drill bit 501*b* out of the first bone structure and first drill guide internal lumen 525*a* of the drill guide assembly 500*b*;

retracting the temporary fixation pin 530*b* out of the first portion of the pilot SI joint opening;

retracting the K-wires 509 out of the dysfunctional SI joint and drill guide assembly 500*b*;

removing the drill guide assembly 500*b* from the incision site, wherein the guide pin 400 is also retracted out of the drill guide medial lumen 527 of the drill guide assembly 500*b*; retracting the guide pin 400 out of the dysfunctional SI joint;

connecting the prosthesis deployment assembly 600*a* to the SI joint prosthesis (in this instance SI joint prosthesis 70), as described above;

advancing the SI joint prosthesis, i.e., SI joint prosthesis 70, into the pilot SI joint opening with the prosthesis deployment assembly 600*a*, wherein the SI joint prosthesis, i.e., SI joint prosthesis 70, is similarly spaced a predetermined distance away from the SI joint dorsal recess; and retracting the prosthesis deployment assembly 600*a* out of the dysfunctional SI joint.

According to the invention, prosthesis deployment assembly 600*b* can be substituted for prosthesis deployment assembly 600*a* to advance the SI joint prosthesis into the pilot SI joint opening in the noted method for stabilizing a dysfunctional SI joint.

In accordance with another embodiment of the invention, the method for stabilizing a dysfunctional SI joint similarly comprises the steps of (i) providing a tool assembly of the invention, in this instance, a tool assembly comprising drill guide assembly 500*c*, (ii) providing a SI joint prosthesis configured and adapted to be inserted into the pilot SI joint opening created by the tool assembly, in this instance, SI joint prosthesis 70, and (iii) providing a prosthesis deployment assembly of the invention, in this instance, prosthesis deployment assembly 600*b*.

After the tool assembly, SI joint prosthesis and prosthesis deployment assembly are provided, the next steps in the noted method preferably comprise the following:

assembling the drill guide assembly 500*c*, i.e., inserting the elongated guide member 800*a* into the medial portion 562 of the prosthesis internal access opening 560 in the drill guide, in this instance, drill guide 520*c*;

making the 2.0 cm to 3.0 cm incision in and through tissue of the subject at a predetermined incision site;

advancing the guide pin 400 from a posterior approach into and through the incision and into the dysfunctional SI joint, as indicated above;

inserting the guide pin 400 into the guide member lumen 827 of the elongated guide member 800*a*;

attaching a drill guide handle, i.e., handle 510*a* shown in FIG. 3E or handle 510*b* shown in FIG. 5D, to the drill guide 520*c*, as described above;

positioning the drill guide 520*c* proximate the incision site, where, as discussed above, the drill guide handle 510*a* (or handle 510*b*) is substantially perpendicular to the patient's spine;

inserting K-wires 509 into and through at least K-wire lumens 529*b* and 529*c*, more preferably K-wires 529*a*, 529*b*, 529*c*, 529*d*, of the drill guide 520*c* and into dysfunctional SI joint structures, e.g., SI joint soft and hard tissue, to position and stabilize the drill guide 520*c* and, hence, drill guide assembly 500*c* proximate the incision;

inserting the K-wire pin member 550 into and through a first lobe portion 564*a* of the prosthesis internal access opening 560 to a first bone structure, e.g., ilium, of the dysfunctional SI joint to further support and stabilize the drill guide assembly 520*c*;

advancing the bone dislodging member, i.e., drill bit 501*b* or 501*c*, through the second lobe portion 564*b* of the prosthesis internal access opening 560 to the second bone structure, i.e., sacrum, of the dysfunctional SI joint;

creating a first portion of a pilot SI joint opening in the second bone structure of the dysfunctional SI joint with the drill bit 501*b* or 501*c*;

retracting the drill bit 501*b* or 501*c* out of the second bone structure and second lobe portion 564*b* of the prosthesis internal access opening 560;

inserting the temporary fixation pin 530*b* into the first portion of the pilot SI joint opening to further stabilize the drill guide assembly 500*c*;

retracting the K-wire pin member 550 out of the first bone structure and first lobe portion 564*a* of the prosthesis internal access opening 560;

advancing the drill bit 501*b* or 501*c* through the first lobe portion 564*a* of the prosthesis internal access opening 560 to the first bone structure of the dysfunctional SI joint; creating a second portion of the pilot SI joint opening in the first bone structure with the drill bit 501*b* or 501*c*;

retracting the drill bit 501*b* or 501*c* out of the first bone structure and first lobe portion 564*a* of the prosthesis internal access opening 560;

retracting the temporary fixation pin 530*b* out of the first portion of the pilot SI joint opening;

removing the elongated guide member 800*a* from the prosthesis internal access opening 560 of the drill guide 520*c*, wherein the guide pin 400 is also retracted out of the drill guide 520*c*;

retracting the guide pin 400 out of the dysfunctional SI joint;

connecting the prosthesis deployment assembly 600*b* to the SI joint prosthesis (in this instance SI joint prosthesis 70), as described above;

advancing the SI joint prosthesis, i.e., SI joint prosthesis 70, into and through the prosthesis internal access opening 560 and into the pilot SI joint opening with the prosthesis deployment assembly 600*b*, wherein the SI joint prosthesis, i.e., SI joint prosthesis 70, is similarly spaced a predetermined distance away from the SI joint dorsal recess;

retracting the prosthesis deployment assembly 600*b* out of the dysfunctional SI joint and the prosthesis internal access opening 560 in the drill guide 520*c*;

retracting the K-wires 509 out of the dysfunctional SI joint and drill guide 520*c*; and removing the drill guide 520*c* from the subject's body.

In some embodiments of the invention, prior to the step of advancing the bone dislodging member through the second lobe portion 564*b* of the prosthesis internal access opening 560 to the second bone structure, i.e., sacrum, of the dysfunctional SI joint to create the first portion of the pilot SI joint opening, the method further comprises the step of initially advancing the K-wire pin member 550 or temporary fixation pin 530*b* through the second lobe portion 564*b* of the prosthesis internal access opening 560 to the second bone structure to provide a guide recess in the second bone structure for the bone dislodging member.

As indicated above, in a preferred embodiment, when the SI joint prosthesis, i.e., SI joint prosthesis 70, is advanced into the pilot SI joint opening with the prosthesis deployment assemblies 600*a*, 600*b*, the SI joint prosthesis, i.e., SI joint prosthesis 70, is disposed at a distance in the range of at least 2.0 mm to 6.0 mm away from the SI joint dorsal recess, more preferably, a distance of at least 3.0 mm away from the SI joint dorsal recess.

In a preferred embodiment, when the SI joint prosthesis, i.e., SI joint prosthesis 70, is advanced into the pilot SI joint opening with the prosthesis deployment assemblies 600*a*, 600*b*, the SI joint prosthesis, i.e., SI joint prosthesis 70, is press-fit in the pilot SI joint opening and induces a transition of the pilot SI joint opening to a larger post-prosthesis insertion SI joint opening.

In some embodiments of the invention, when the SI joint prosthesis, i.e., SI joint prosthesis 70, is press-fit into the pilot SI joint opening, the cross-sectional shape of the first portion of the pilot SI joint opening transitions to a second cross-sectional shape comprising a larger cross-sectional area, and the cross-sectional shape of the second portion of the pilot SI joint opening similarly transitions to a second cross-sectional shape comprising a larger cross-sectional area.

In a preferred embodiment, a further initial step in the minimally-invasive SI joint stabilization methods of the invention comprises the step of providing an image capture apparatus configured and adapted to capture images of at least the subject's anatomical structure, including the dysfunctional SI joint and the anatomic structure proximate thereto, and the guide pin 400 and SI joint prosthesis 70 during advancement toward and when disposed proximate to the dysfunctional SI joint.

In a preferred embodiment, the image capture apparatus comprises a CT system. However, according to the invention, further suitable image capture apparatus comprise a fluoroscope, radiography system, magnetic resonance imaging system, and an ultrasound system.

In a preferred embodiment, after the step of providing the image capture apparatus, and before the step of making an incision in and through tissue of the subject, a further step in the minimally-invasive SI joint stabilization methods comprises capturing images of the subject's anatomical structure with the image capture apparatus to properly align the patient on the surgical table. According to the invention, standard or classic lateral images via CT scans can be employed to ensure proper alignment, i.e., a true prone position, of the patient.

After the step of ensuring proper alignment of the patient, a further initial step in the minimally-invasive SI joint stabilization methods of the invention comprises determining key SI joint landmarks, e.g., dogleg, dorsal recess, etc., preferably, via CT scans, to establish at least a sagittal line, incision (or skin entry) site, and guide pin trajectory and, thereby, prosthesis trajectory into the dysfunctional SI joint.

Since the SI joint comprises a unique shape and does not align with the axis of the spine (i.e., the plane of the SI joint defined by the region between the sacrum and the ilium is not aligned with (or parallel with) the sagittal plane or anteroposterior axis of the spine), as discussed in detail below, in a preferred embodiment, modified anteroposterior (AP) views or images of at least the subject's dysfunctional SI joint, and the guide pin 400 and SI joint prosthesis when deployed in the subject's body are acquired via CT scans.

As discussed above, advancement of the guide pin into the dysfunctional SI joint is a critical step in the methods for stabilizing a dysfunctional SI joint. The guide pin 400 ensures (i) proper trajectory of the drill guides of the invention and creation of the pilot SI joint openings, e.g., pilot SI joint opening 100, (ii) proper trajectory of the prosthesis deployment assemblies 600*a*, 600*b* and, hence, SI joint prosthesis engaged thereto to and into the pilot SI joint openings and, thereby, accurate and optimal placement of the SI joint prosthesis in the dysfunctional SI joint.

In a preferred embodiment, during the step of advancing the guide pin 400 into the dysfunctional SI joint, a further step in the minimally-invasive SI joint stabilization methods thus comprises capturing images of the guide pin 400 with the image capture apparatus to ensure proper trajectory and placement of the guide pin 400 proximate the dysfunctional SI joint.

As indicated above, since the SI joint comprises a unique shape and does not align with the axis of the spine, in a preferred embodiment, a series modified (or angled) anteroposterior (AP) images of the guide pin 400 and dysfunctional SI joint (and, if necessary, surrounding structures) during advancement of the guide pin 400 toward and, particularly, when disposed proximate to and in the dysfunctional SI joint are preferably acquired via CT scans to ensure proper trajectory and placement of the guide pin 400 proximate the dysfunctional SI joint.

Referring first to FIG. 13A there is shown a conventional AP view image of a dysfunctional SI joint. As illustrated in FIG. 13A the SI joints (denoted "SIJ$_1$" and "SIJ$_2$"), including the dysfunctional SI joint on the left side ("SIJ$_2$"), are represented by multiple non-linear lines, which reflect misalignment of the imaged SI joints ("SIJ$_1$" and "SIJ$_2$"). The mis-alignment of the imaged SI joints ("SIJ₁" and "SIJ₂") in the conventional AP view image makes properly aligning the guide pin 400 in a SI joint, i.e., "SIJ₁" or "SIJ₂", very difficult. Indeed, one must guess the advancement trajectory of the guide pin 400.

Referring now to FIG. 13B, there is shown a CT scan image showing a modified AP view of the left, i.e., dysfunctional, SI joint ("SIJ₂"). As illustrated in FIG. 13B, the dysfunctional SI joint ("SIJ₂") is now shown and, hence, represented by a substantially straight line indicating substantial alignment of the imaged dysfunctional SI joint ("SIJ₂").

The modified AP view of the dysfunctional SI joint ("SIJ₂") shown in FIG. 13B facilitates accurate advancement, trajectory, and positioning of the guide pin 400 in the dysfunctional SI joint ("SIJ₂"), as shown in the tangent lateral and trajectory inlet views shown in FIGS. 13C and 13D, respectively.

As indicated above, in a preferred embodiment, the guide pin 400 is advanced into the dysfunctional SI joint to, but no further than, the alar boundary (denoted "AB" in FIGS. 1A, 13C and 13E).

A CT scan image showing a tangent lateral view of the dysfunctional SI joint ("SIJ₂") also facilitates accurate advancement and, hence, depth of the guide pin 400 in the dysfunctional SI joint ("SIJ₂"), as shown in FIG. 13C.

In a preferred embodiment, during the step of advancing the SI joint prosthesis into the pilot SI joint opening with the prosthesis deployment assemblies 600a, 600b, a further step in the minimally-invasive SI joint stabilization methods comprises capturing images of the SI joint prosthesis with the image capture apparatus to ensure proper placement of the SI joint prosthesis in the dysfunctional SI joint.

In a preferred embodiment, CT scan images showing lateral views of the drill guide assemblies 500a, 500b, 500c and the prosthesis deployment assemblies 600a, 600b during advancement of the drill guide assemblies 500a, 500b, 500c and prosthesis deployment assemblies 600a, 600b toward and, particularly, when disposed proximate to the dysfunctional SI joint are acquired to ensure proper trajectory of the drill guide assemblies 500a, 500b, 500c and the prosthesis deployment assemblies 600a, 600b, such as shown in FIGS. 13F, 13G, and 13H.

In a preferred embodiment, CT scan images showing modified AP and/or trajectory inlet views of the SI joint prosthesis and dysfunctional SI joint (and, if necessary, surrounding structures) during advancement of the SI joint prosthesis toward and, particularly, when disposed proximate to and in the dysfunctional SI joint are also acquired to ensure proper trajectory and placement of the SI joint prosthesis in the dysfunctional SI joint, such as shown in FIGS. 13I, 13J, 14A, and 14B.

In some embodiments, after the step of creating the pilot SI joint opening with the drill guide assemblies 500a, 500b, 500c the methods for stabilizing a dysfunctional SI joint further comprise the step of collecting the dislodged bone material, e.g., cortical bone, trabecular bone, and bone marrow, for subsequent use in a biologically active composition of the invention.

In some embodiments of the invention, after the step of retracting the prosthesis deployment assemblies 600a, 600b out of the dysfunctional SI joint, the minimally-invasive SI joint stabilization methods further comprise the step of placing an osteogenic composition or at least one of the aforementioned biologically active agents and/or one of the aforementioned pharmacological agents in one or both of the internal prosthesis engagement member lumens of the SI joint prosthesis, i.e., internal prosthesis engagement member lumens 86a, 86b of SI joint prosthesis 70, whereby the osteogenic composition or biologically active agent or pharmacological agent is dispersed through the slots 90 and holes 92 of the SI joint prosthesis 70 and administered to the osseous tissue of the SI joint bone structures, i.e., sacrum and ilium bone structures, when the SI joint prosthesis 70 is positioned therein.

In some embodiments, the osteogenic composition comprises a demineralized bone matrix, autograft bone material, allograft bone material, xenograft bone material, polymethyl-methacrylate, or calcium-based bone material.

In some embodiments, the osteogenic composition comprises a bone morphogenic protein (BMP).

In some embodiments, the BMP comprises BMP-1, BMP2a, BMP2b, BMP3, BMP4, BMP5, BMP6, BMP7, or BMP8a.

In some embodiments, the biologically active agent comprises a basic fibroblast growth factor (bFGF), a transforming growth factor-β (TGF-β), a vascular endothelial growth factor (VEGF), a platelet derived growth factor (PDGF), an insulin-like growth factor (IGF), an epidermal growth factor (EGF), or a growth and differentiation factor-5 (GDF-5).

In some embodiments, the pharmacological agent comprises one of the aforementioned antibiotics.

In some embodiments, the antibiotic comprises penicillin, a carboxypenicillin, a tetracycline, gentamicin, vancomycin, ciprofloxacin, amikacin, an aminoglycoside, a cephalosporin, clindamycin, erythromycin, a fluoroquinolone, a macrolide, an azolide, metronidazole, trimethoprim-sulfamethoxazole, polymyxin B, oxytetracycline, tobramycin, cefazolin, or rifampin.

In some embodiments, the pharmacological agent comprises one of the aforementioned anti-inflammatories.

In some embodiments the anti-inflammatory comprises dexamethasone, betamethasone, prednisone, prednisolone, methylprednisolone sodium succinate, methylprednisolone, cortisone, ketorolac, diclofenac, or ibuprofen.

There is accordingly also provided systems for stabilizing a dysfunctional SI joint comprising an aforementioned tool assembly of the invention, a prosthesis of the invention and a prosthesis deployment assembly of the invention.

In one embodiment, the tool assembly comprises drill guide assembly 500a.

In another embodiment, the tool assembly comprises drill guide assembly 500b.

In yet another embodiment, the tool assembly comprises drill guide assembly 500c.

EXAMPLES

The following example is provided to enable those skilled in the art to more clearly understand and practice the present invention. The example should not be considered as limiting the scope of the invention, but merely as being illustrated as representative thereof.

An adult male, age 42 presented with a traumatic injury proximate the SI joint, resulting in a dysfunctional SI joint and significant pain associated therewith, i.e., a visual analog pain score (VAS) of approximately 8.0.

CT scans were initially performed to determine the full extent of the patient's injury, check for any SI joint abnormalities, and plan the SI joint stabilization procedure, including determining the incision site, guide pin trajectory, and SI joint prosthesis required to stabilize the dysfunctional SI joint.

Before proceeding with the SI joint stabilization procedure, CT scans were also performed to ensure proper alignment of the patient on the surgical table.

The SI joint stabilization procedure was performed in accord with the method that includes the drill guide assembly 500c summarized above. The specifics of the procedure were as follows:

SI Joint Prosthesis

The SI joint prosthesis selected and, hence, provided for the stabilization procedure comprised SI joint prosthesis 70 illustrated in FIGS. 10A and 10B and described in detail above. The SI joint prosthesis comprised a length of 30 mm and the elongated partially cylindrical sections, i.e., barrels, of the SI joint prosthesis comprised a diameter of 7.5 mm. The SI joint prosthesis was sourced from Applicant, i.e., Tenon Medical, Inc., and referred to as a CATAMARAN SIJ Fixation System™.

The SI joint prosthesis included an autograft bone material, which was placed in the barrels of the SI joint prosthesis after the prosthesis was implanted in the dysfunctional SI joint.

Posterior Inferior Surgical Approach

The initial incision was placed along the lateral lip of the posterior third of the iliac crest to the posterior superior spine, which provided a prosthesis entry point into the dysfunctional SI joint through the posterior ligaments at approximately the S3 level. The trajectory of the SI joint prosthesis was toward the mid-point of the S1 end plate and the sacral promontory.

Creation of Pilot SI Joint Opening

The pilot SI joint opening was created with the drill guide assembly 500c shown in FIGS. 5A-5C, and described above.

Figure 7C:
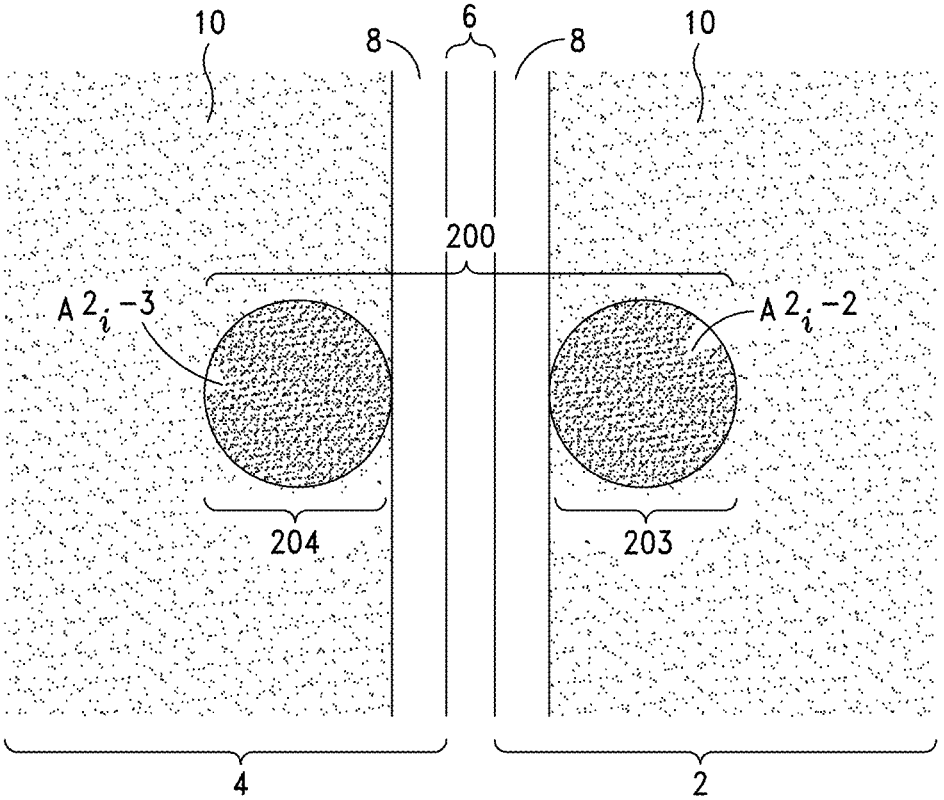

The pilot SI joint opening, which was similar to pilot SI joint opening 200 described above, was created by drilling a first opening in the sacrum bone structure and a second opening in the ilium bone structure (such as shown in FIG. 7C) with the drill guide assembly 500c.

Radiological Assessment

CT scan images of the patient's SI joint six (6) months after the SI joint stabilization procedure reflected (i) secure and proper placement of the SI joint prosthesis in the SI joint, (ii) substantial solid bridging of osseous tissue, and, hence, bone across the SI joint and, (iii) substantial ossification around the SI joint prosthesis.

Post-Procedure SI Joint Pain Relief and Function

After a recovery period of fourteen (14) days, the patient reported that the pain had been substantially reduced.

The patient was also subjected to a series of post procedure tests to determine the stability of the SI joint and mobility of the musculoskeletal structures of the pelvic and lumbar regions proximate the SI joint. The results were very favorable. The patient tested positive to the flexion abduction and external rotation (FABER) test. The patient also responded very favorably to Gaenslen, thigh thrust, compression, and distraction tests.

The tests thus confirmed that the post procedure SI joint was stabilized and that the musculoskeletal structures of the pelvic and lumbar regions proximate thereto were restored to a near normal level.

As will readily be appreciated by one having ordinary skill in the art, the present invention provides numerous advantages compared to prior art systems and methods for stabilizing dysfunctional SI joints. Among the advantages are the following:

the provision of improved minimally-invasive SI joint stabilization systems and apparatus, and methods of using same, which facilitate posterior trajectory placement of SI joint prostheses in dysfunctional SI joints and, thereby, stabilization of the dysfunctional SI joints;

the provision of improved minimally-invasive SI joint stabilization systems, which, when employed to stabilize dysfunctional SI joints, disrupt less tissue and muscles, and avoid nerves and large blood vessels;

the provision of improved minimally-invasive SI joint stabilization systems and apparatus, including prostheses, which, when employed to stabilize dysfunctional SI joints, effectively ameliorate pain associated with SI joint dysfunction;

the provision of improved minimally-invasive SI joint stabilization systems comprising drill guide assemblies adapted to create pilot openings in dysfunctional SI joints for placement of SI joint prostheses therein via a minimal incision, i.e., an incision length no greater than 3.0 cm;

the provision of improved minimally-invasive SI joint stabilization systems comprising drill guide assemblies adapted to create pilot openings in dysfunctional SI joints for placement of SI joint prostheses therein, which provide optimal direct visualization of the bone dislodging member thereof and the pilot opening during and after creation of the pilot openings;

the provision of improved minimally-invasive SI joint stabilization systems comprising drill guide assemblies adapted to receive and guide and, thereby, provide consistent, optimal placement of SI joint prostheses into dysfunctional SI joints;

the provision of improved minimally-invasive SI joint stabilization systems comprising drill guide assemblies adapted to create pilot openings in dysfunctional SI joints for placement of SI joint prostheses therein, which provide consistent, optimal arthrodesis of the dysfunctional SI joint after placement of a SI joint prosthesis in the pilot openings; and the provision of improved SI joint prostheses that can readily be employed in minimally-invasive SI joint stabilization systems, which facilitate remodeling of damaged osseous tissue and regeneration of new osseous tissue and osseous tissue structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for stabilizing a dysfunctional sacroiliac (SI) joint of a subject, said dysfunctional SI joint comprising first and second bone structures, said system comprising:

a tool assembly, a SI joint prosthesis, and a prosthesis deployment assembly, said tool assembly comprising a guide pin and a drill guide assembly, said guide pin adapted to be positioned in said dysfunctional SI joint, said drill guide assembly adapted to create a pilot SI joint opening in said dysfunctional SI joint through an incision comprising a length no greater than 3.0 cm, said pilot SI joint opening comprising first and second portions, said drill guide assembly comprising a drill guide, a bone dislodging member, a first drill guide fixation sub-system, a second drill guide fixation sub-system and a third drill guide fixation sub-system, said bone dislodging member adapted to dislodge portions of bone in said first and second bone structures of said dysfunctional SI joint, said drill guide comprising a base and a guide member comprising a guide pin lumen adapted to receive said guide pin therein, said first drill guide fixation sub-system comprising a plurality of anchor members extending from said base of said drill guide, said plurality of anchor members adapted to pierce and engage biological tissue, said second drill guide fixation sub-system comprising a plurality of Kirschner-wires (K-wires) adapted to pierce and engage said first and second bone structures of said dysfunctional SI joint, said third drill guide fixation sub-system comprising a K-wire pin member and a temporary fixation pin, said K-wire pin member and said temporary fixation pin also adapted to pierce and engage said first and second bone structures of said dysfunctional SI joint, said drill guide further comprising a prosthesis internal access opening and a plurality of fixation guide openings, said prosthesis internal access opening comprising a cross-sectional shape that corresponds to a cross-sectional shape of said SI joint prosthesis, whereby said SI joint prosthesis is readily received and positioned in said drill guide, said prosthesis internal access opening comprising first and second lobe portions, said plurality of fixation guide openings adapted to receive said plurality of K-wires therein, said first and second lobe portions of said prosthesis internal access opening adapted to receive said K-wire pin member, said temporary fixation pin, and said bone dislodging member therein, said first drill guide fixation sub-system operable when said plurality of anchor members pierces and engages first biological tissue proximate said dysfunctional SI joint, said second drill guide fixation sub-system operable when said plurality of K-wires is received in said plurality of fixation guide openings and engages said first and second bone structures of said dysfunctional SI joint, said third drill guide fixation sub-system operable when said K-wire pin member is received in said first lobe portion of said prosthesis internal access opening in said drill guide and engages said first bone structure of said dysfunctional SI joint, and when said K-wire pin member is received in said second lobe portion of said prosthesis internal access opening in said drill guide and engages said second bone structure of said dysfunctional SI joint, said third drill guide fixation sub-system further operable when said temporary fixation pin is received in said first lobe portion of said prosthesis internal access opening in said drill guide and engages said first bone structure of said dysfunctional SI joint, and when said temporary fixation pin is received in said second lobe portion of said prosthesis internal access opening in said drill guide and engages said second bone structure of said dysfunctional SI joint, said SI joint prosthesis configured and adapted to be inserted into and through said prosthesis internal access opening in said drill guide and into said pilot SI joint opening in said dysfunctional SI joint, said prosthesis deployment assembly configured and adapted to engage said SI joint prosthesis and guide said SI joint prosthesis into and through said prosthesis internal access opening in said drill guide and into said pilot SI joint opening in said dysfunctional SI joint.

2. The system of claim 1, wherein said tool assembly is adapted to access said dysfunctional SI joint in a posterior trajectory.

3. The system of claim 1, wherein said first bone structure of said dysfunctional SI joint comprises a sacrum bone structure and said second bone structure of said dysfunctional SI joint comprises an ilium bone structure.

4. The system of claim 1, wherein said bone dislodging member comprises a drill bit.

5. The system of claim 4, wherein said drill bit comprises a plurality of graduated markings reflecting a first depth of said drill bit into said first bone structure when said second portion of said pilot SI joint opening is said created in said first bone structure and a second depth of said drill bit into said second bone structure when said first portion of said pilot SI joint opening is said created in said second bone structure.

6. The system of claim 5, wherein said graduated markings are directly visible when said second portion of said pilot SI joint opening is said created in said first bone structure with said drill bit and when said first portion of said pilot SI joint opening is said created in said second bone structure with said drill bit.

7. The system of claim 1, wherein said SI joint prosthesis comprises first and second elongated partially cylindrical sections connected to a bridge section, said bridge section comprising a bridge section proximal end and a bridge section distal end disposed opposite said bridge section proximal end, said bridge section distal end comprising a first tapered region configured and adapted to disrupt at least articular cartilage and cortical bone, said first elongated partially cylindrical section of said SI joint prosthesis comprising a first internal prosthesis lumen extending from a prosthesis proximal end, said second elongated partially cylindrical section of said SI joint prosthesis comprising a second internal prosthesis lumen extending from said prosthesis proximal end, said first and second internal prosthesis lumens adapted to said engage said prosthesis deployment assembly.

8. The system of claim 7, wherein said first and second internal prosthesis lumens of said SI joint prosthesis are adapted to receive an osteogenic composition therein.

9. The system of claim 8, wherein said osteogenic composition comprises a bone-based material selected from the group consisting of a demineralized bone matrix, an autograft bone material, an allograft bone material, and a xenograft bone material.

10. The system of claim 8, wherein said osteogenic composition comprises a bone morphogenic protein (BMP) selected from the group consisting of BMP-1, BMP2a, BMP2b, BMP3, BMP4, BMP5, BMP6, BMP7, and BMP8a.

11. The system of claim 7, wherein at least said first internal prosthesis lumen further comprises a plurality of slots in communication with said first internal prosthesis lumen, said plurality of slots sized and configured to allow a first osteogenic composition disposed in said first internal prosthesis lumen to be dispersed out of said first internal prosthesis lumen and delivered to said dysfunctional SI joint when said SI joint prosthesis is said inserted into said pilot SI joint opening in said dysfunctional SI joint.

12. The system of claim 7, wherein, when said SI joint prosthesis is said inserted into said pilot SI joint opening in said dysfunctional SI joint, said SI joint prosthesis transfixes said dysfunctional SI joint.

13. The system of claim 1, wherein said first, said second, and said third drill guide fixation sub-systems are operable when said K-wire pin member is said received in said first lobe portion of said prosthesis internal access opening in said drill guide and said engages said first bone structure of said dysfunctional SI joint, and said bone dislodging member is said received in said second lobe portion of said prosthesis internal access opening in said drill guide and creates said first portion of said pilot SI joint opening in said second bone structure of said dysfunctional SI joint, and when said K-wire pin member is said received in said second lobe portion of said prosthesis internal access opening in said drill guide and said engages said second bone structure of said dysfunctional SI joint, and said bone dislodging member is received in said first lobe portion of said prosthesis internal access opening in said drill guide and creates said second portion of said pilot SI joint opening in said first bone structure of said dysfunctional SI joint.

14. The system of claim 13, wherein said first, said second, and said third drill guide fixation sub-systems are further operable when said temporary fixation pin is said received in said first lobe portion of said prosthesis internal access opening in said drill guide and said engages said first bone structure of said dysfunctional SI joint, and said bone dislodging member is said received in said second lobe portion of said prosthesis internal access opening in said drill guide and creates said first portion of said pilot SI joint opening in said second bone structure of said dysfunctional SI joint, and when said temporary fixation pin is said received in said second lobe portion of said prosthesis internal access opening in said drill guide and said engages said second bone structure of said dysfunctional SI joint, and said bone dislodging member is said received in said first lobe portion of said prosthesis internal access opening in said drill guide and creates said second portion of said pilot SI joint opening in said first bone structure of said dysfunctional SI joint.

* * * * *